(12) United States Patent
Sim et al.

(10) Patent No.: US 12,133,458 B2
(45) Date of Patent: Oct. 29, 2024

(54) ORGANIC ELECTROLUMINESCENCE DEVICE AND NITROGEN-CONTAINING COMPOUND FOR ORGANIC ELECTROLUMINESCENCE DEVICE

(71) Applicant: Samsung Display Co., Ltd., Yongin-si (KR)

(72) Inventors: Mun-ki Sim, Seoul (KR); Junha Park, Gwacheon-si (KR); Jangyeol Baek, Yongin-si (KR); Hyoyoung Lee, Suwon-si (KR); Soo-byung Ko, Yongin-si (KR); Youngkook Kim, Suwon-si (KR); Seokhwan Hwang, Suwon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 563 days.

(21) Appl. No.: 16/377,046

(22) Filed: Apr. 5, 2019

(65) Prior Publication Data
US 2019/0319196 A1  Oct. 17, 2019

(30) Foreign Application Priority Data
Apr. 17, 2018  (KR) .......... 10-2018-0044497

(51) Int. Cl.
*H10K 85/60* (2023.01)
*C07D 403/10* (2006.01)
(Continued)

(52) U.S. Cl.
CPC ......... *H10K 85/654* (2023.02); *C07D 403/10* (2013.01); *C07D 403/14* (2013.01);
(Continued)

(58) Field of Classification Search
CPC .......... H01L 51/0067; H01L 51/0072; H01L 51/0074; H01L 51/5012; H01L 2251/5384;
(Continued)

(56) References Cited

U.S. PATENT DOCUMENTS 10,186,665 B2  1/2019  Kawamura et al.
10,193,079 B2  1/2019  Stoessel et al.
(Continued)

FOREIGN PATENT DOCUMENTS

CN  107431136 A  12/2017
CN  107667102 A  2/2018
(Continued)

OTHER PUBLICATIONS

Zhang, Qisheng et al; "Efficient blue organic light-emitting diodes employing thermally activated delayed fluorescence"; Nature Photonics; Apr. 2014, pp. 326-332, vol. 8, Macmillan Publishers Limited.
(Continued)

*Primary Examiner* — Michael Y Sun
(74) *Attorney, Agent, or Firm* — Lewis Roca Rothgerber Christie LLP

(57) ABSTRACT

An organic electroluminescence device includes a first electrode, a hole transport region provided on the first electrode, an emission layer provided on the hole transport region, an electron transport region provided on the emission layer, and a second electrode provided on the electron transport region. The emission layer includes a nitrogen-containing compound. The nitrogen-containing compound includes a triazine moiety and a carbazole moiety. In the carbazole moiety, at least one position among 2, 3 and 7 is substituted; each of positions 2 and 7 is substituted or unsubstituted with a substituted or unsubstituted phenyl group, or a substituted or
(Continued)

unsubstituted carbazole group; and position 3 is substituted or unsubstituted with a substituted or unsubstituted phenyl group.

21 Claims, 2 Drawing Sheets

(51) Int. Cl.
    *C07D 403/14*      (2006.01)
    *C07D 409/14*      (2006.01)
    *C09K 11/06*      (2006.01)
    *H10K 50/11*      (2023.01)

(52) U.S. Cl.
    CPC ............ *C07D 409/14* (2013.01); *C09K 11/06* (2013.01); *H10K 85/6572* (2023.02); *H10K 85/6576* (2023.02); *C09K 2211/1018* (2013.01); *H10K 50/11* (2023.02)

(58) Field of Classification Search
    CPC ............... H01L 51/5004; C09K 11/06; C09K 2211/1018; C07D 403/10; C07D 409/14; C07D 403/14; H10K 85/654; H10K 85/6572; H10K 85/6576; H10K 50/11; H10K 2101/20; H10K 2101/40; H10K 2101/90; H10K 50/12
    See application file for complete search history.

(56) References Cited

U.S. PATENT DOCUMENTS

| | | | |
|---|---|---|---|
| 10,547,009 | B2 | 1/2020 | Yoshida et al. |
| 2003/0138657 | A1* | 7/2003 | Li ........................ H10K 85/114 428/690 |
| 2005/0127823 | A1† | 6/2005 | Iwakuma |
| 2015/0041785 | A1† | 2/2015 | Sannomiya |
| 2015/0141642 | A1 | 5/2015 | Adachi et al. |
| 2015/0349273 | A1 | 12/2015 | Hung et al. |
| 2015/0357582 | A1 | 12/2015 | Hirata et al. |
| 2017/0117488 | A1 | 4/2017 | Ahn et al. |
| 2017/0194574 | A1 | 7/2017 | Ishidai et al. |
| 2017/0244049 | A1 | 8/2017 | Aspuru-Guzik et al. |
| 2018/0026202 | A1 | 1/2018 | Danz et al. |
| 2018/0123049 | A1* | 5/2018 | Lee .................... C07D 491/048 |
| 2019/0194171 | A1* | 6/2019 | Bergmann ........... H10K 85/654 |
| 2019/0233412 | A1* | 8/2019 | Cheng ................. C07D 409/14 |

FOREIGN PATENT DOCUMENTS

| | | | |
|---|---|---|---|
| JP | 2006306783 A | † | 11/2006 |
| JP | 2012216801 A | † | 11/2012 |
| JP | 2017-123460 A | | 7/2017 |
| JP | 2017197481 A | † | 11/2017 |
| JP | 6249150 B2 | | 12/2017 |
| JP | 6249151 B2 | | 12/2017 |
| KR | 20100117947 | * | 11/2010 |
| KR | 10-2015-0016242 A | | 2/2015 |
| KR | 10-2015-0099762 A | | 9/2015 |
| KR | 10-2015-0116776 A | | 10/2015 |
| KR | 10-2015-0132872 A | | 11/2015 |
| KR | 10-2015-0139459 A | | 12/2015 |
| KR | 10-2017-0005853 A | | 1/2017 |
| KR | 20170049291 | * | 5/2017 |
| KR | 10-2017-0088822 A | | 8/2017 |
| WO | WO 2012/077902 A2 | | 6/2012 |
| WO | WO 2012/108881 A1 | | 8/2012 |
| WO | 2013012297 A1 | † | 1/2013 |
| WO | WO 2014/017045 A1 | | 1/2014 |
| WO | WO-2016080791 A1 | * | 5/2016 ........... C07D 409/14 |
| WO | WO 2016/089080 A1 | | 6/2016 |

OTHER PUBLICATIONS

Chinese Office Action dated Mar. 1, 2023, for corresponding Application No. 201910309606.6, 11 pages.

\* cited by examiner
† cited by third party

ORGANIC ELECTROLUMINESCENCE DEVICE AND NITROGEN-CONTAINING COMPOUND FOR ORGANIC ELECTROLUMINESCENCE DEVICE

CROSS-REFERENCE TO RELATED APPLICATION

This application claims priority to and the benefit of Korean Patent Application No. 10-2018-0044497, filed on Apr. 17, 2018, the entire content of which is incorporated herein by reference.

BACKGROUND

1. Field

The present disclosure herein relates to an organic electroluminescence device and a nitrogen-containing compound utilized in the organic electroluminescence device.

2. Description of the Related Art

The development of an organic electroluminescence device as an image display device is being actively conducted. Different from a liquid crystal display device, the organic electroluminescence device is a so-called self-luminescent display device, in which holes and electrons injected from a first electrode and a second electrode recombine in an emission layer, and a light emission material including an organic compound in the emission layer emits light to display an image.

As an organic electroluminescence device, for example, a device including a first electrode, a hole transport layer disposed on the first electrode, an emission layer disposed on the hole transport layer, an electron transport layer disposed on the emission layer, and a second electrode disposed on the electron transport layer is known. Holes are injected from the first electrode, and the injected holes move via the hole transport layer and are injected into the emission layer. Meanwhile, electrons are injected from the second electrode, and the injected electrons move via the electron transport layer and are injected into the emission layer. The holes and electrons injected into the emission layer recombine to produce excitons in the emission layer. The organic electroluminescence device emits light utilizing light generated by the transition of the excitons to a ground state.

SUMMARY

An aspect of the present disclosure is directed toward an organic electroluminescence device and a nitrogen-containing compound utilized in the organic electroluminescence device.

According to an embodiment of the inventive concept, an organic electroluminescence device includes a first electrode, a hole transport region on the first electrode, an emission layer on the hole transport region, an electron transport region on the emission layer, and a second electrode on the electron transport region. The emission layer includes a nitrogen-containing compound including a triazine moiety and a carbazole moiety. In the carbazole moiety, at least one position among 2, 3 and 7 is substituted; each of positions 2 and 7 is substituted or unsubstituted with a substituted or unsubstituted phenyl group, or a substituted or unsubstituted carbazole group; and position 3 is substituted or unsubstituted with a substituted or unsubstituted phenyl group.

In an embodiment, one of positions 2 and 3 of the carbazole moiety may be unsubstituted.

In an embodiment, the nitrogen-containing compound may include one or two carbazole moieties.

In an embodiment, the triazine moiety may be substituted with one or more substituted or unsubstituted phenyl groups.

In an embodiment, the emission layer may include a host and a dopant, and the dopant may include the nitrogen-containing compound. The dopant may be a thermally activated delayed fluorescence dopant.

In an embodiment, the emission layer may include a host and a dopant, and the host may include the nitrogen-containing compound.

In an embodiment, the nitrogen-containing compound may be represented by the following Formula 1:

Formula 1

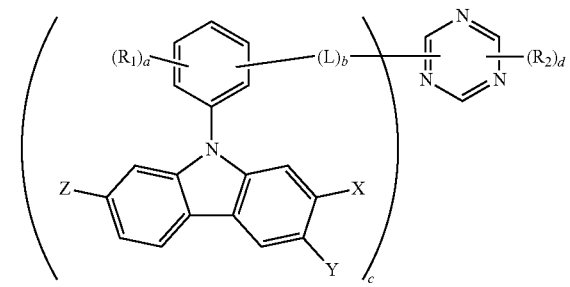

In Formula 1, X and Z are each independently a hydrogen atom, a deuterium atom, a substituted or unsubstituted phenyl group, or a substituted or unsubstituted carbazole group; Y is a hydrogen atom, a deuterium atom, or a substituted or unsubstituted phenyl group; at least one of X, Y or Z is not a hydrogen atom and is not a deuterium atom; one of X and Y is a hydrogen atom or a deuterium atom; $R_1$ and $R_2$ are each independently a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring; L is a substituted or unsubstituted arylene group having 6 to 30 carbon atoms for forming a ring, or a substituted or unsubstituted heteroarylene group having 2 to 30 carbon atoms for forming a ring; a is an integer of 0 to 4; b is an integer of 0 to 2; c is 1 or 2; and d is 1 or 2.

In an embodiment, Z may be an unsubstituted phenyl group, or a phenyl group substituted with at least one of a cyano group, a halogen atom, an alkyl group having 1 to 5 carbon atoms, or an aryl group having 6 to 15 carbon atoms for forming a ring.

In an embodiment, a may be 0 or 1, wherein when a is 1, $R_1$ may be a substituted or unsubstituted dibenzothiophene group, or a substituted or unsubstituted dibenzofuran group.

In an embodiment, the nitrogen-containing compound represented by Formula 1 may be represented by the following Formula 1-1 or Formula 1-2:

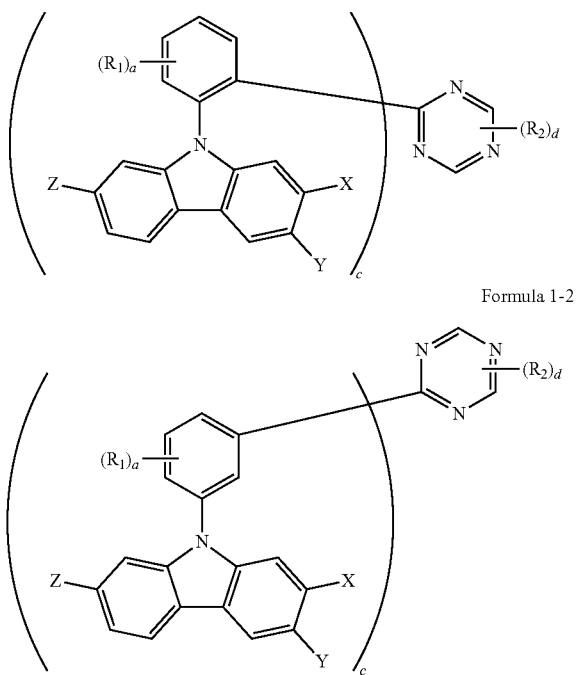

Formula 1-1

Formula 1-2

In Formulae 1-1 and 1-2, X, Y, Z, $R_1$, $R_2$, a, c and d are the same as respectively defined in Formula 1.

In an embodiment of the inventive concept, an organic electroluminescence device includes a first electrode, a hole transport region on the first electrode, an emission layer on the hole transport region, an electron transport region on the emission layer, and a second electrode on the electron transport region, wherein the emission layer includes a nitrogen-containing compound represented by Formula 1 above.

In an embodiment of the inventive concept, there is provided a nitrogen-containing compound represented by Formula 1 above.

In addition, an embodiment of the configuration of the organic electroluminescence device is not limited thereto, but various suitable modifications may be possible.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
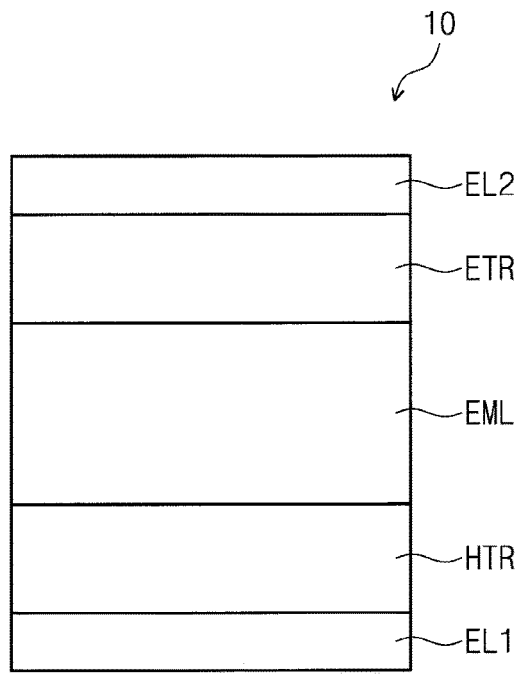
FIG. 1 is a cross-sectional view schematically illustrating an organic electroluminescence device according to an embodiment of the inventive concept.

The above objects, other objects, features and enhancements of the inventive concept will be easily understood from exemplary embodiments with reference to the accompanying drawings. The inventive concept may, however, be embodied in different forms and should not be construed as limited to the embodiments set forth herein. Rather, exemplary embodiments are provided so that the contents disclosed herein become thorough and complete, and the spirit of the inventive concept is sufficiently disclosed for a person skilled in the art.

Like reference numerals refer to like elements for explaining each drawing. In the drawings, the sizes of elements may be enlarged for clarity of the inventive concept. It will be understood that, although the terms first, second, etc., may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc., is referred to as being "on" another part, it can be "directly on" the other part, or intervening layers may also be present. Similarly, when a layer, a film, a region, a plate, etc., is referred to as being "under" another part, it can be "directly under" the other part, or intervening layers may also be present.

First, an organic electroluminescence device according to an embodiment of the inventive concept will be explained referring to FIG. 1 to FIG. 3.

FIG. 1 is a cross-sectional view schematically illustrating an organic electroluminescence device according to an embodiment of the inventive concept. FIG. 2 is a cross-sectional view schematically illustrating an organic electroluminescence device according to an embodiment of the inventive concept. FIG. 3 is a cross-sectional view schematically illustrating an organic electroluminescence device according to an embodiment of the inventive concept.

Figure 2:
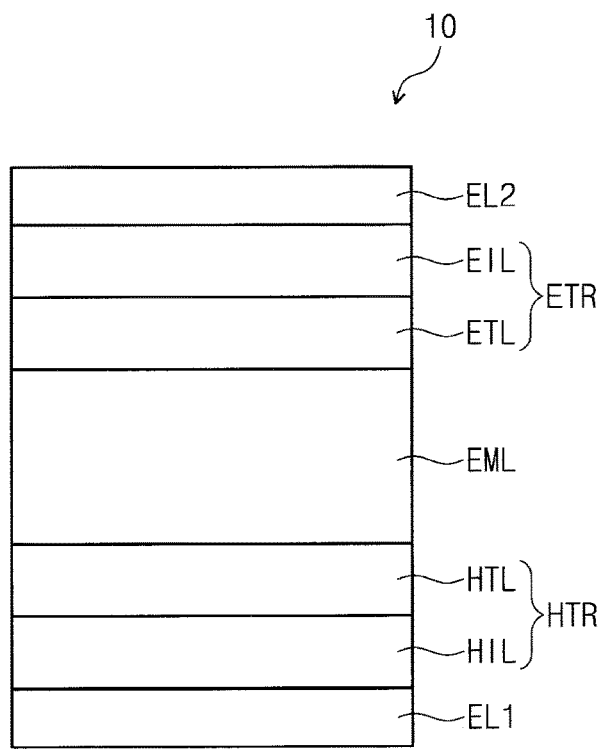
FIG. 2 is a cross-sectional view schematically illustrating an organic electroluminescence device according to an embodiment of the inventive concept.
Figure 3:
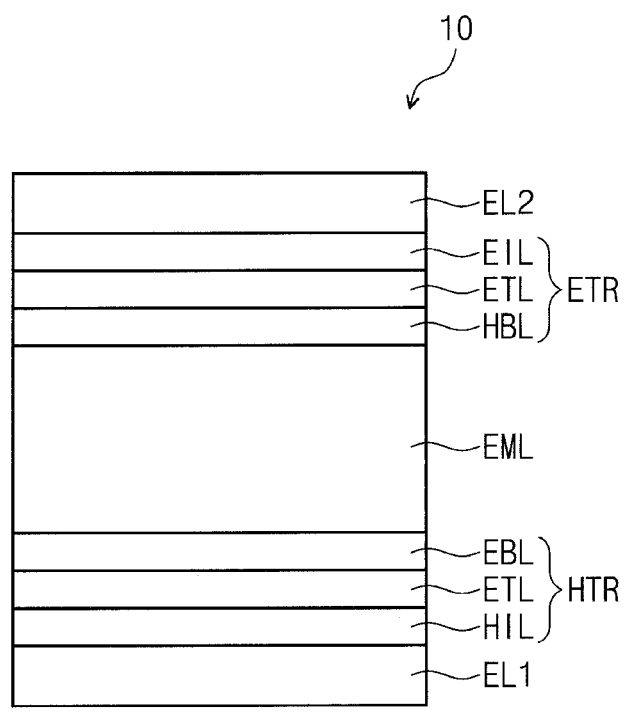
FIG. 3 is a cross-sectional view schematically illustrating an organic electroluminescence device according to an embodiment of the inventive concept.

Referring to FIG. 1 to FIG. 3, an organic electroluminescence device 10 according to an embodiment of the inventive concept includes a first electrode EL1, a hole transport region HTR, an emission layer EML, an electron transport region ETR and a second electrode EL2.

The first electrode EL1 has conductivity. The first electrode EL1 may be a pixel electrode or an anode. The first electrode EL1 may be a transmissive electrode, a transflective electrode, or a reflective electrode. If the first electrode EL1 is the transmissive electrode, the first electrode EL1 may include a transparent metal oxide such as indium tin oxide (ITO), indium zinc oxide (IZO), zinc oxide (ZnO), and/or indium tin zinc oxide (ITZO). If the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include a plurality of layers including the reflective layer or transflective layer formed utilizing the above materials, and a transparent layer formed utilizing ITO, IZO, ZnO, and/or ITZO. For example, the first electrode EL1 may have a three-layer structure of ITO/Ag/ITO, without being limited thereto.

The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, or an electron blocking layer EBL. The thickness of the hole transport region HTR may be from about 1,000 Å to about 1,500 Å

The hole transport region HTR may have a single layer formed utilizing a single material, a single layer formed utilizing a plurality of different materials, or a multilayer structure including a plurality of layers formed utilizing a plurality of different materials.

For example, the hole transport region HTR may have the structure of a single layer such as a hole injection layer HIL, or a hole transport layer HTL, and may have a structure of a single layer formed utilizing a plurality of different materials, such as a hole injection material and a hole transport material. Alternatively, the hole transport region HTR may have a structure laminated from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without being limited thereto.

The hole transport region HTR may be formed utilizing various suitable methods, such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound (such as copper phthalocyanine), N,N'-diphenyl-N,N'-bis-[4-(phenyl-m-tolyl-amino)-phenyl]-biphenyl-4,4'-diamine (DNTPD), 4,4',4''-tris(3-methylphenylphenylamino) triphenylamine (m-MTDATA), 4,4', 4''-tris(N,N-diphenylamino)triphenylamine (TDATA), 4,4', 4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, tetrakis(pentafluorophenyl)borate, dipyrazino[2,3-f: 2',3'-h] quinoxaline-2,3,6,7,10,11-hexacarbonitrile (HAT-CN), etc.

The hole transport layer HTL may include, for example, carbazole derivatives (such as N-phenyl carbazole, and polyvinyl carbazole), fluorine-based derivatives, N,N'-bis(3-methylphenyl)-N,N'-diphenyl-[1,1-biphenyl]-4,4'-diamine (TPD), triphenylamine-based derivatives (such as 4,4',4''-tris(N-carbazolyl)triphenylamine (TCTA)), N,N'-di(naphthalene-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be from about 100 Å to about 10,000 Å, for example, from about 100 Å to about 1,000 Å. If the hole transport region HTR includes both the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. If the thicknesses of the hole transport region HTR, the hole injection layer HIL, and the hole transport layer HTL satisfy the above-described ranges, satisfactory hole transport properties may be obtained without a substantial increase of a driving voltage.

The hole transport region HTR may further include a charge generating material in addition to the above-described materials to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, without being limited thereto. For example, non-limiting examples of the p-dopant may include quinone derivatives (such as tetracyanoquinodimethane (TCNQ) and 2,3,5,6-tetrafluoro-tetracyanoquinodimethane (F4-TCNQ)), and metal oxides (such as tungsten oxide, and molybdenum oxide).

As described above, the hole transport region HTR may further include at least one of a hole buffer layer or an electron blocking layer in addition to the hole injection layer HIL and the hole transport layer HTL. The hole buffer layer may compensate a resonance distance according to the wavelength of light emitted from the emission layer EML and increase the light emission efficiency. Materials included in the hole transport region HTR may be utilized as materials included in the hole buffer layer. The electron blocking layer is a layer reducing or preventing electron injection from the electron transport region ETR to the hole transport region HTR.

The emission layer EML is provided on the hole transport region HTR. The emission layer EML may have a thickness of about 100 Å to about 1,000 Å, or about 100 Å to about 300 Å. The emission layer EML may have a single layer formed utilizing a single material, a single layer formed utilizing a plurality of different materials, or a multilayer structure having a plurality of layers formed utilizing a plurality of different materials.

The emission layer EML includes a nitrogen-containing compound including a triazine moiety and a carbazole moiety. At least one among positions 2, 3 and 7 of the carbazole moiety is substituted. The numbering of substitution positions is shown below.

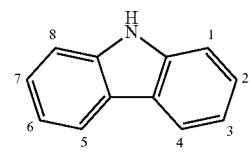 [SMILES: c1ccc2c(c1)[nH]c1ccccc12]

Each of the positions 2 and 7 of the carbazole group is substituted or unsubstituted with a substituted or unsubstituted phenyl group, or a substituted or unsubstituted carbazole group. In other words, if at least one of position 2 or 7 of the carbazole group is substituted, the substituent is a substituted or unsubstituted phenyl group, or a substituted or unsubstituted carbazole group.

In the description, "substituted or unsubstituted" may refer to (a functional group being) substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocycle (e.g., a heterocyclic group), unless otherwise separately defined, or unsubstituted. In addition, each of the substituent illustrated above may be substituted or unsubstituted. For example, a biphenyl group may be interpreted as an aryl group, or a phenyl group substituted with a phenyl group. The heterocycle may be an aliphatic heterocycle or an aromatic heterocycle (heteroaryl group).

In the description, the halogen atom may include a fluorine atom, a chlorine atom, a bromine atom and/or an iodine atom.

In the description, the alkyl group may be a linear, branched or cyclic alkyl group. The carbon number of the alkyl group may be from 1 to 30, 1 to 20, 1 to 10, or 1 to 5. The alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without being limited thereto.

In the description, the alkenyl group may have a linear chain or a branched chain. The carbon number is not specifically limited, but may be from 2 to 30, 2 to 20, or 2 to 10. Examples of the alkenyl group may include vinyl, 1-butenyl, 1-pentenyl, 1,3-butadienyl, styrenyl, styrylvinyl, etc. However, an embodiment of the inventive concept is not limited thereto.

In the description, the aryl group refers to an optional functional group or substituent derived from an aromatic hydrocarbon ring. The aryl group may be a monocyclic aryl group or a polycyclic aryl group. The carbon number for forming a ring in the aryl group may be from 6 to 60, 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, biphenylene, triphenylene, pyrenyl, benzofluoranthenyl, chrysenyl, etc., without being limited thereto.

In the description, the fluorenyl group may be substituted, and two substituents may be combined with each other to form a Spiro structure. Non-limiting examples of the substituted fluorenyl groups are shown below. However, an embodiment of the inventive concept is not limited thereto.

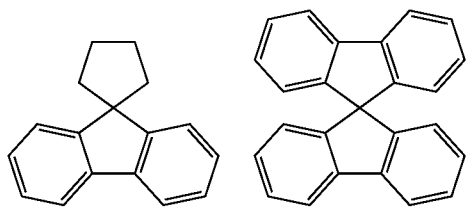

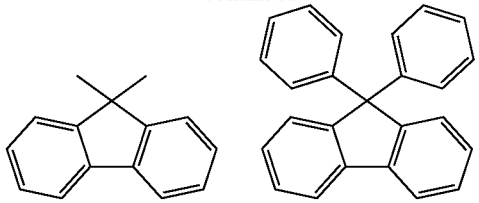

In the description, the heteroaryl group may include at least one of B, O, N, P, Si or S as a heteroatom in forming the ring. If the heteroaryl group includes two heteroatoms, two heteroatoms may be the same or different. The heteroaryl group may be monocyclic heteroaryl group or polycyclic heteroaryl group. The carbon number for forming a ring of the heteroaryl group may be from 2 to 30, 2 to 20, or 2 to 10. Examples of the heteroaryl group may include thiophene, furan, pyrrole, imidazole, thiazole, oxazole, oxadiazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc., without being limited thereto.

In the description, the silyl group may be an alkyl silyl group or an aryl silyl group. Examples of the silyl group may include trimethylsilyl, triethylsilyl, t-butyldimethylsilyl, vinyldimethylsilyl, propyldimethylsilyl, triphenylsilyl, diphenylsilyl, phenylsilyl, etc. However, an embodiment of the inventive concept is not limited thereto.

In the description, the boron group may be an alkyl boron group or an aryl boron group. Examples of the boron group may include trimethylboron, triethylboron, t-butyldimethylboron, triphenylboron, diphenylboron, phenylboron, etc. However, an embodiment of the inventive concept is not limited thereto.

In the description, the carbon number of the amino group is not specially limited, but may be 1 to 30. The amino group may be an alkyl amino group or an aryl amino group. Examples of the amino group include a methylamino group, a dimethylamino group, a phenylamino group, a diphenylamino group, a naphthylamino group, a 9-methyl-anthracenylamino group, a triphenylamino group, etc., without being limited thereto.

In the description, the phosphine oxide group may be substituted with, for example, at least one of an alkyl group or an aryl group. Examples of the phosphine oxide group include a phenyl phosphine oxide group, a diphenyl phosphine oxide group, etc., without being limited thereto.

In the description, the phosphine sulfide group may be substituted with at least one of an alkyl group or an aryl group.

In the description, the same explanation on the aryl group may be applied to the arylene group, except that the arylene group is a divalent group.

In the description, the same explanation on the heteroaryl group may be applied to the heteroarylene group, except that the heteroarylene group is a divalent group.

Position 3 of the carbazole group may be substituted or unsubstituted with a substituted or unsubstituted phenyl group. In other words, if position 3 of the carbazole group is substituted, a substituent may be a substituted or unsubstituted phenyl group.

The nitrogen atom of the carbazole group may be substituted with a substituted or unsubstituted phenyl group. In this case, the carbazole moiety and the triazine moiety may be connected via the phenyl group as a linker.

The nitrogen-containing compound may include one or two carbazole moieties. If the nitrogen-containing compound includes two carbazole moieties, two carbazole moieties may be the same or different.

The triazine moiety may be substituted. For example, the triazine moiety may be substituted with one or more substituted or unsubstituted phenyl groups. For example, the triazine moiety may be substituted with two phenyl groups. However, an embodiment of the inventive concept is not limited thereto, and the triazine moiety may be substituted with a heteroaryl group having 2 to 15 carbon atoms for forming a ring. For example, the triazine moiety may be substituted with a substituted or unsubstituted dibenzothiophene group, or a substituted or unsubstituted dibenzofuran group.

The nitrogen-containing compound may be represented by the following Formula 1:

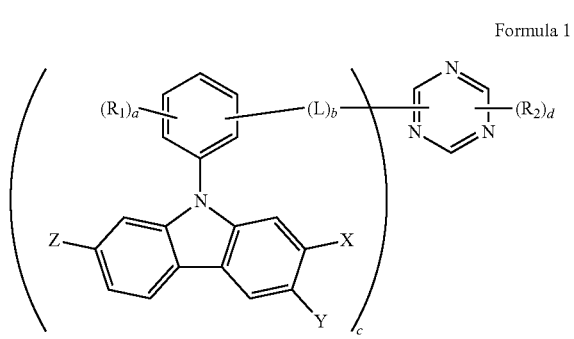

Formula 1

In Formula 1, X and Z are each independently a hydrogen atom, a deuterium atom, a substituted or unsubstituted phenyl group, or a substituted or unsubstituted carbazole group; Y is a hydrogen atom, a deuterium atom, or a substituted or unsubstituted phenyl group; at least one of X, Y or Z is not a hydrogen atom and is not a deuterium atom; one of X and Y is a hydrogen atom or a deuterium atom; $R_1$ and $R_2$ are each independently a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring; L is a substituted or unsubstituted arylene group having 6 to 30 carbon atoms for forming a ring, or a substituted or unsubstituted heteroarylene group having 2 to 30 carbon atoms for forming a ring; a is an integer of 0 to 4; b is an integer of 0 to 2; c is 1 or 2; and d is 1 or 2. For example, a sum of c and d (i.e., c+d) may be 3.

If a is 2 or more, a plurality of $R_1$ groups may be the same or different; if b is 2 or more, a plurality of L groups may be the same or different; and if d is 2 or more, a plurality of $R_2$ groups may be the same or different. If c is 2, the structures inside the parentheses of Formula 1 may be the same or different from each other.

If a is 1, $R_1$ may not be a hydrogen atom and may not be a deuterium atom, and if d is 1, $R_2$ may not be a hydrogen atom and may not be a deuterium atom.

Z may be a substituted or unsubstituted phenyl group. The substituent of the substituted phenyl group may be at least one of a cyano group, a halogen atom, an alkyl group having 1 to 5 carbon atoms or an aryl group having 6 to 15 carbon atoms for forming a ring. However, an embodiment of the inventive concept is not limited thereto, and Z may be a substituted or unsubstituted carbazole group.

The nitrogen-containing compound represented by Formula 1 may be, for example, represented by the following Formula 2 or 3:

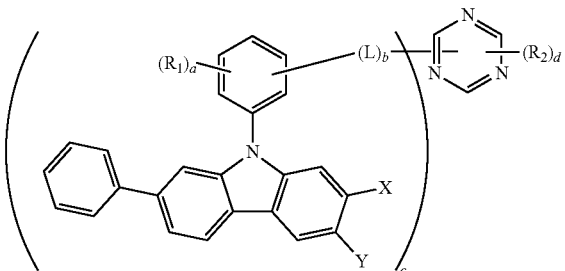

Formula 2

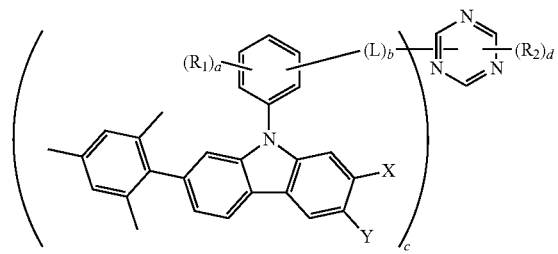

Formula 3

In Formulae 2 and 3, X, Y, L, $R_1$, $R_2$, b, c and d are the same as respectively defined in Formula 1.

In Formula 2, each of X and Y may be a hydrogen atom.

In Formula 2, one of X and Y may be a substituted or unsubstituted phenyl group, and the other one may be a hydrogen atom.

In Formula 3, each of X and Y may be a hydrogen atom.

In Formula 3, one of X and Y may be a substituted or unsubstituted phenyl group, and the other one may be a hydrogen atom.

The nitrogen-containing compound represented by Formula 1 may be, for example, represented by Formula 1-1 or 1-2 below. However, an embodiment of the inventive concept is not limited thereto. A carbazole moiety and a triazine moiety may be substituted via a linker in the para position.

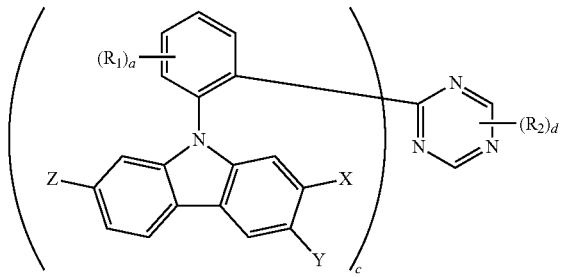

Formula 1-1

Formula 1-2

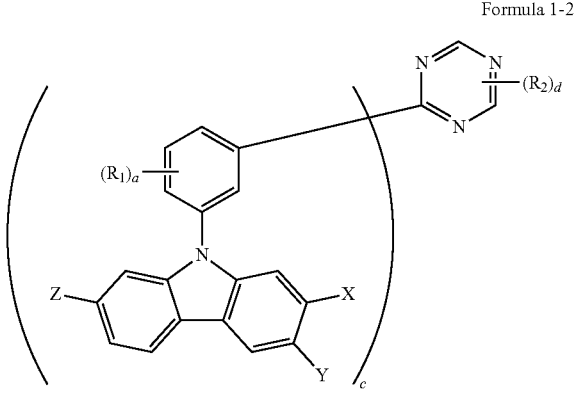

In Formulae 1-1 and 1-2, X, Y, Z, $R_1$, $R_2$, a, c and d are the same as respectively defined in Formula 1.

In Formula 1, b may be 0.

In Formula 1, b may be 1, and L may be a substituted or unsubstituted phenylene group.

In Formula 1, a may be 0 or 1. If a is 1, $R_1$ may be a substituted or unsubstituted dibenzothiophene group, or a substituted or unsubstituted dibenzofuran group.

The nitrogen-containing compound represented by Formula 1 may be, for example, represented by the following Formula 4:

Formula 4

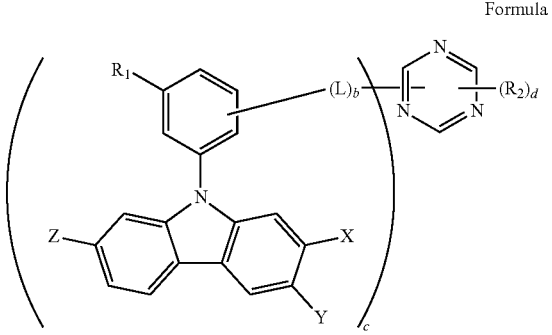

In Formula 4, X, Y, Z, L, $R_2$, b, c and d are the same as respectively defined in Formula 1.

The nitrogen-containing compound represented by Formula 1 may be, for example, represented by the following Formula 5:

Formula 5

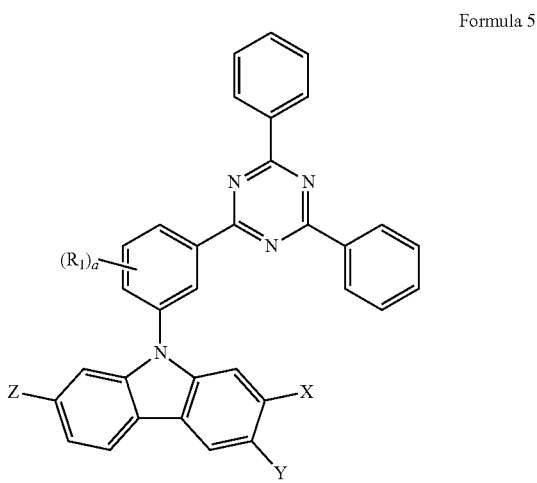

In Formula 5, X, Y, Z, $R_1$ and a are the same as respectively defined in Formula 1.

In Formula 1, d may be 2 and two $R_2$ groups may be each independently a substituted or unsubstituted phenyl group, a substituted or unsubstituted dibenzothiophene group, or a substituted or unsubstituted dibenzofuran group.

The nitrogen-containing compound may be one selected from the compounds represented in Compound Group 1 below. However, an embodiment of the inventive concept is not limited thereto.

Compound Group 1

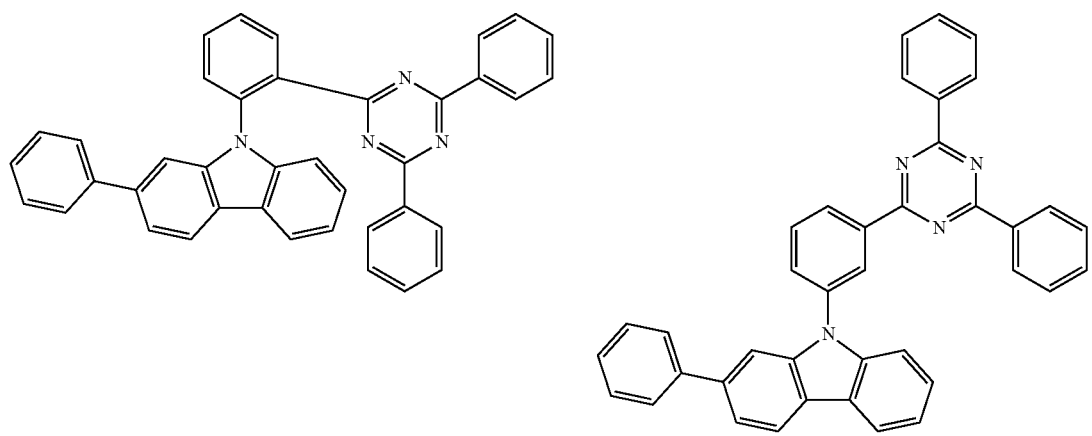

3
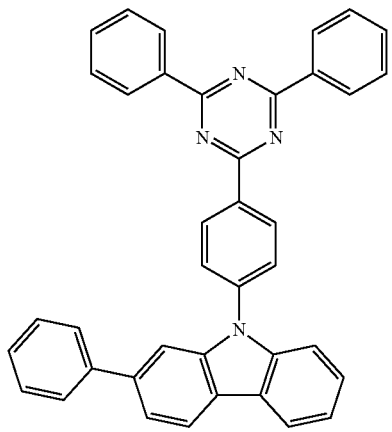
4
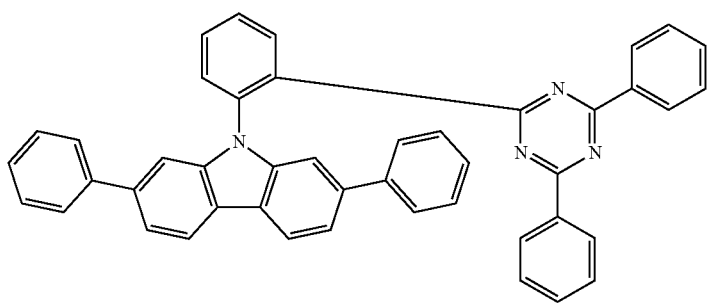
5
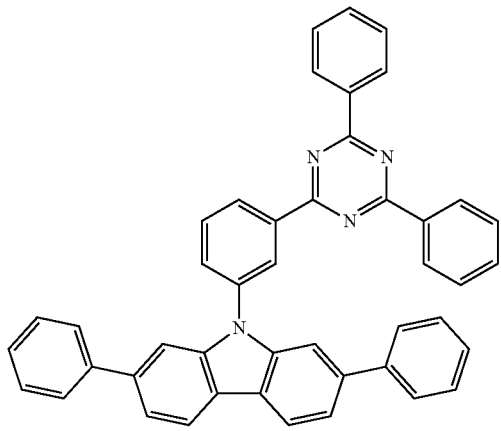
6
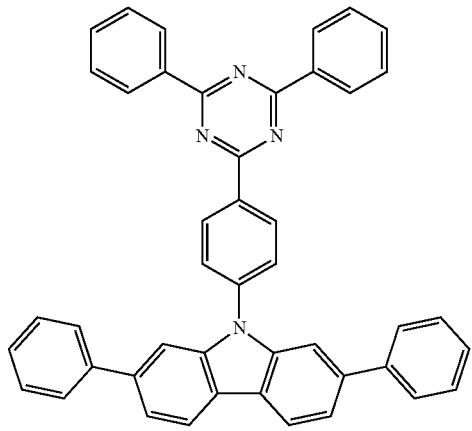

-continued
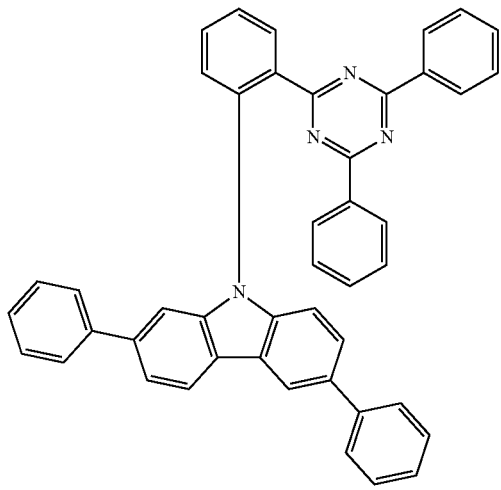
7
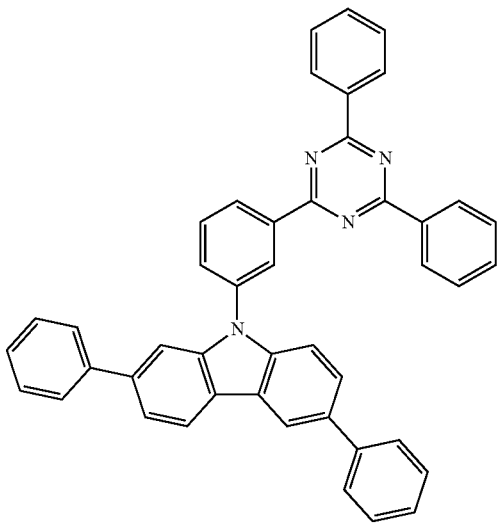
8
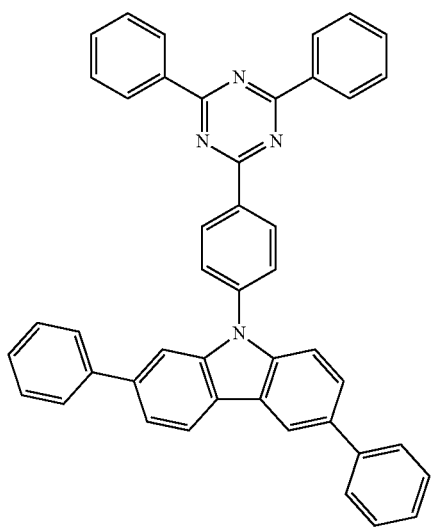
9
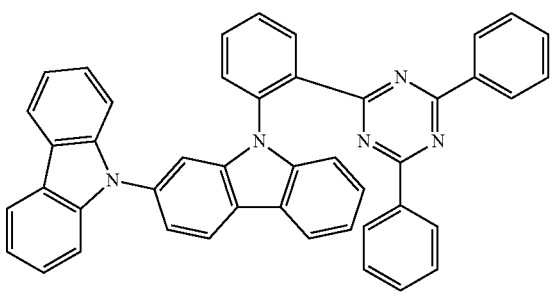
10
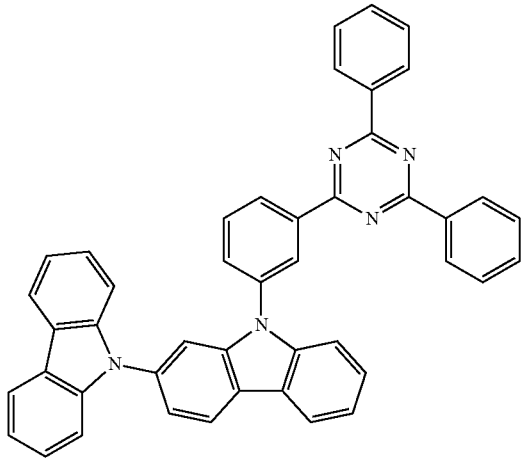
11
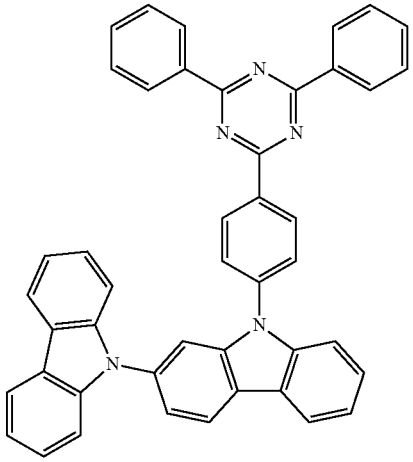
12

-continued
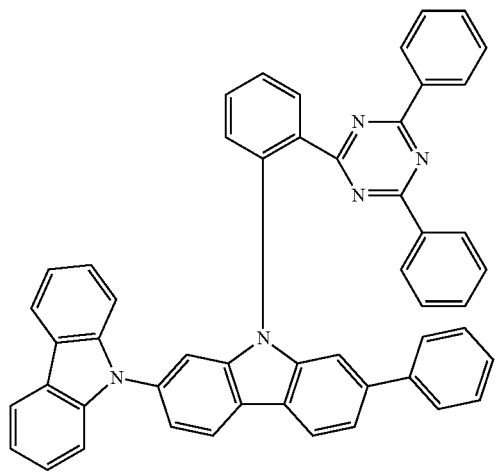
13
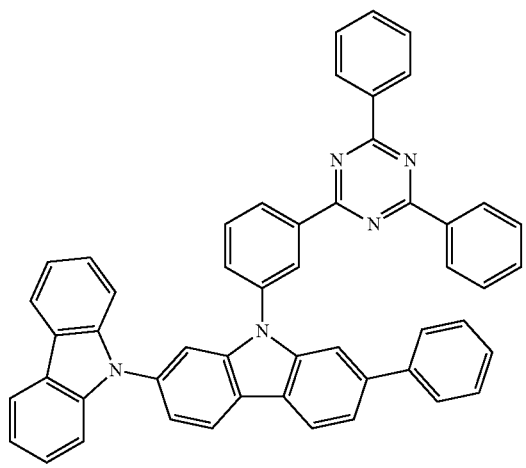
14
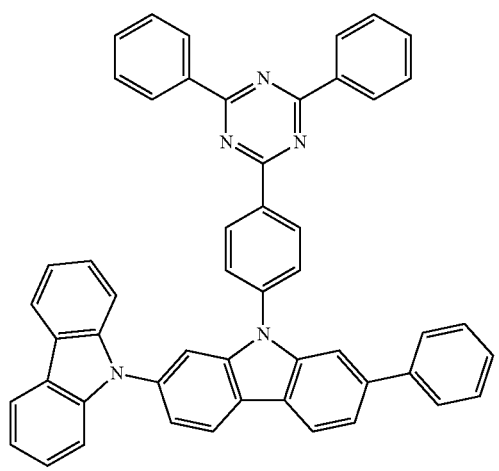
15
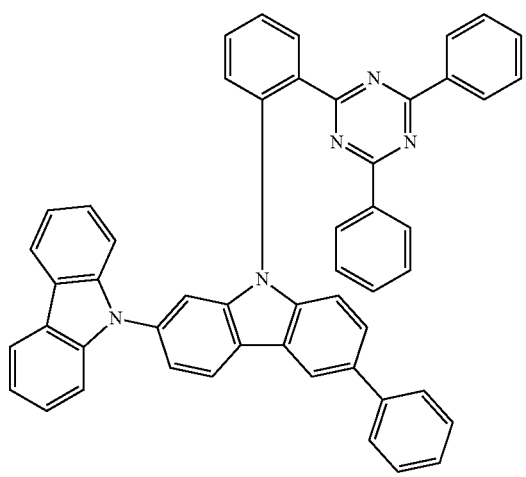
16
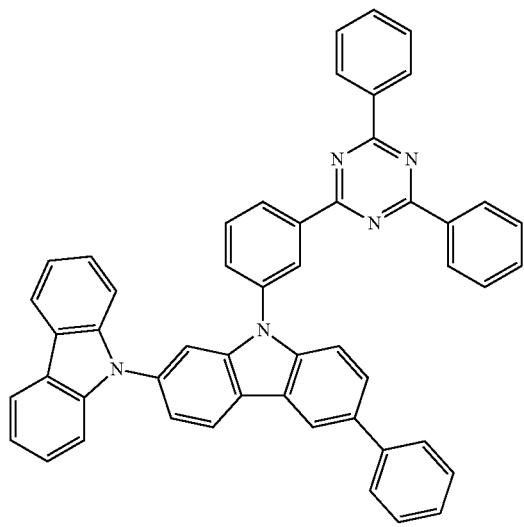
17
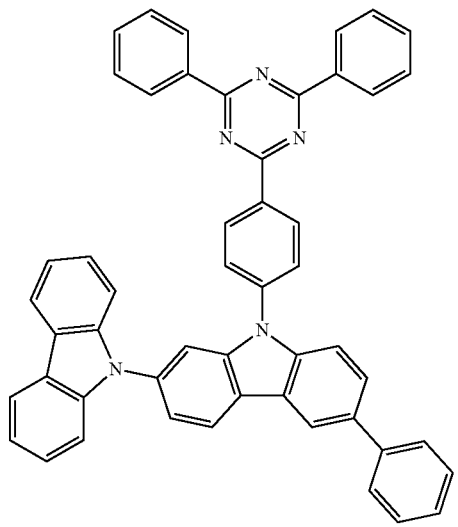
18

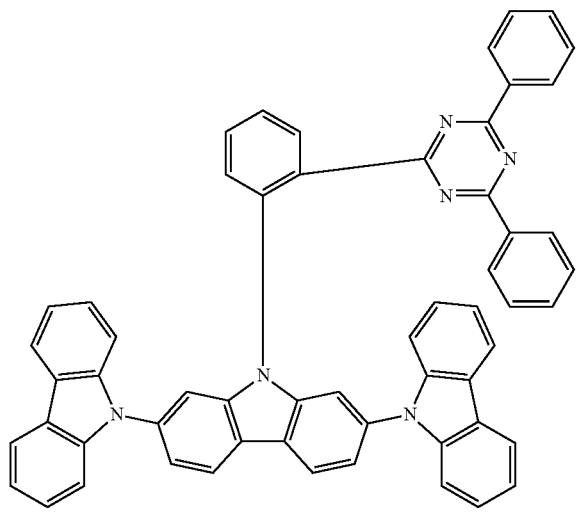
19
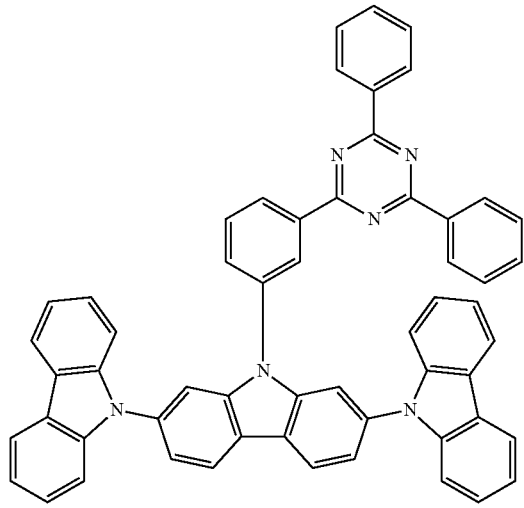
20
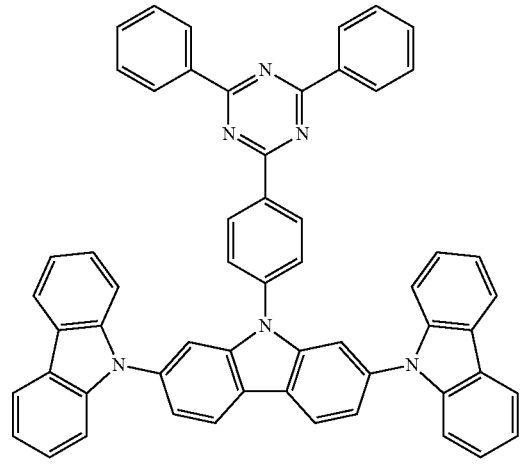
21
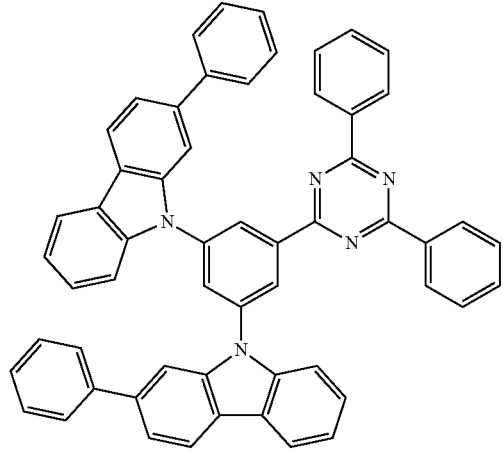
22
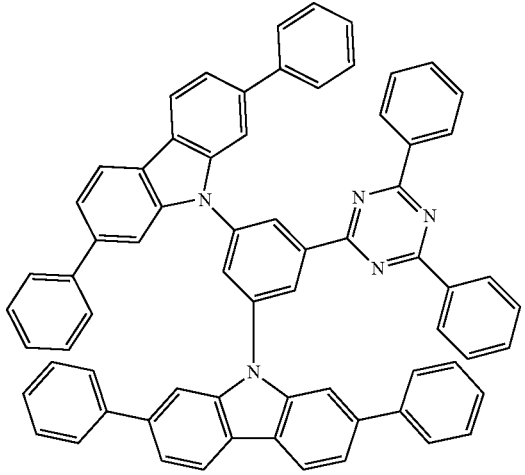
23

-continued
24
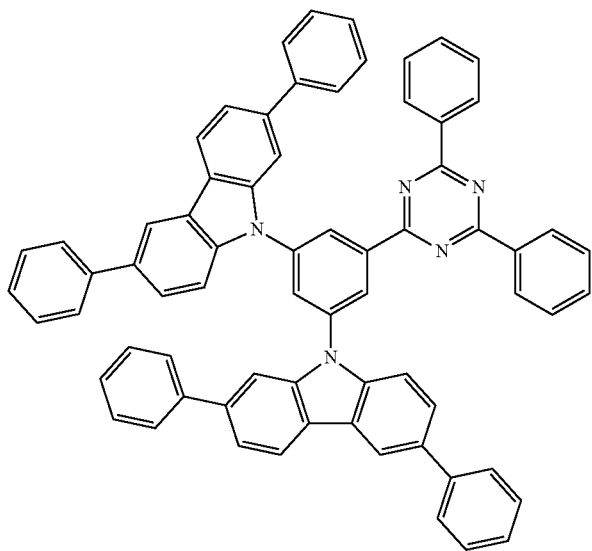
25
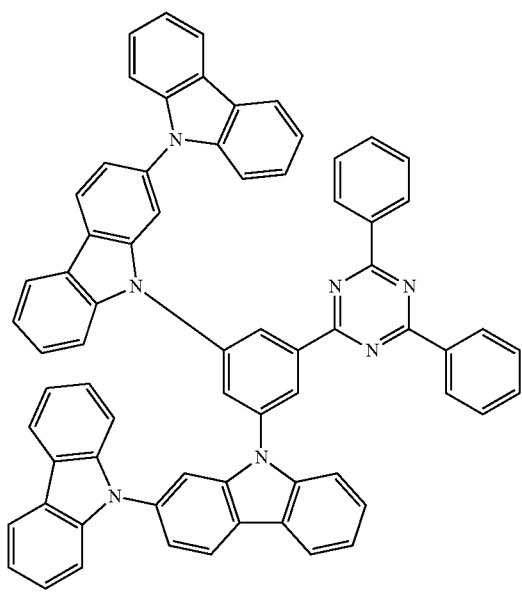

-continued
26
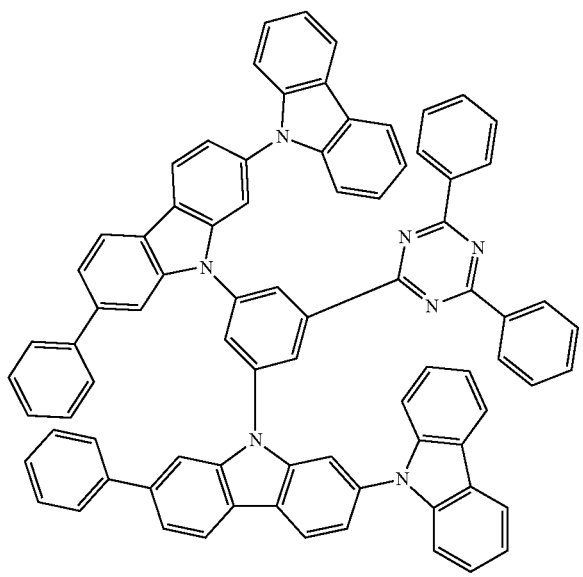
27
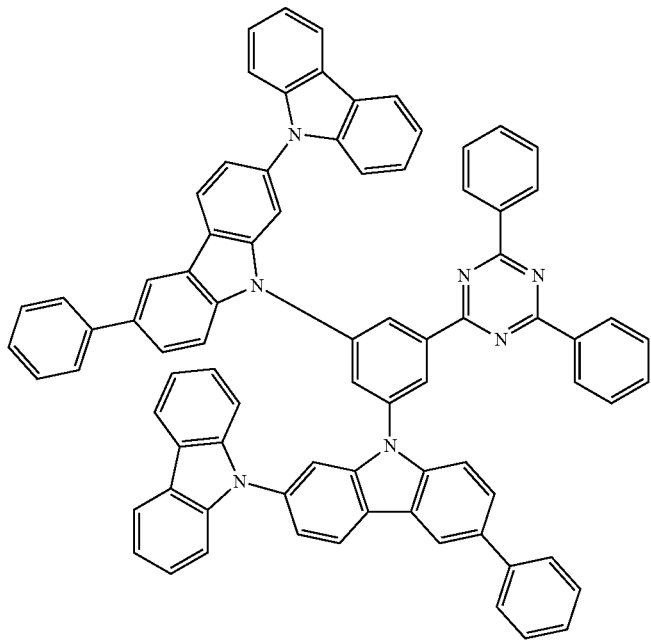
28
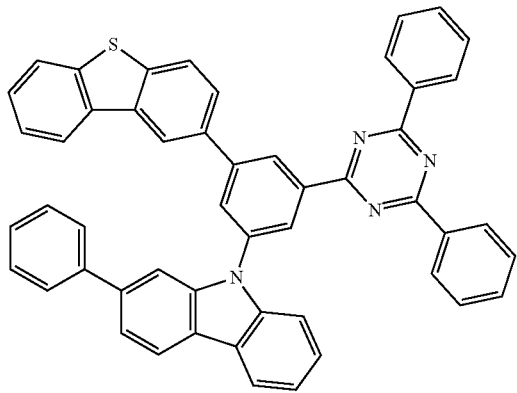
29
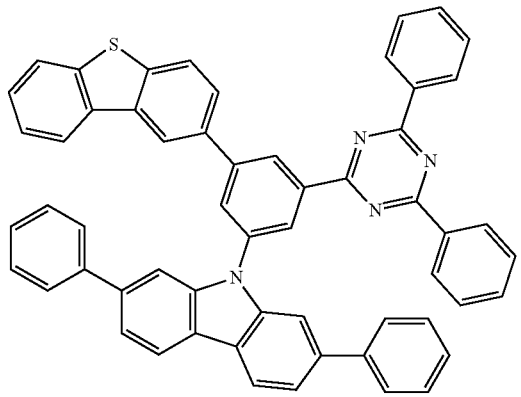

-continued
30
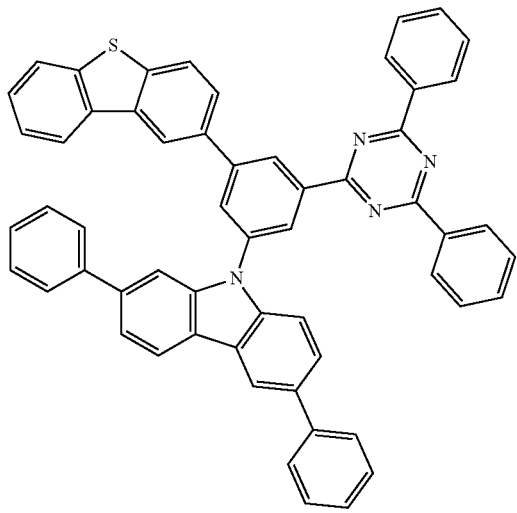
31
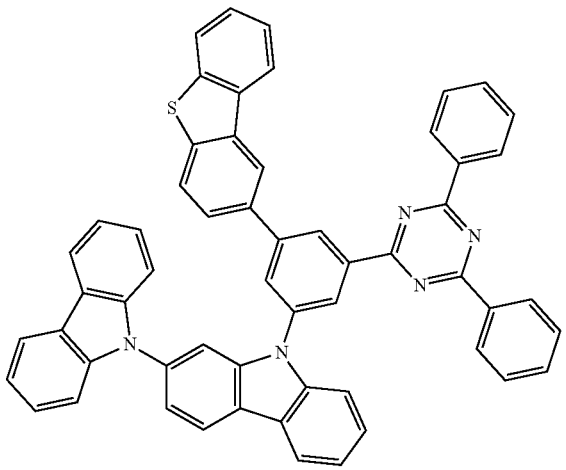
32
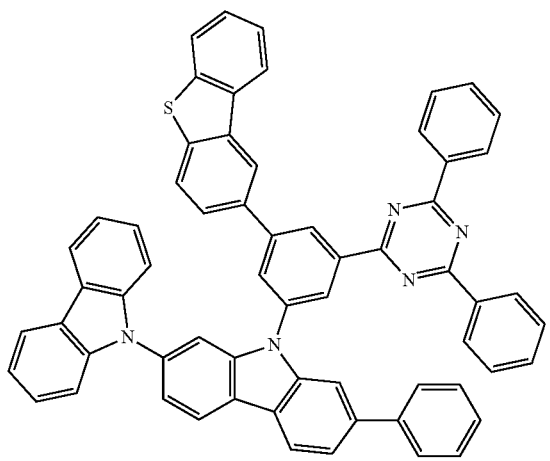
33
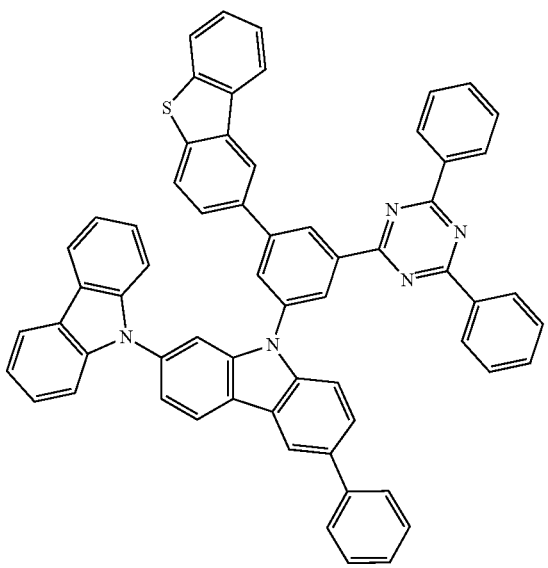
34
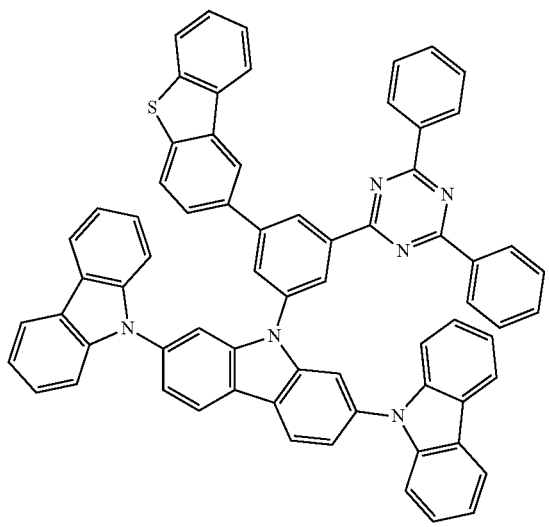
35
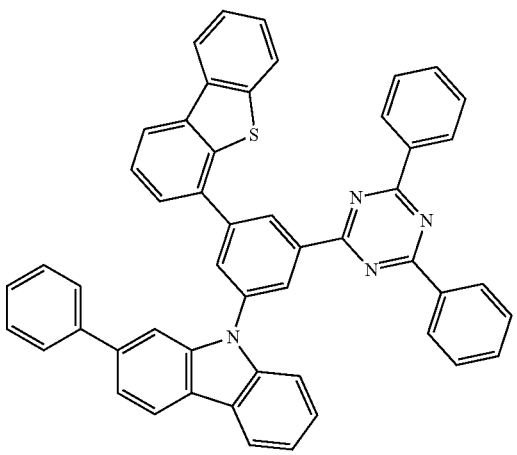

-continued
36
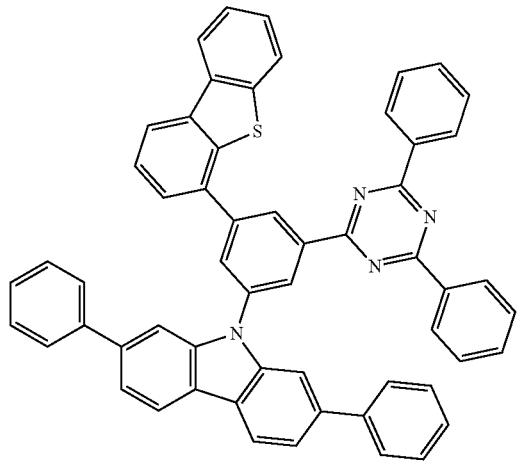
37
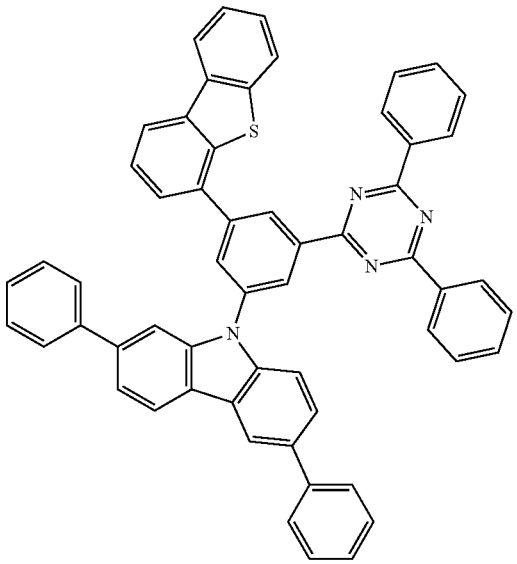
38
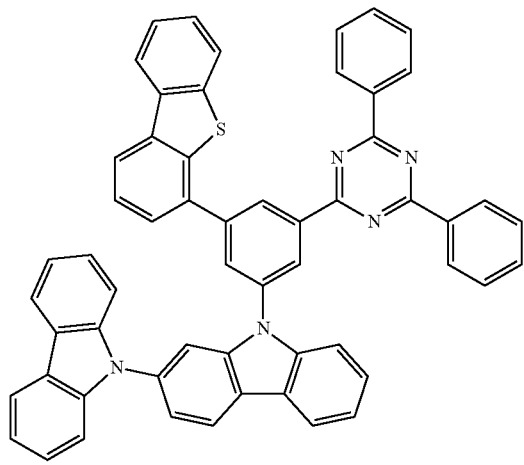
39
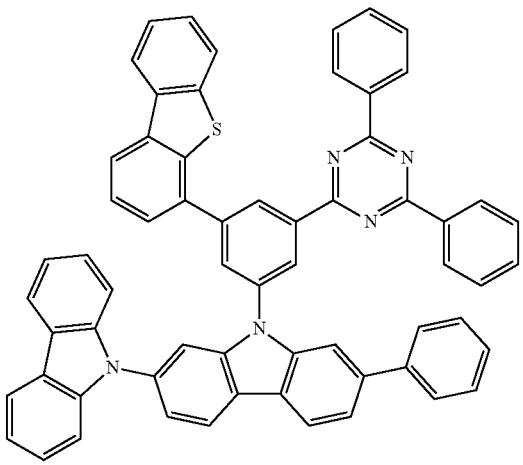
40
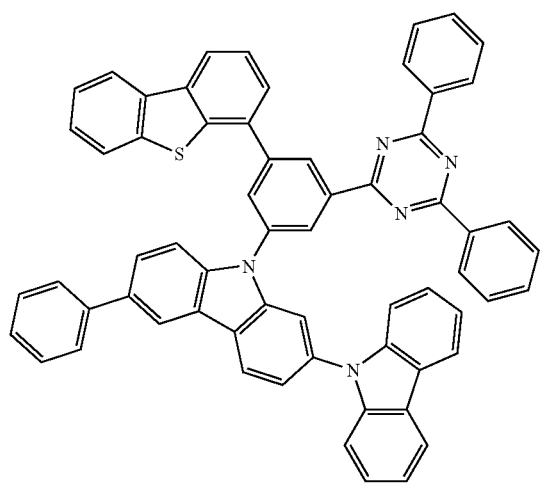
41
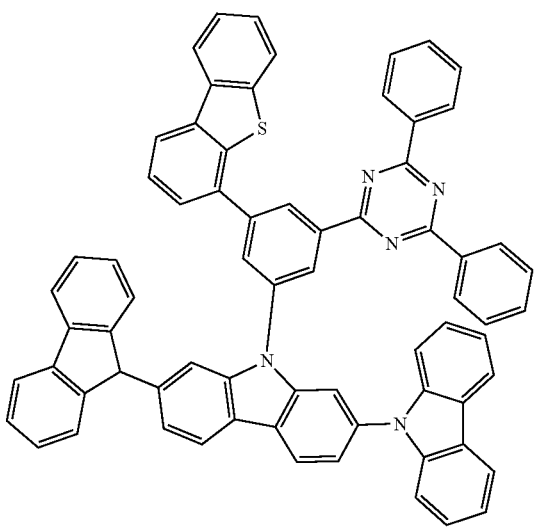

-continued
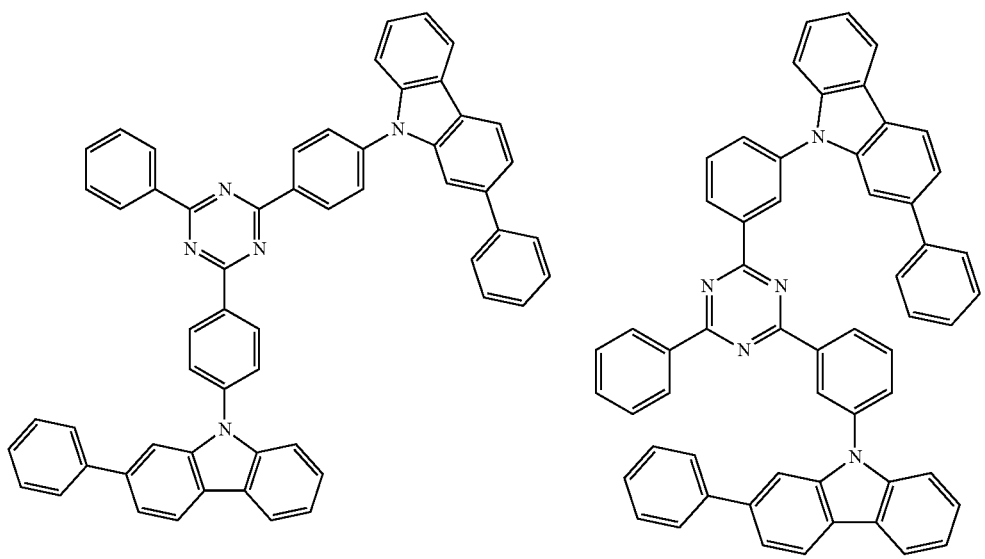
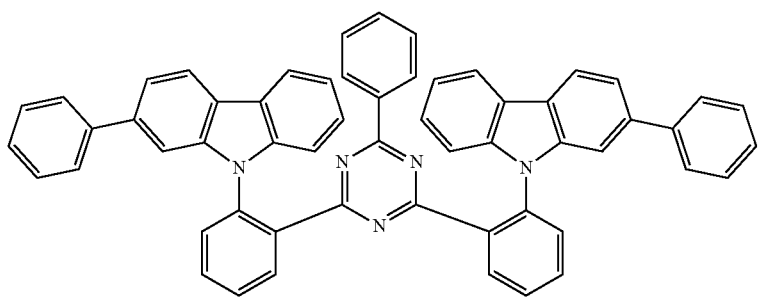
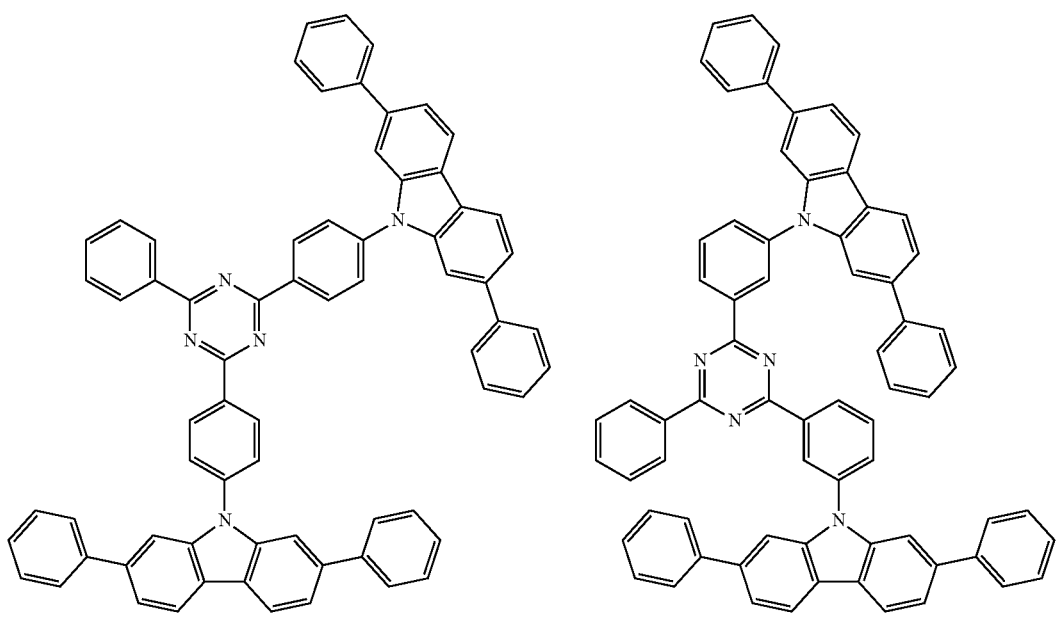

-continued
47
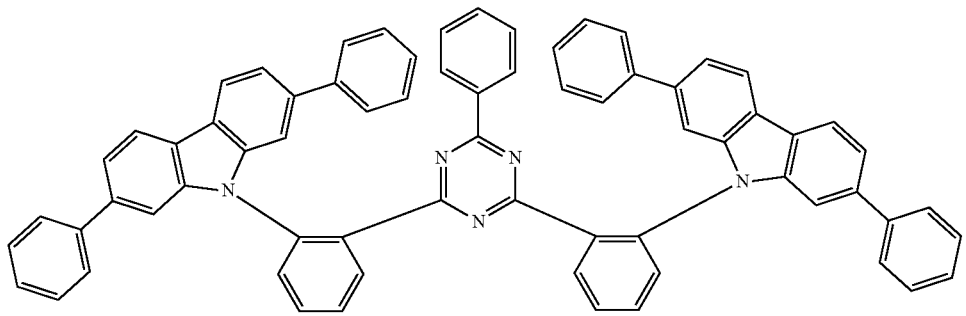
48
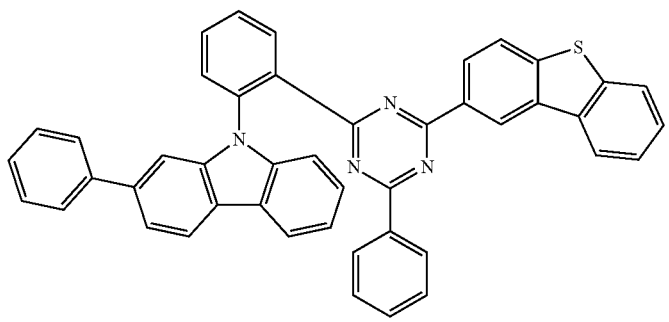
49
50
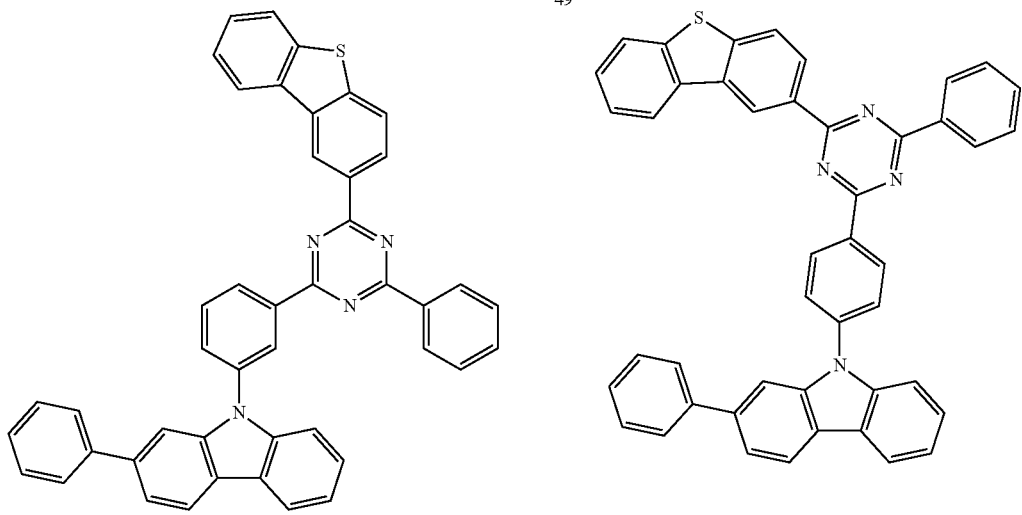
51
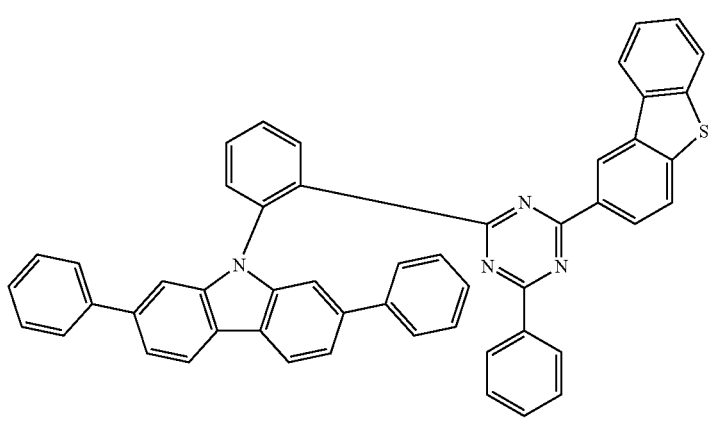

-continued
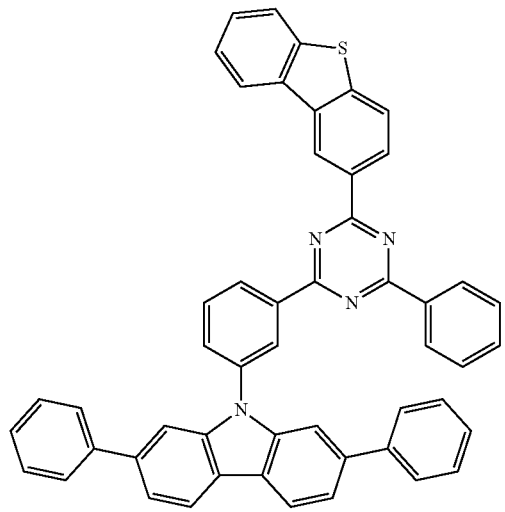
52
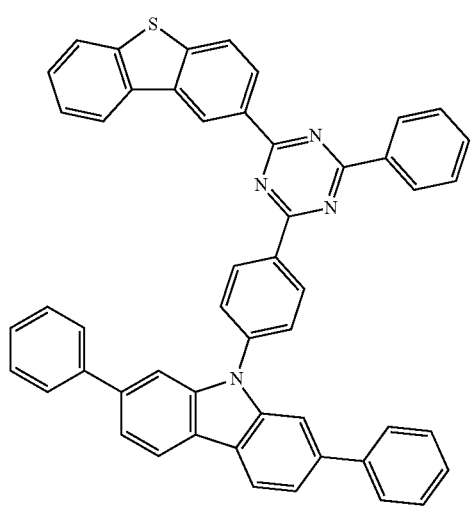
53
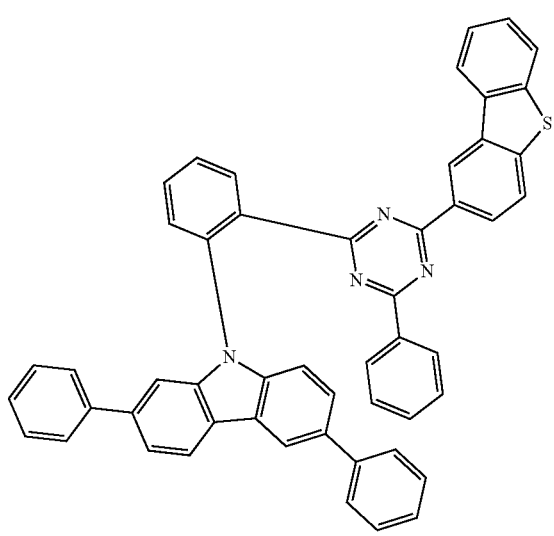
54

55 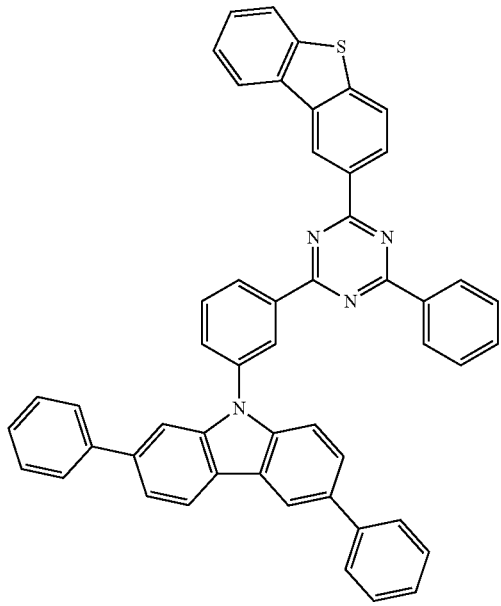
56 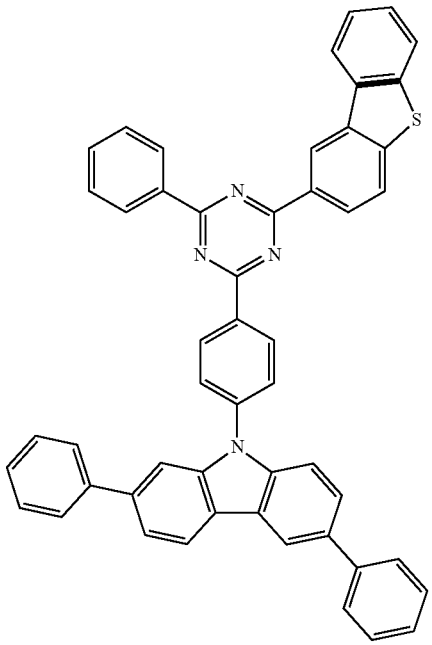
57 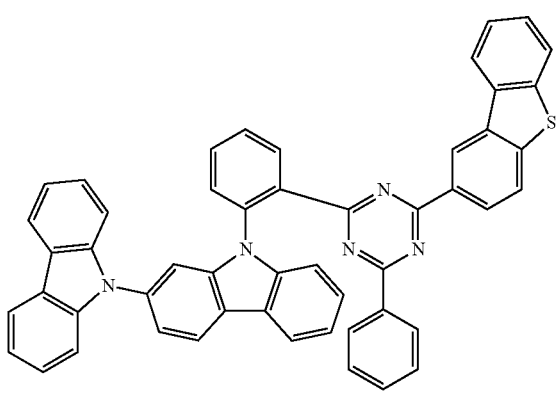
58 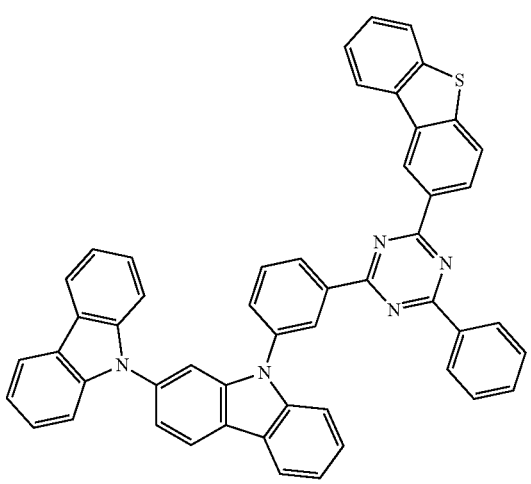
59 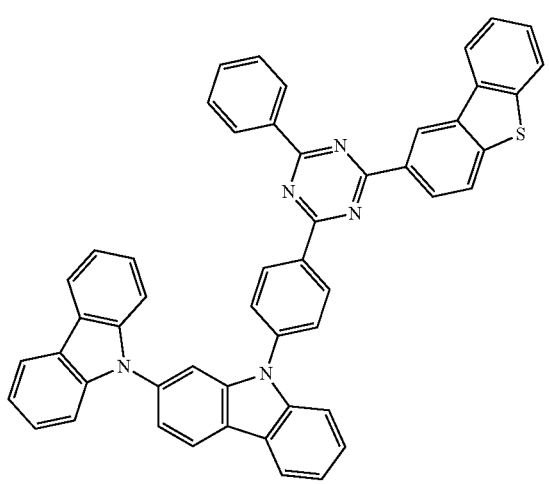
60 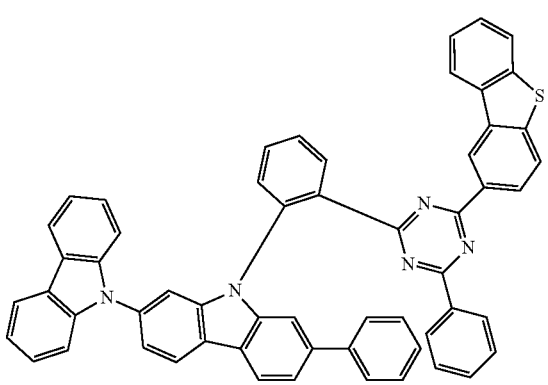

61
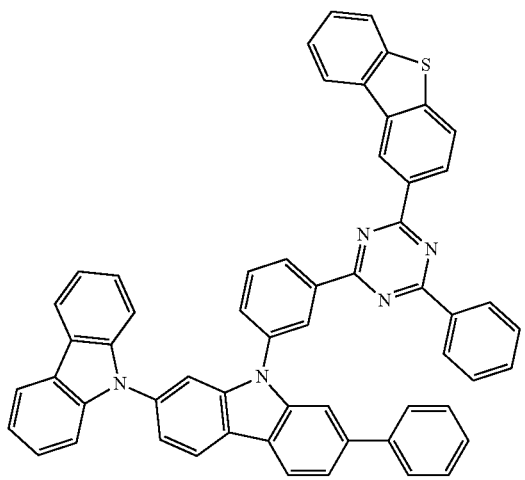
62
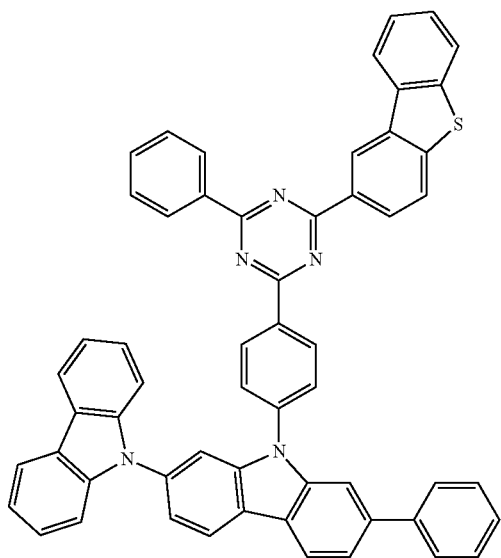
63
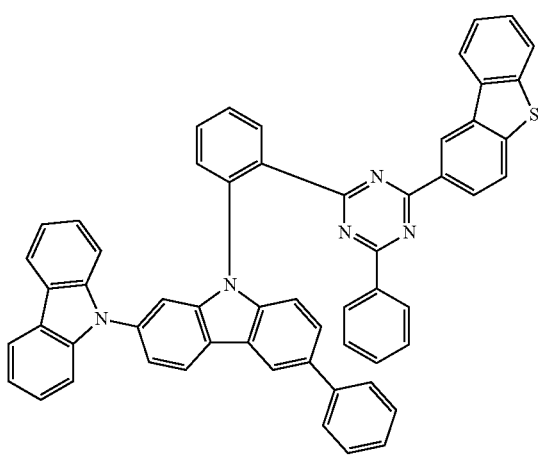
64
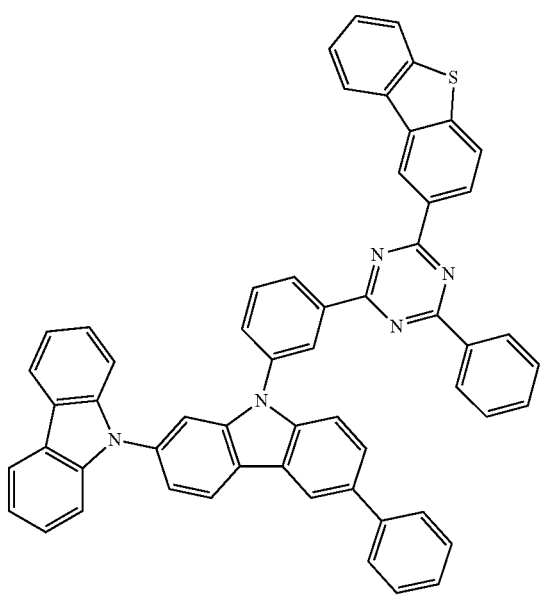

-continued
65
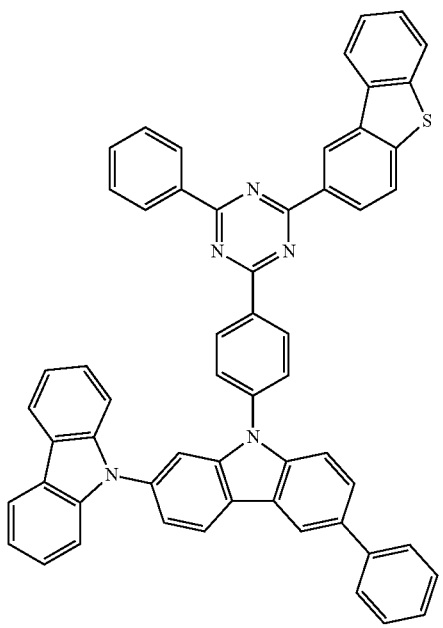
66
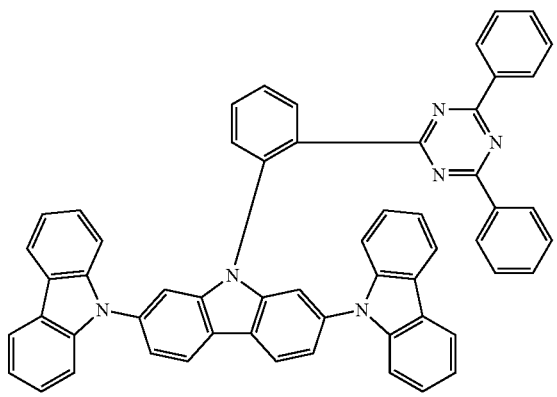
67
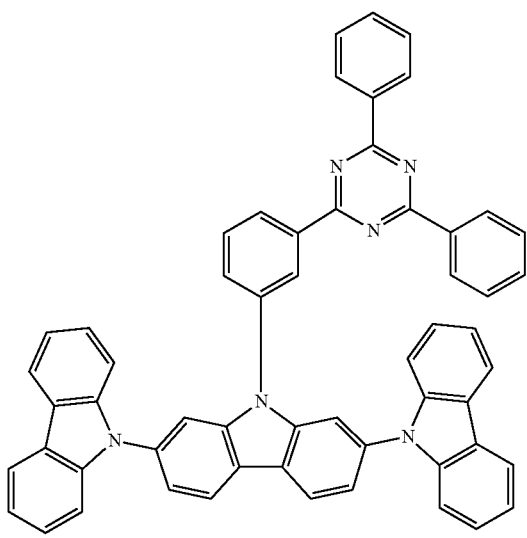
68
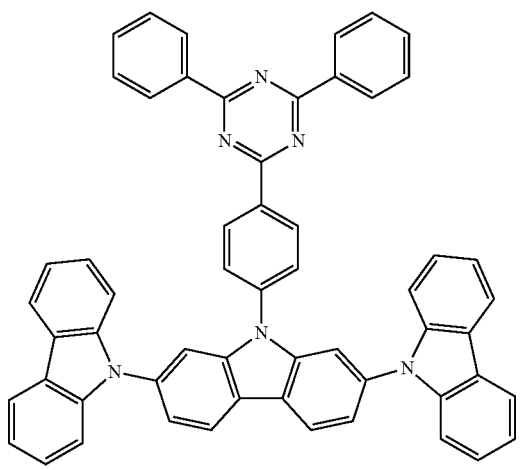
69
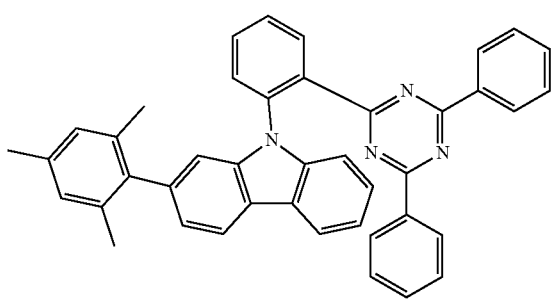
70
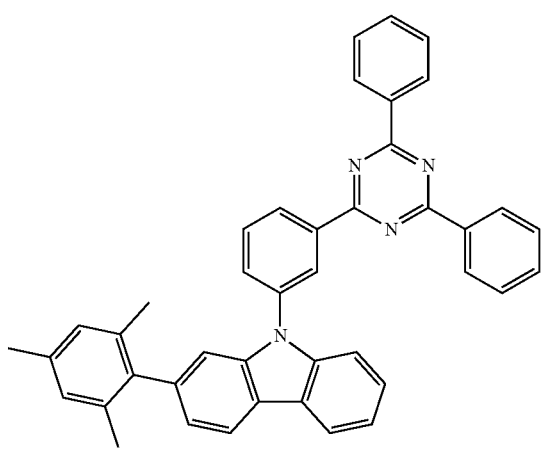

71
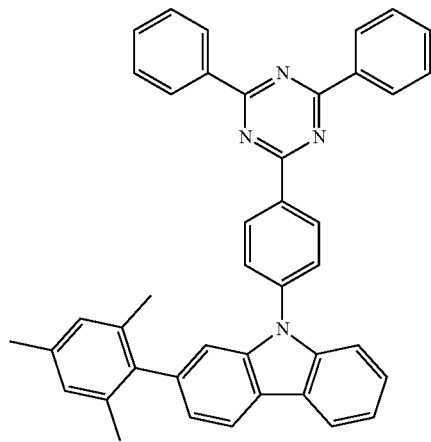
72
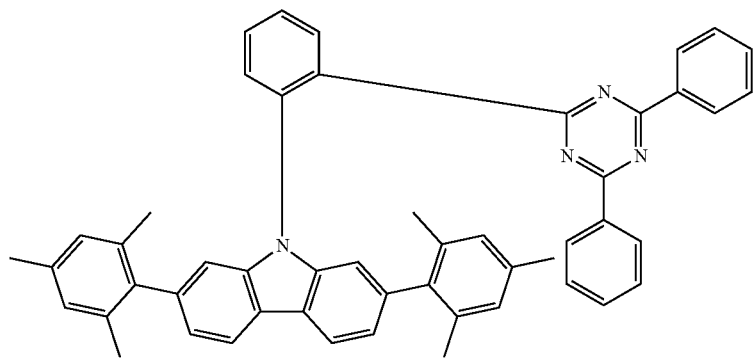
73
74
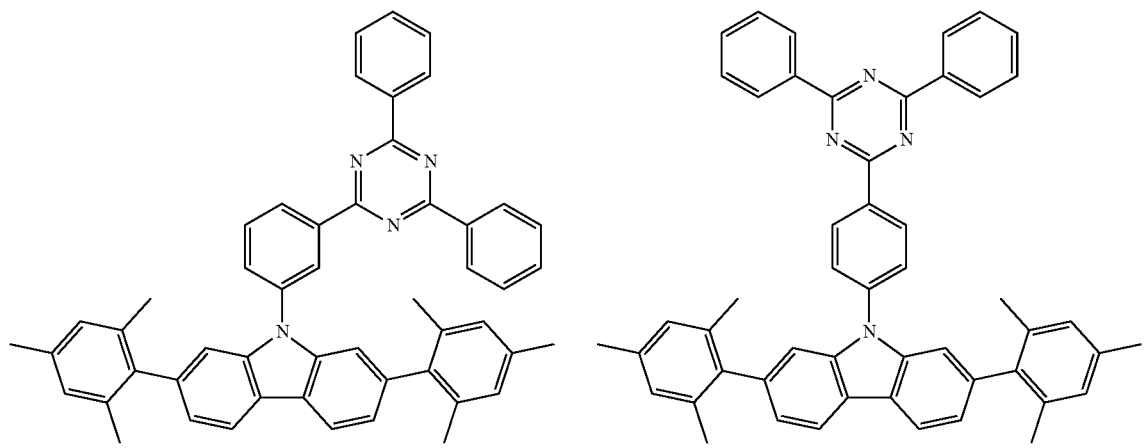

-continued
75
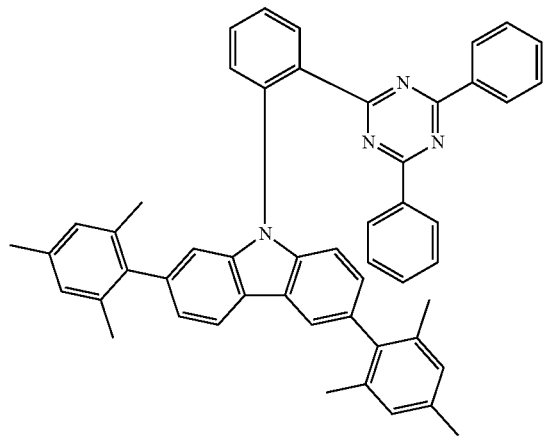
76
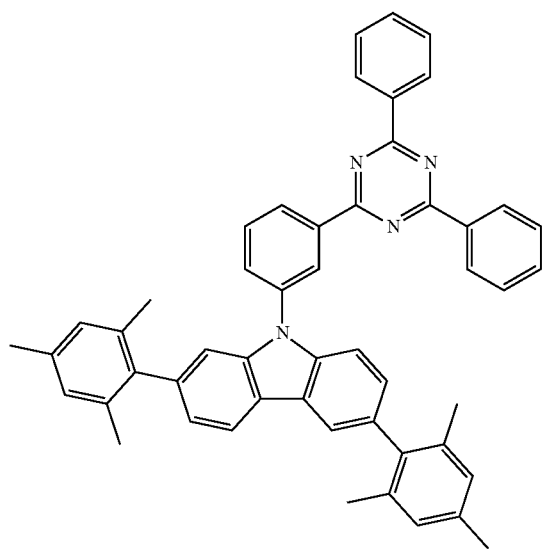
77
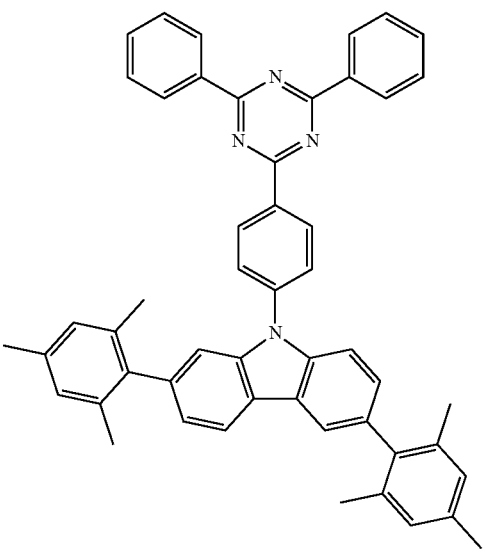
78
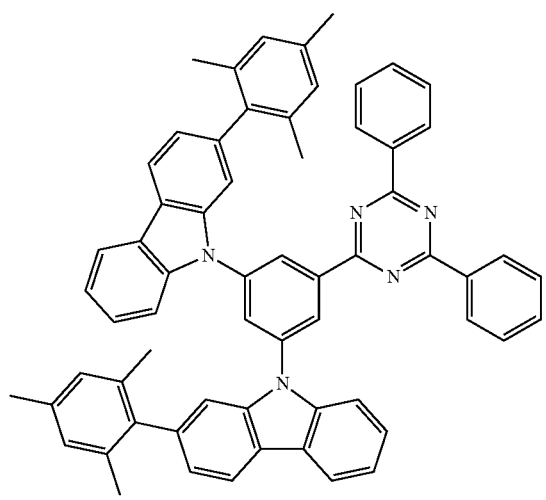
79
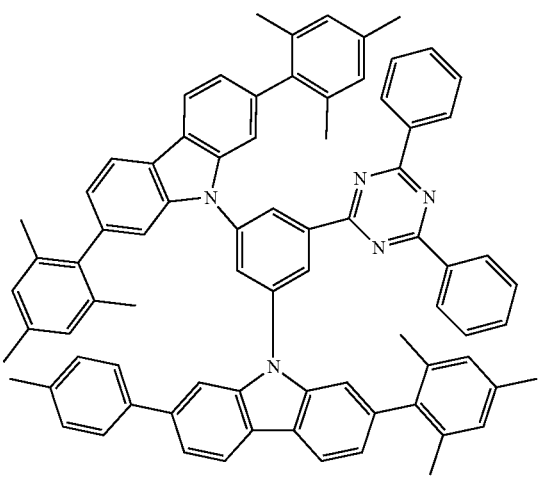

80
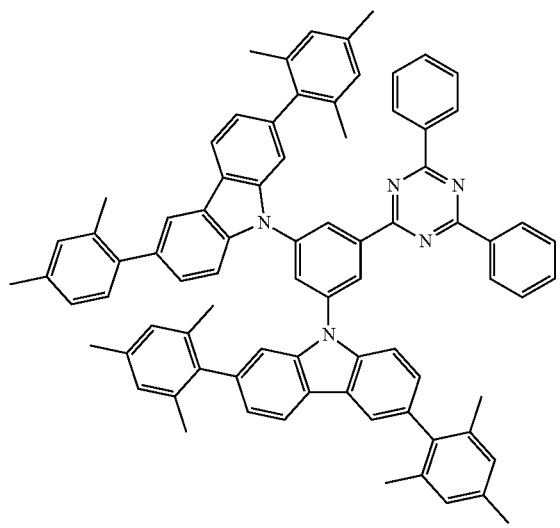
81
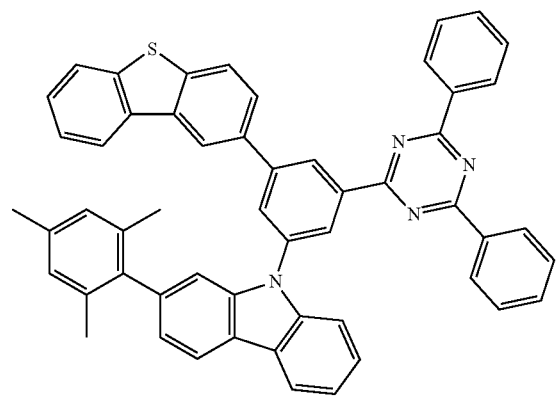
82
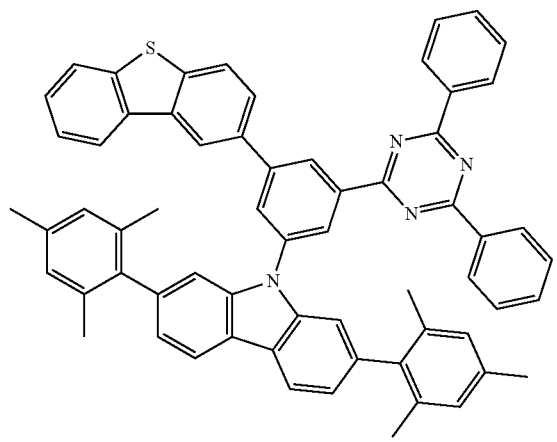
83
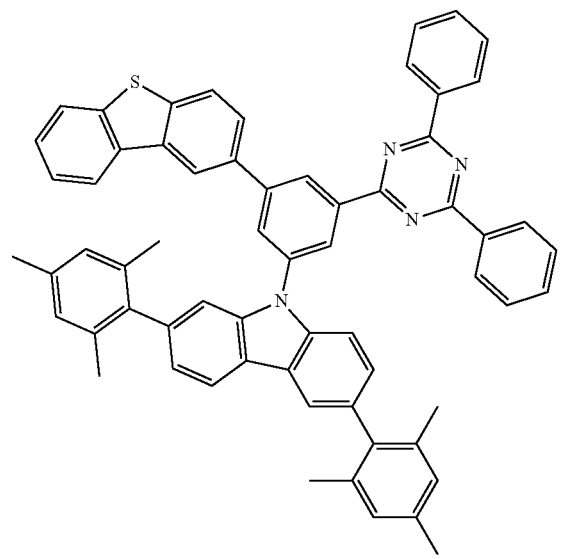

84

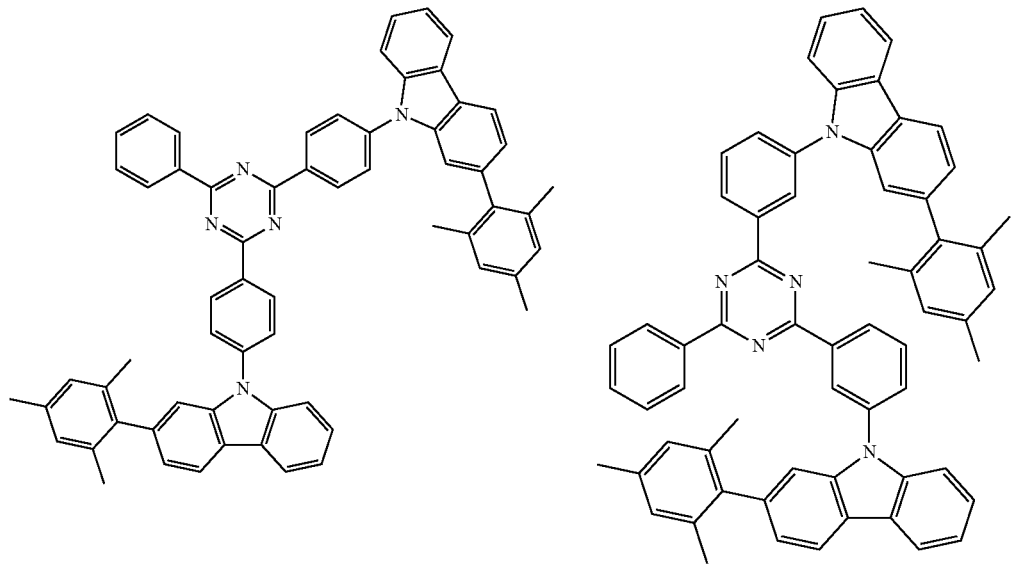

85

86

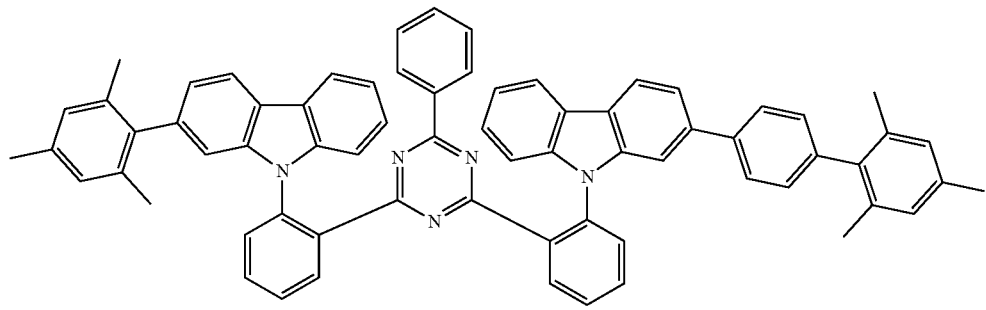

87

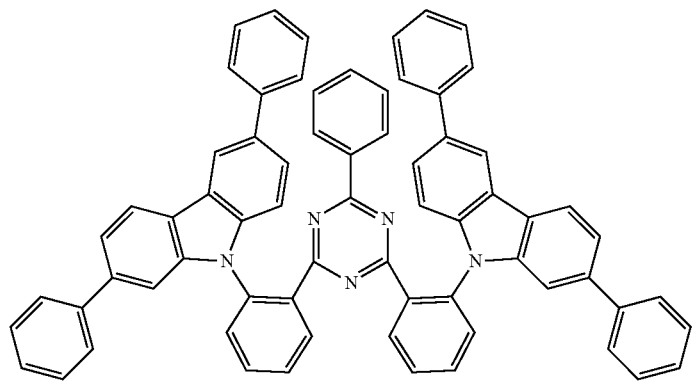

The emission layer EML may include one, two, or more different (kinds of) nitrogen-containing compounds. The emission layer EML may further include a suitable (e.g., known) material in addition to the nitrogen-containing compound.

The emission layer EML may include a host and a dopant, and the dopant may include a nitrogen-containing compound. The nitrogen-containing compound represented by Formula 1 may be included in the emission layer EML as a dopant. The nitrogen-containing compound represented by Formula 1 may be included in the emission layer EML as a dopant for thermally activated delayed fluorescence. The emission layer EML including the nitrogen-containing compound may emit blue light in a wavelength region having less than about 470 nm. For example, the nitrogen-containing compound may be included in the emission layer EML as a dopant emitting deep blue light having a wavelength region of about 440 nm to about 470 nm, or about 450 nm to about 470 nm.

The emission layer EML may include one or two kinds of hosts.

The emission layer EML may include a host and a dopant, and the host may include a nitrogen-containing compound.

The host material may include common materials (e.g., known in the art), without being limited thereto. For example, at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), or 1,3,5-tris(N-phenylbenzimidazole-2-yl)benzene (TPBi) may be included. However, an embodiment of the inventive concept is not limited thereto. For example, tris(8-hydroxyquinolino)aluminum ($Alq_3$), 4,4'-bis(N-carbazolyl)-1,1'-biphenyl (CBP), poly(N-vinylcarbazole) (PVK), 9,10-di(naphthalene-2-yl) anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino) phenyl]ether oxide (DPEPO), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), bis(3-chloro-2-hydroxypropyl)disulfide (BCPDS), (4-{1-[4-(diphenylphosphoryl)phenyl] cyclohexyl}phenyl)bis(4-methylphenyl)amine (POPCPA), etc., may be utilized as the host material.

For example, the emission layer EML may further include as a dopant, at least one of N,N,N',N'-tetraphenyl-pyrene-1,6-diamine (TPD), 4,4'-bis(2-(9-ethyl-9H-carbazol-3-yl)vinyl)-1,1'-biphenyl (BCzVBi); 4,4'-bis(9-ethyl-3-carbazovinylene)-1,1'-biphenyl, 10-phenyl-10H,10'H-spiro[acridine-9,9'-anthracene]-10'-one (ACRSA), 3,4,5,6-tetra-9H-carbazol-9-yl-1,2-benzenedicarbonitrile (4CzPN), 2,4,5,6-tetra-9H-carbazol-9-yl-isophthalonitrile (4CzIPN), bis[4-9,9-dimethyl-9,10-dihydroacridine]phenyl]sulfone (DMAC-DPS), and 2-phenoxazine-4,6-diphenyl-1,3,5-triazine (PSZ-TRZ). In addition, the emission layer EML may further include as known dopant materials, styryl derivatives (for example, 1,4-bis[2-(3-N-ethylcarbazoryl)vinyl]benzene (BCzVB), 4-(di-p-tolylamino)-4'-[(di-p-tolylamino)styryl] stilbene (DPAVB), and N-(4-((E)-2-(6-((E)-4-(diphenylamino)styryl)naphthalen-2-yl)vinyl)phenyl)-N-phenyl-benzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

The emission layer EML may be a blue emission layer which emits blue light. The emission layer EML may be a fluorescence emission layer radiating fluorescence. The emission layer EML may be a delayed fluorescence emission layer radiating delayed fluorescence.

The electron transport region ETR is provided on the emission layer EML. The electron transport region ETR may include at least one of a hole blocking layer HBL, an electron transport layer ETL, or an electron injection layer EIL, without being limited thereto.

The electron transport region ETR may have a single layer formed utilizing a single material, a single layer formed utilizing a plurality of different materials, or a multilayer structure having a plurality of layers formed utilizing a plurality of different materials.

For example, the electron transport region ETR may have a single layer structure of an electron injection layer EIL or an electron transport layer ETL, or a single layer structure formed utilizing a plurality of different materials, such as an electron injection material and an electron transport material. Further, the electron transport region ETR may have a structure laminated from the emission layer EML of electron transport layer ETL/electron injection layer EIL, or hole blocking layer HBL/electron transport layer ETL/electron injection layer EIL, without being limited thereto. The thickness of the electron transport region ETR may be, for example, from about 1,000 Å to about 1,500 Å.

The electron transport region ETR may be formed utilizing various suitable methods, such as a vacuum deposition method, a spin coating method, a cast method, a Langmuir-Blodgett (LB) method, an inkjet printing method, a laser printing method, and a laser induced thermal imaging (LITI) method.

If the electron transport region ETR includes an electron transport layer ETL, the electron transport region ETR may include an anthracene-based compound. However, an embodiment of the inventive concept is not limited thereto. The electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), berylliumbis(benzoquinolin-10-olate ($Bebq_2$), 9,10-di(naphthalene-2-yl) anthracene (ADN), or a mixture thereof. The thickness of the electron transport layers ETL may be from about 100 Å to about 1,000 Å, for example, from about 150 Å to about 500 Å. If the thickness of the electron transport layer ETL satisfies the above-described range, satisfactory electron transport properties may be obtained without a substantial increase of a driving voltage.

If the electron transport region ETR includes an electron injection layer EIL, the electron transport region ETR may utilize LiF, lithium quinolate (LiQ), $Li_2O$, BaO, NaCl, CsF, a metal in lanthanoides (such as Yb), and/or a metal halide (such as RbCl, and RbI). However, an embodiment of the inventive concept is not limited thereto. The electron injection layer EIL may also be formed utilizing a mixture material of an electron transport material and an insulating organo metal salt. The organo metal salt may be a material having an energy band gap of about 4 eV or more. In one embodiment, the organo metal salt may include, for example, metal acetates, metal benzoates, metal acetoacetates, metal acetylacetonates, or metal stearates. The thickness of the electron injection layer EIL may be from about 1 Å to about 100 Å, or from about 3 Å to about 90 Å. If the thickness of the electron injection layer EIL satisfies the above-described ranges, satisfactory electron injection properties may be obtained without a substantial increase of a driving voltage.

The electron transport region ETR may include a hole blocking layer HBL as described above. The hole blocking layer HBL may include, for example, diphenylphosphine oxide-4(triphenylsilyl)phenyl (TSPO1), 2,9-dimethyl-4,7-diphenyl-1,10-phenanthroline (BCP), and/or 4,7-diphenyl- 1,10-phenanthroline (Bphen). However, an embodiment of the inventive concept is not limited thereto.

The second electrode EL2 is provided on the electron transport region ETR. The second electrode EL2 may be a common electrode or a cathode. The second electrode EL2 may be a transmissive electrode, a transflective electrode or a reflective electrode. If the second electrode EL2 is the transmissive electrode, the second electrode EL2 may include a transparent metal oxide, for example, ITO, IZO, ZnO, ITZO, etc.

If the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound including thereof, or a mixture thereof (for example, a mixture of Ag and Mg). The second electrode EL2 may have a multilayered structure including a reflective layer or a transflective layer formed utilizing the above-described materials and a transparent conductive layer formed utilizing ITO, IZO, ZnO, ITZO, etc.

In one embodiment, the second electrode EL2 may be connected with an auxiliary electrode. If the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to produce excitons, and the excitons may emit light when transitioned from an excited state to a ground state.

The organic electroluminescence device 10 according to an embodiment of the inventive concept includes a nitrogen-containing compound as a material for an emission layer and has excellent efficiency.

An embodiment of the inventive concept provides a nitrogen-containing compound represented by Formula 1. The nitrogen-containing compound may be utilized as a material for an organic electroluminescence device.

Particular explanation on the nitrogen-containing compound according to an embodiment of the inventive concept is the same as described above, and will not be repeated. For example, the nitrogen-containing compound according to an embodiment of the inventive concept may be any one selected from the compounds represented in Compound Group 1.

The nitrogen-containing compound according to an embodiment of the inventive concept may have a difference between a singlet energy level and a triplet energy level of about 0.2 eV or less, and as a result, may be utilized as a material for thermally activated delayed fluorescence. The nitrogen-containing compound according to an embodiment of the inventive concept may be applied as a material for an organic electroluminescence device to contribute to the improvement of efficiency.

Because the nitrogen-containing compound according to an embodiment of the inventive concept contains one or more substituents such as a phenyl group and a carbazole group in at least one position of 2, 3 or 7 of carbazole, the delocalization of the carbazole group where HOMO is positioned is expanded, and HOMO stabilization is achieved. As a result, a HOMO energy level may be lowered, the increase of a difference ($E_{ST}$) between a singlet energy level and a triplet energy level may be restrained (e.g., maximally restrained), and the singlet energy level may be elevated. According to the increase of the singlet energy level, emission wavelength may be blue shifted, and may be shifted to deeper blue color when compared to comparable carbazole compounds, thereby favorably accomplishing blue thermally activated delayed fluorescence. This phenomenon is compared to the red shift of the emission wavelength of a structure in which positions 3 and 6 of a carbazole group are substituted.

In addition, because a substituent is positioned in the carbazole group, which is an electron donor, the nitrogen-containing compound according to an embodiment of the inventive concept has an increased intramolecular steric hindrance, and restraining effects of the vibrations of a molecule may be achieved (e.g., anticipated). Generally, thermally activated delayed fluorescence tend to show broader light emission, which has a bell-shaped distribution spectrum when compared to common fluorescence or phosphorescence emission, because of the light emitted from the charge-transfer (CT) of various geometries on the basis of the CT emission properties. However, one or more substituents are positioned in at least one of positions 2, 3 or 7 of a carbazole group in the nitrogen-containing compound according to an embodiment of the inventive concept. The substituent plays the role of a rotation inhibitor, and accordingly, the effect of decreased number of geometry cases which participate in CT emission may be realized (e.g., anticipated). Due to this, emission half width may decrease. That is, the nitrogen-containing compound according to an embodiment of the inventive concept includes a rotation inhibitor in carbazole itself in which HOMO is positioned, and the emission half width may be decreased and the tendency of red shift may be restrained.

Hereinafter, the inventive concept will be explained in more detail with reference to particular embodiments and comparative embodiments. The following embodiments are only illustrations to assist the understanding of the inventive concept, and the scope of the inventive concept is not limited thereto.

Synthetic Examples

The nitrogen-containing compounds according to exemplary embodiments of the inventive concept may be synthesized as follows. However, an embodiment of the synthetic method of the nitrogen-containing compound according to exemplary embodiments of the inventive concept is not limited thereto.

1. Synthesis of Compound 4

Compound 4 according to an embodiment of the inventive concept may be synthesized, for example, as follows.

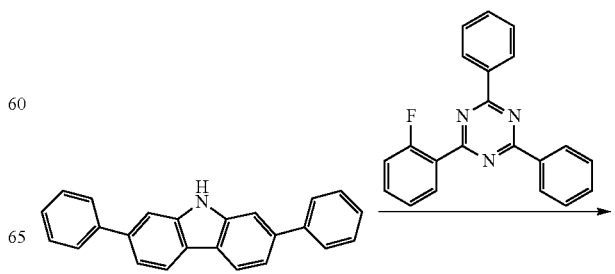

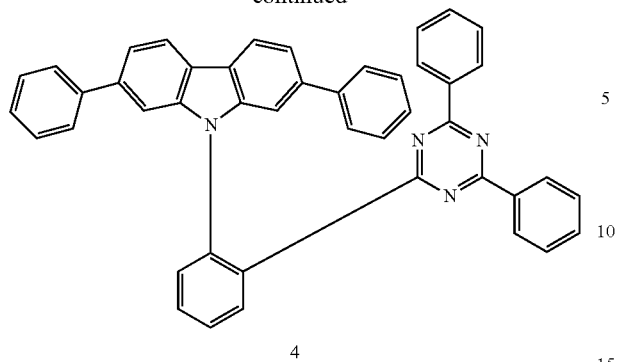

4

2,7-diphenyl-9H-carbazole (1 eq), 2-(2-fluorophenyl)-4,6-diphenyl-1,3,5-triazine (1 eq), and $K_3PO_4$ (2 eq) were dissolved in DMF and stirred at about 160 degrees Celsius for about 12 hours. After cooling, an aqueous NaCl solution was poured thereto to quench the reaction, followed by stirring for about 30 minutes. The precipitate thus obtained was filtered, and the solid thus obtained was extracted with distilled water and DCM, dried with $MgSO_4$, and dried under a reduced pressure. The organic layer thus obtained was separated by column chromatography (MC/Hex) to produce Compound 4 (yield: 55%).

$C_{45}H_{30}N_4$: M+1 626.74

2. Synthesis of Compound 22

Compound 22 according to an embodiment of the inventive concept may be synthesized, for example, as follows.

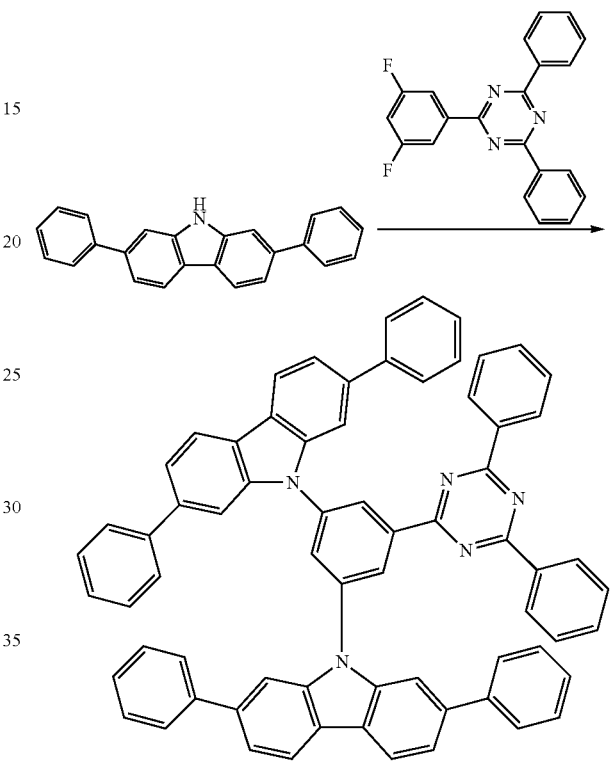

22

Compound 22 was produced by conducting the same synthetic method of Compound 4 except for utilizing 2-phenyl-9H-carbazole (2 eq) instead of 2,7-diphenyl-9H-carbazole (1 eq) and utilizing 2-(3,5-difluorophenyl)-4,6-diphenyl-1,3,5-triazine (1 eq) instead of 2-(2-fluorophenyl)-4,6-diphenyl-1,3,5-triazine (1 eq) (yield: 63%).

$C_{57}H_{37}N_5$: M+1 791.93

3. Synthesis of Compound 23

Compound 23 according to an embodiment of the inventive concept may be synthesized, for example, as follows.

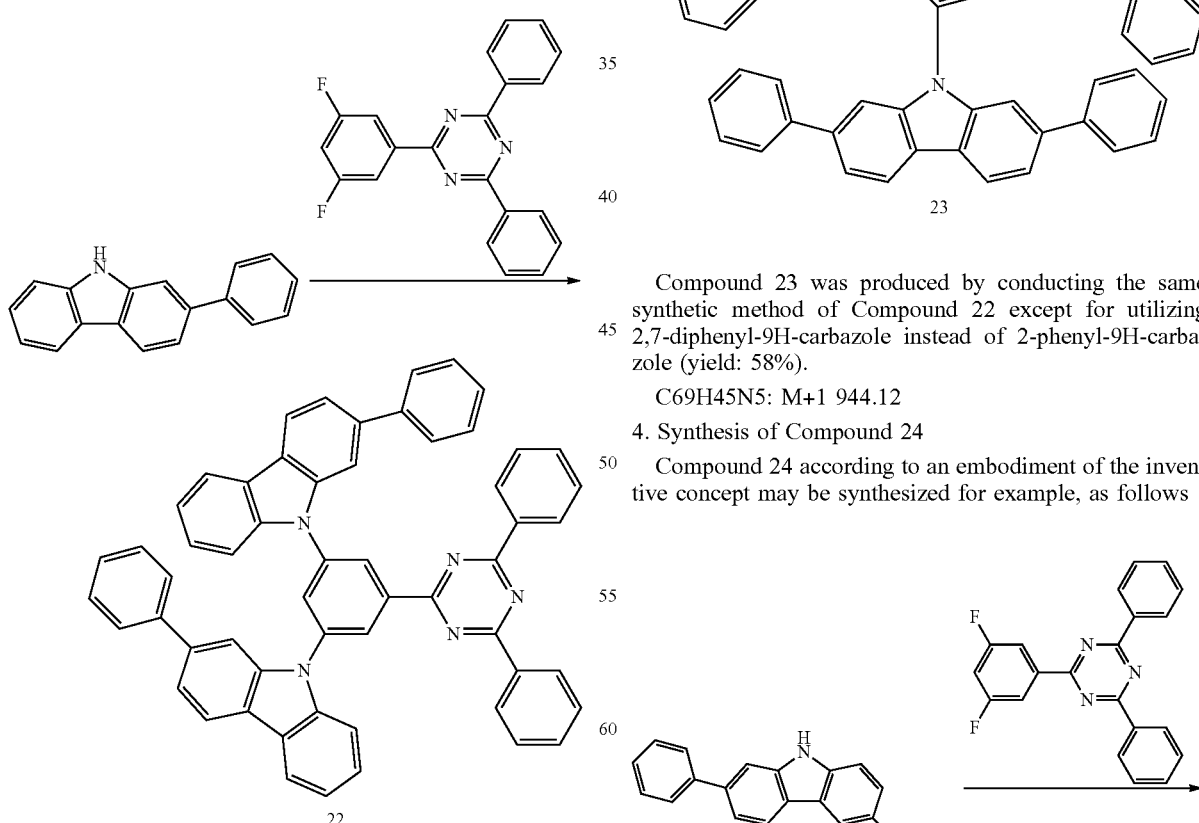

23

Compound 23 was produced by conducting the same synthetic method of Compound 22 except for utilizing 2,7-diphenyl-9H-carbazole instead of 2-phenyl-9H-carbazole (yield: 58%).

$C_{69}H_{45}N_5$: M+1 944.12

4. Synthesis of Compound 24

Compound 24 according to an embodiment of the inventive concept may be synthesized for example, as follows

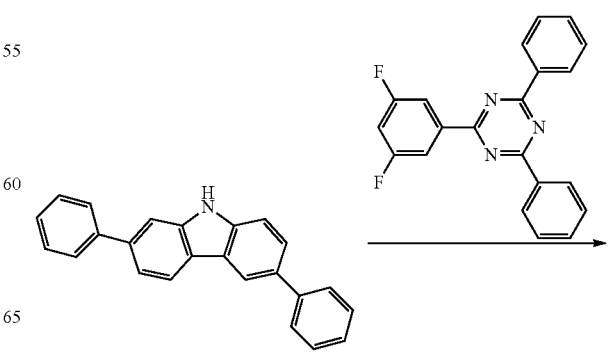

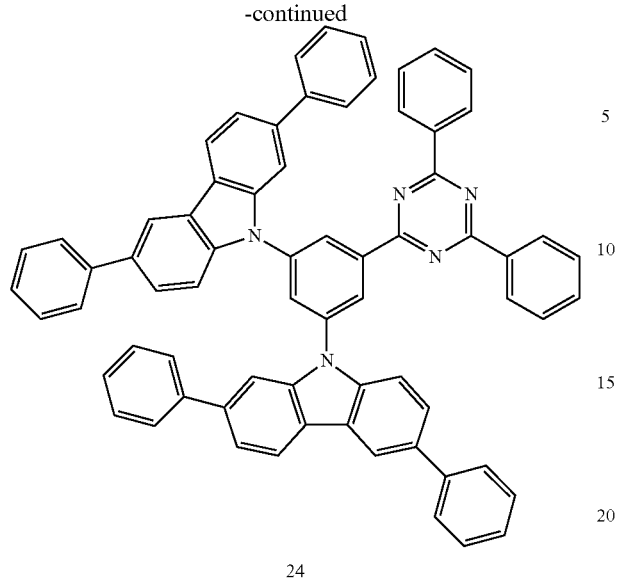
24
Compound 24 was produced by conducting the same synthetic method of Compound 22 except for utilizing 2,6-diphenyl-9H-carbazole instead of 2-phenyl-9H-carbazole (yield: 40%).
$C_{69}H_{45}N_5$: M+1 944.11
5. Synthesis of Compound 29
Compound 29 according to an embodiment of the inventive concept may be synthesized, for example, as follows.
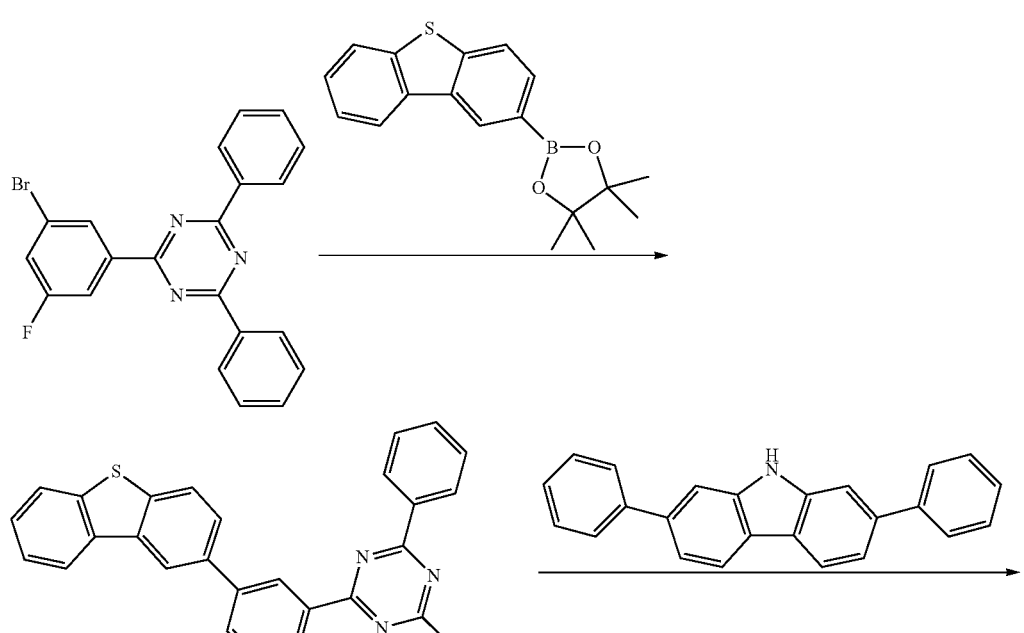
29-1

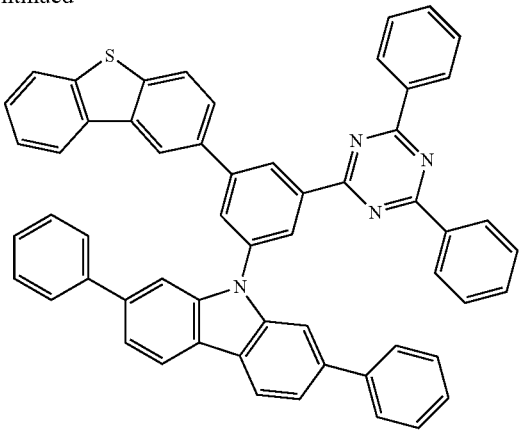

29

Synthesis of Intermediate 29-1

2-(3-bromo-5-fluorophenyl)-4,6-diphenyl-1,3,5-triazine (1 eq), 2-(dibenzo[b,d]thiophen-2-yl)-4,4,5,5-tetramethyl-1,3,2-dioxaborolane (1 eq), Pd(PPh3)4 (5 mol %), and 4.15 g (3 eq) of K₂CO₃ were dissolved in a mixture solution of THF/H2O (2:1) and stirred at about 80° C. for about 16 hours. After cooling to room temperature, the reaction solution was extracted utilizing water and diethyl ether three times. The organic layer thus obtained was dried with magnesium sulfate and the solvents were evaporated. The residue thus obtained was separated by silica gel column chromatography to produce Intermediate 29-1 (yield: 80%).

Synthesis of Compound 29

Compound 29 was produced by conducting the same synthetic method of Compound 4 except for utilizing Intermediate 29-1 instead of 2-(2-fluorophenyl)-4,6-diphenyl-1,3,5-triazine (yield: 60%).

C57H36N4S: M+1 808.98

6. Synthesis of Compound 47

Compound 47 according to an embodiment of the inventive concept may be synthesized, for example, as follows.

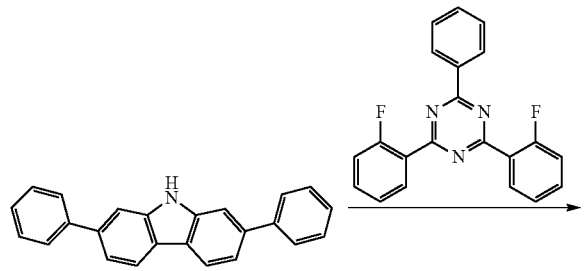

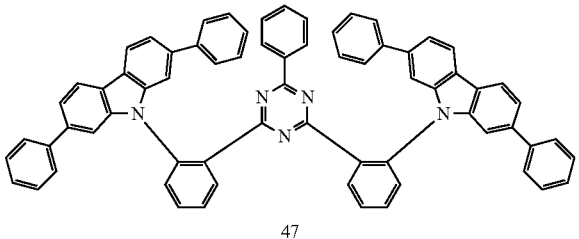

47

Compound 47 was produced by conducting the same synthetic method of Compound 22 except for utilizing 2,7-diphenyl-9H-carbazole instead of 2-phenyl-9H-carbazole and utilizing 2,4-bis(2-fluorophenyl)-6-phenyl-1,3,5-triazine instead of 2-(3,5-difluorophenyl)-4,6-diphenyl-1,3,5-triazine (yield: 35%).

C69H45N5: M+1 944.12

7. Synthesis of Compound 51

Compound 51 according to an embodiment of the inventive concept may be synthesized, for example, as follows.

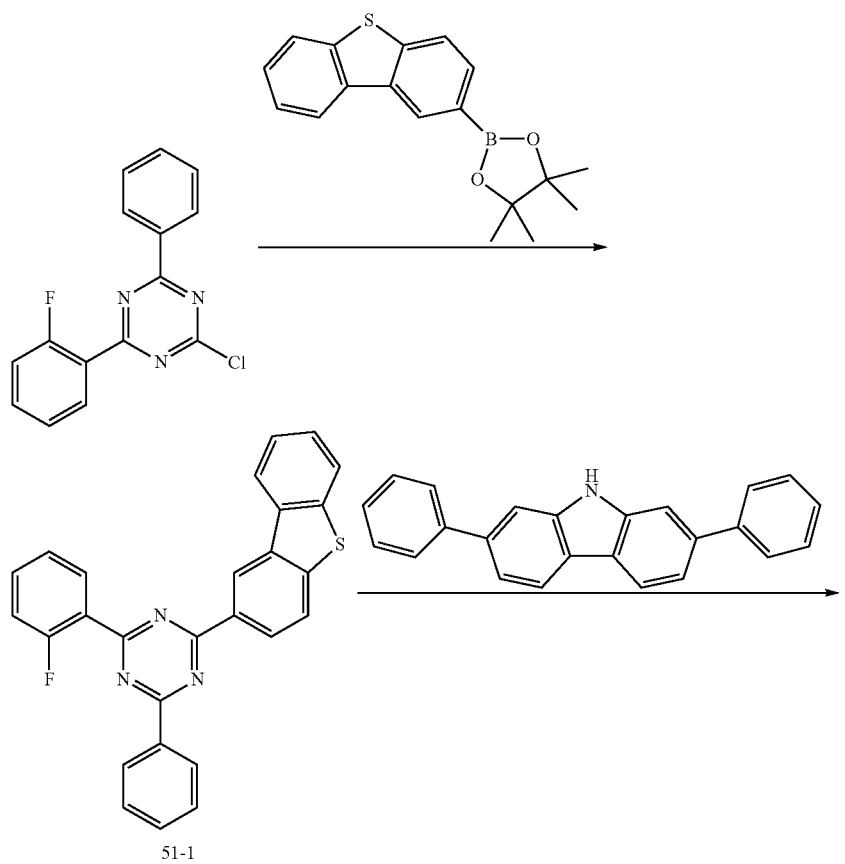

Synthesis of Intermediate 51-1

Intermediate 51-1 was produced by conducting the same synthetic method of Intermediate 29-1 except for utilizing 2-chloro-4-(2-fluorophenyl)-6-phenyl-1,3,5-triazine instead of 2-(3-bromo-5-fluorophenyl)-4,6-diphenyl-1,3,5-triazine (yield: 55%).

Synthesis of Compound 51

Compound 51 was produced by conducting the same synthetic method of Compound 4 except for utilizing Intermediate 51-1 instead of 2-(2-fluorophenyl)-4,6-diphenyl-1,3,5-triazine (yield: 57%).

C51H32N4S M+1 732.88

8. Synthesis of Compound 72

Compound 72 according to an embodiment of the inventive concept may be synthesized, for example, as follows.

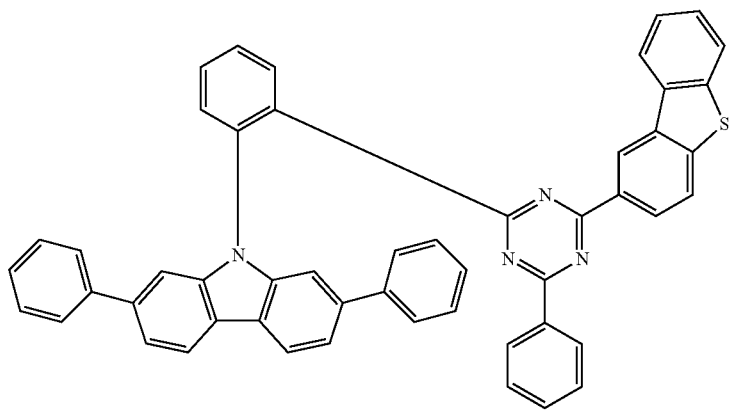

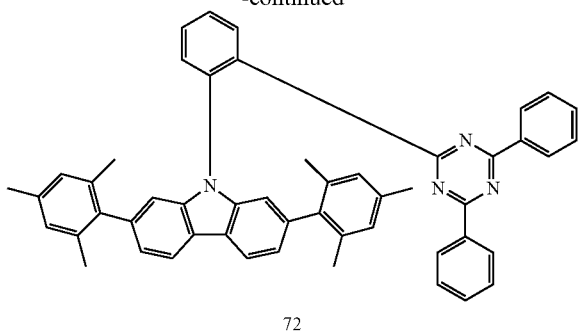

72

Compound 72 was produced by conducting the same synthetic method of Compound 4 except for utilizing 2,7-dimesityl-9H-carbazole instead of 2,7-diphenyl-9H-carbazole (yield: 52%).

C51H42N4: M+1 710.90

9. Synthesis of Compound 83

Compound 83 according to an embodiment of the inventive concept may be synthesized, for example, as follows.

Compound 83 was produced by conducting the same synthetic method of Compound 29 except for utilizing 2,6-dimesityl-9H-carbazole instead of 2,7-diphenyl-9H-carbazole (yield: 45%).

C63H48N4S: M+1 893.14

10. Synthesis of Compound 87

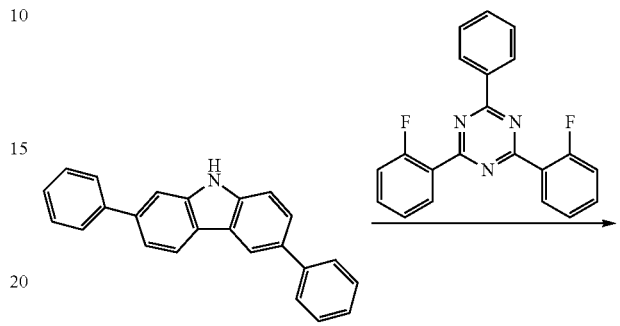

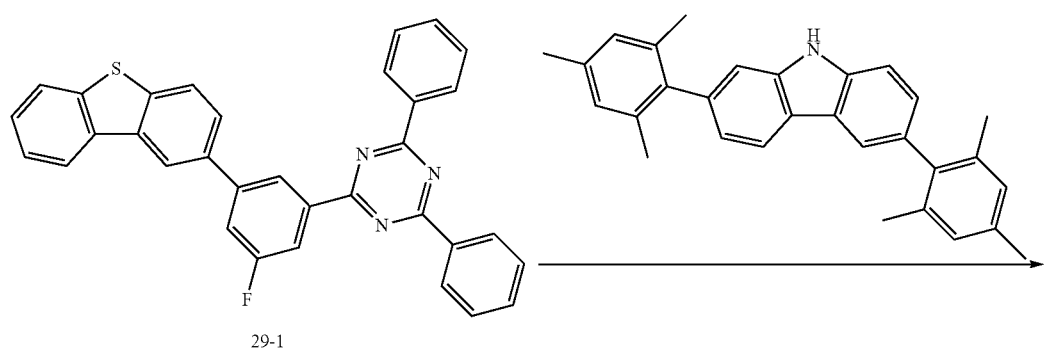

29-1

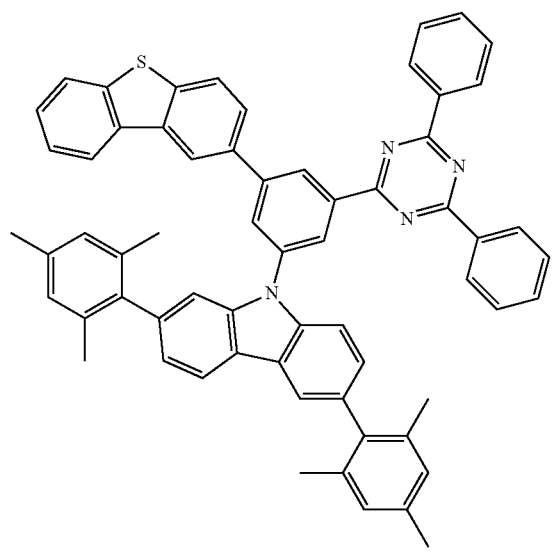

83

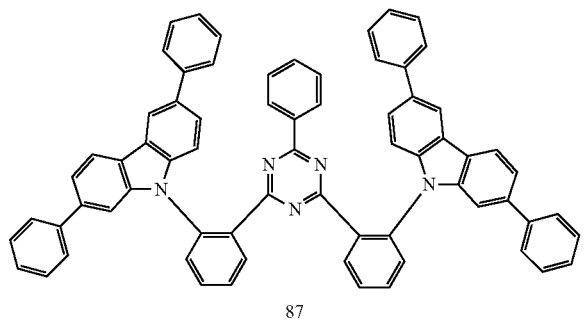

87

Compound 87 was produced by conducting the same synthetic method of Compound 47 except for utilizing 2,6-diphenyl-9H-carbazole instead of 2,7-diphenyl-9H-carbazole (yield: 46%).

C69H45N5: M+1 944.12

The above-described synthetic examples are illustrations only, and reaction conditions may be changed as necessary. In addition, the compounds according to exemplary embodiments of the inventive concept may be synthesized so as to include various suitable substituents by utilizing methods and materials known in the art. By introducing various suitable substituents, properties appropriate (or desirable) for applying to an organic electroluminescence device may be attained.

NMR and molecular weight analysis data of Compounds 4, 22, 23, 24, 29, 47, 51, 72, 83 and 87 in the synthetic examples are shown in Table 1 below.

TABLE 1

| | NMR (δ) | Molecular weight (MS) | |
| --- | --- | --- | --- |
| | | Calculated | Measured |
| Compound 4 | 9.05-9.02 (2H, m), 8.68-8.58 (3H, m), 8.43-8.30 (5H, m), 8.22-8.16 (2H, m), 8.14-8.10 (1H, m), 8.01-7.85 (7H, m), 7.77-7.61 (10H, m) | 626.75 | 626.74 |
| Compound 22 | 8.49-8.40 (6H, m), 8.35-8.28 (6H, m), 8.16-8.07 (5H, m), 7.93-7.51 (20H, m) | 791.94 | 791.93 |
| Compound 23 | 8.64-8.55 (8H, m), 8.40-8.30 (6H, m), 8.22-8.14 (5H, m), 7.86-7.99 (14H, m), 7.59-7.73 (12H, m) | 944.13 | 944.12 |
| Compound 24 | 9.01-8.95 (2H, m), 8.63-8.55 (6H, m), 8.50-8.40 (6H, m), 8.26-8.07 (5H, m), 7.86-8.05 (14H, m), 7.59-7.73 (12H, m) | 944.13 | 944.11 |
| Compound 29 | 9.15-9.13 (1H, m), 8.84-8.69 (5H, m), 8.65-8.55 (3H, m), 8.41-8.35 (4H, m), 8.24-8.18 (4H, m), 8.08-7.77 (13H, m), 7.75-7.60 (6H, m) | 808.99 | 808.98 |
| Compound 47 | 8.74-8.70 (4H, m), 8.67-8.60 (8H, m), 8.45-8.29 (8H, m), 8.21-8.15 (2H, m), 8.07-7.89 (11H, m), 7.83-7.65 (12H, m) | 944.13 | 944.12 |
| Compound 51 | 8.94-8.88 (2H, m), 8.77-8.71 (2H, m), 8.62-8.54 (2H, m), 8.46-8.37 (6H, m), 8.10-7.77 (14H, m), 7.63-7.50 (6H, m) | 732.89 | 732.88 |
| Compound 72 | 8.68-8.65 (1H, m), 8.35-8.23 (7H, m), 8.08-7.94 (4H, m), 7.58-7.78 (7H, m), 7.46-7.43(1H, m), 6.99-6.95 (4H, m), 2.19-2.20 (18H, m) | 710.91 | 710.90 |
| Compound 83 | 9.02-8.90 (3H, m), 8.67-8.50 (5H, m), 8.45-8.36 (2H, m), 8.28-8.22 (4H, m), 8.11-8.03 (3H, m), 7.95 -7.78(5H, m), 7.70-7.62 (4H, m), 6.98-6.99 (4H, m), 2.16-2.08 (18H, m) | 893.15 | 893.14 |
| Compound 87 | 8.96-8.91 (2H, m), 8.75-8.61 (4H, m), 8.55-8.47 (4H, m), 8.42-8.32 (8H, m), 8.10-8.07 (2H, m), 7.77-8.02 (13H, m), 7.56-7.73 (12H, m) | 944.13 | 944.12 |

Device Manufacturing Examples

Organic electroluminescence devices of Examples 1 to 10 were manufactured utilizing Compounds 4, 22, 23, 24, 29, 47, 51, 72, 83 and 87 respectively as dopant materials of an emission layer.

Example Compounds

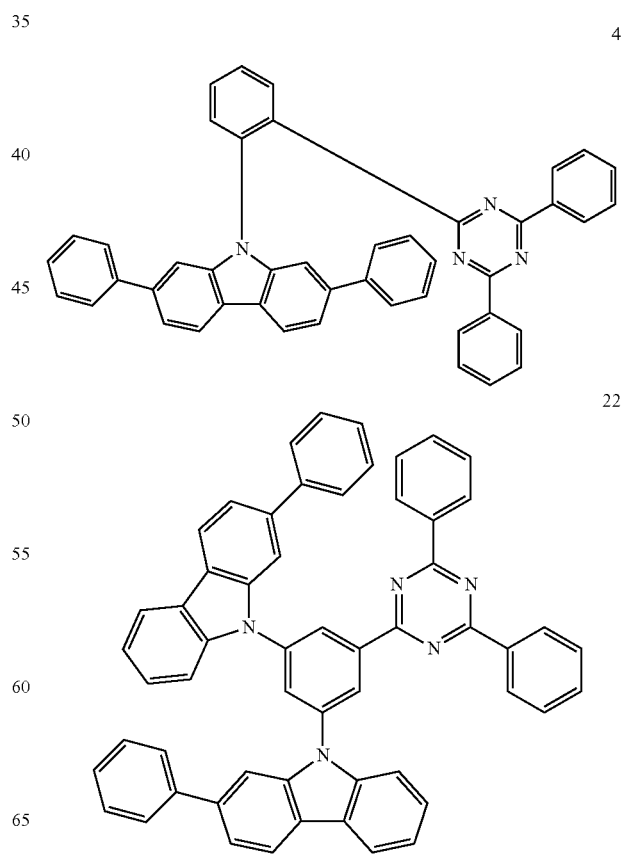

23
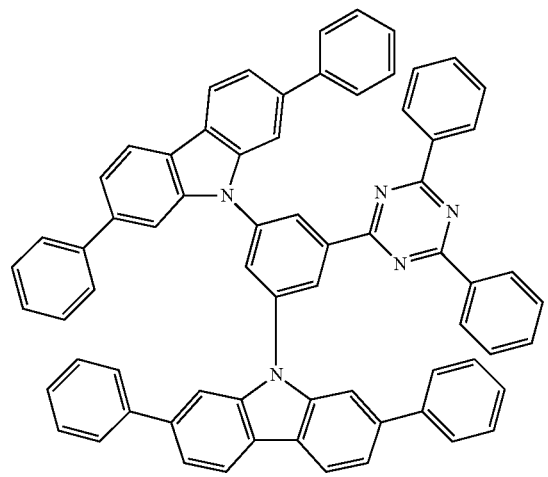
24
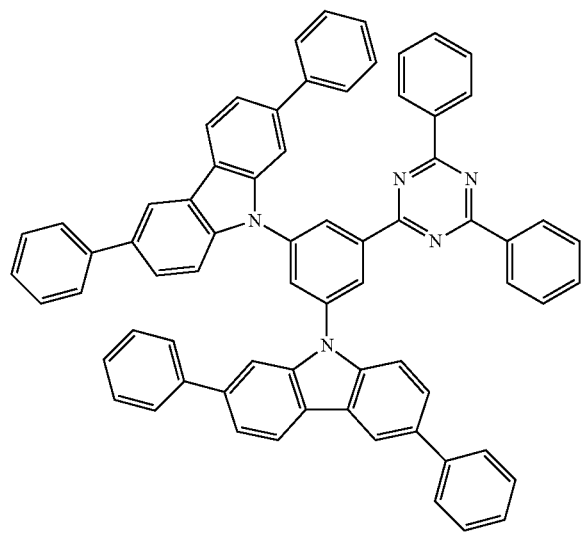
29
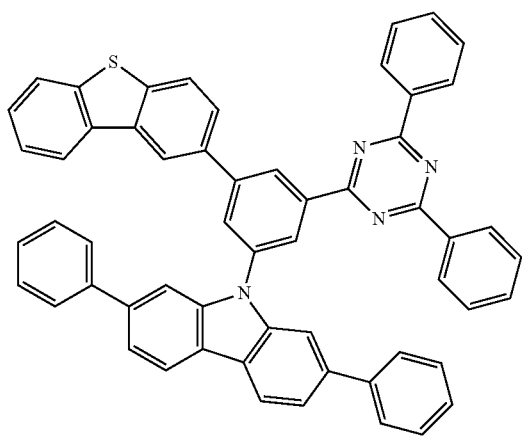
47
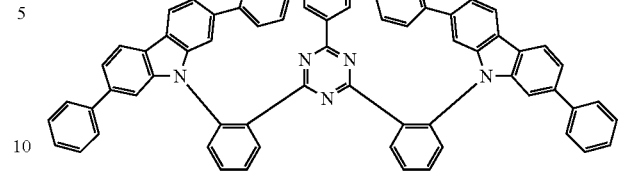
51
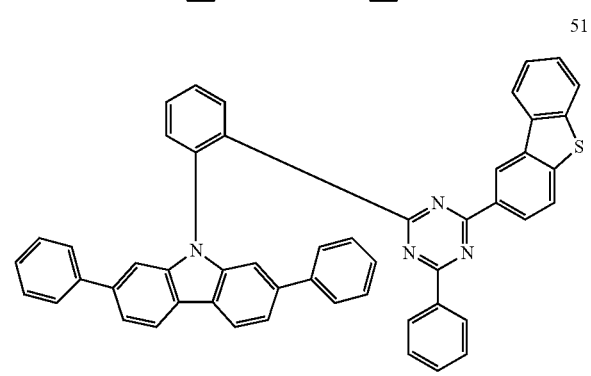
72
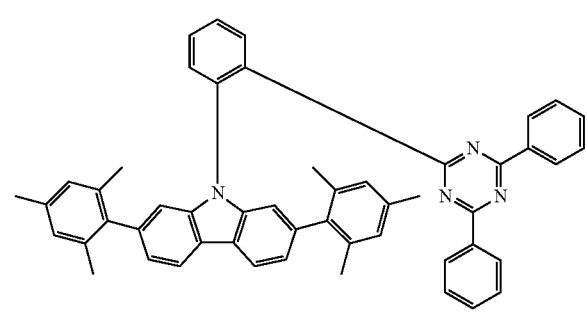
83
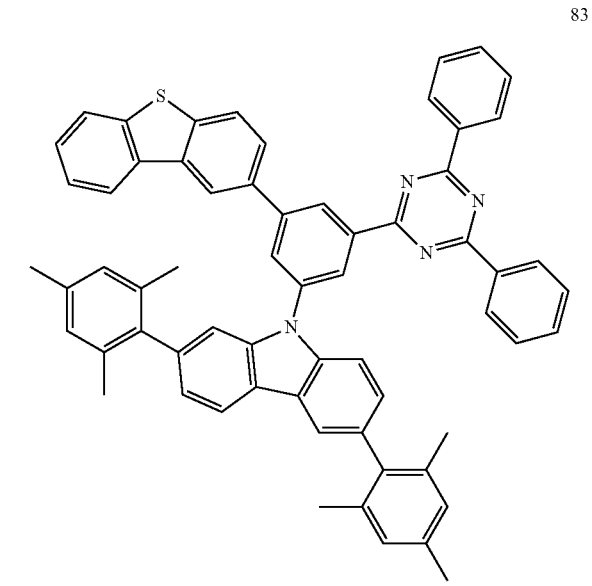

87

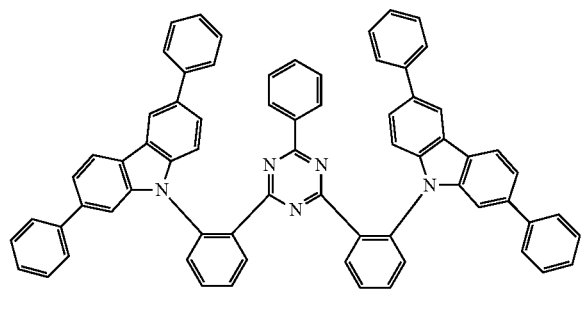

Organic electroluminescence devices of Comparative Examples 1 to 5 were manufactured utilizing Comparative Compounds C-1 to C-5 respectively as dopant materials of an emission layer.

Comparative Compounds

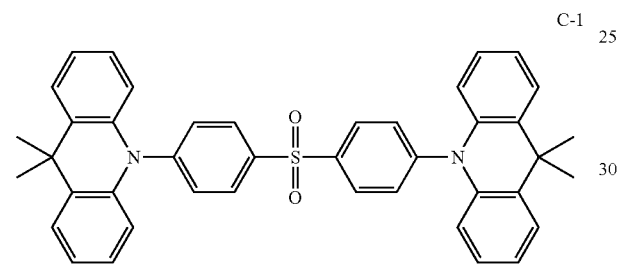
C-1

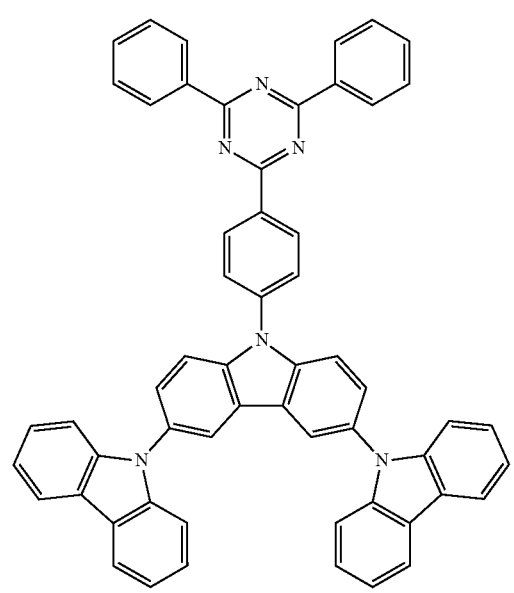
C-2

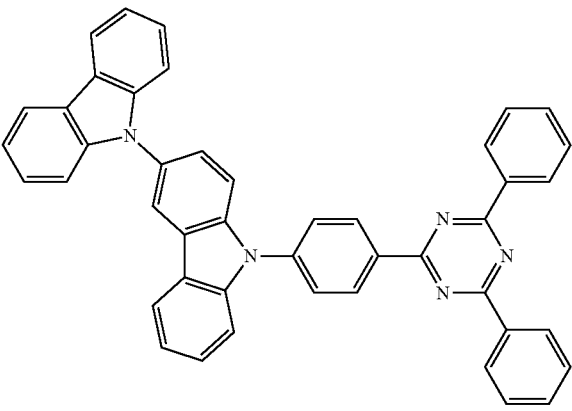
C-3

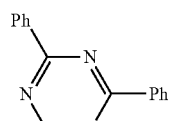
C-4

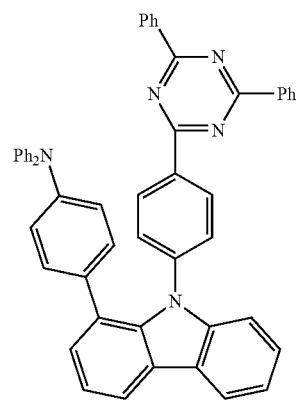

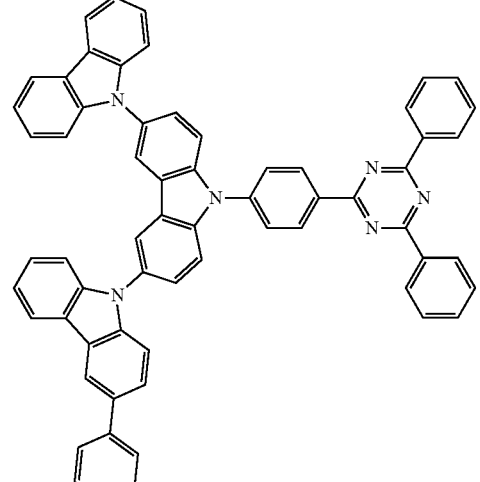
C-5

Organic electroluminescence devices of Examples 1 to 10 and Comparative Examples 1 to 5 were manufactured as follows.

An ITO glass substrate (Product of Corning Co.) on which an ITO layer with a thickness of about 15 $\Omega/cm^2$ (1,200 Å) was formed and cut into a size of 50 mm×50 mm×0.7 mm, and then, was washed with ultrasonic waves utilizing isopropyl alcohol and pure water each for about 5 minutes, and further cleaned by exposing to ultraviolet rays for about 30 minutes and exposing to ozone. Then, the ITO glass substrate was installed in a vacuum deposition apparatus.

On the substrate, a known compound 2-TNATA was vacuum deposited first to a thickness of about 600 Å to form a hole injection layer, and then, on the hole injection layer, NPB was vacuum deposited to a thickness of about 300 Å to form a hole transport layer.

On the hole transport layer, BCPDS and POPCPA in a weight ratio of 1:1, which were co-hosts, and a respective Example Compound or Comparative Compound, which was a dopant, were co-deposited such that the weight ratio of the co-hosts and the dopant was 90:10 to form an emission layer to a thickness of about 300 Å.

On the emission layer, TSPO1 was deposited to a thickness of about 50 Å to form a hole blocking layer, and on the hole blocking layer, Alq3 was deposited to a thickness of about 300 Å to form an electron transport layer. On the electron transport layer, LiF was deposited to a thickness of about 10 Å to form an electron injection layer, and on the electron injection layer, Al was deposited in vacuum to form a cathode with a thickness of about 3,000 Å, thereby manufacturing an organic electroluminescence device.

The driving voltage, efficiency, maximum quantum efficiency and emission color of the organic electroluminescence devices according to Examples 1 to 10 and Comparative Examples 1 to 5 were measured and are shown in Table 2 below.

The driving voltage, current density, luminance, emission efficiency, emission color and maximum emission wavelength were measured utilizing Keithley SMU 236 and a brightness photometer PR650.

TABLE 2

| | Emission layer dopant material | Driving voltage (V) | Efficiency (cd/A) | Maximum quantum efficiency (%) | Emission color |
|---|---|---|---|---|---|
| Example 1 | Example Compound 4 | 5.7 | 22.9 | 20 | Blue |
| Example 2 | Example Compound 22 | 5.8 | 23.5 | 19.5 | Blue |
| Example 3 | Example Compound 23 | 5.3 | 24.2 | 25.5 | Blue |
| Example 4 | Example Compound 24 | 5.2 | 22 | 20.6 | Blue |
| Example 5 | Example Compound 29 | 5.1 | 23.5 | 22 | Blue |
| Example 6 | Example Compound 47 | 5.2 | 27 | 23 | Blue |
| Example 7 | Example Compound 51 | 5.4 | 21.5 | 19 | Blue |
| Example 8 | Example Compound 72 | 5.6 | 22.2 | 21 | Blue |
| Example 9 | Example Compound 83 | 5.0 | 26.6 | 23.3 | Blue |
| Example 10 | Example Compound 87 | 5.1 | 24.1 | 20.8 | Blue |
| Comparative Example 1 | Comparative Compound C-1 | 6.7 | 19.3 | 18.5 | Blue |
| Comparative Example 2 | Comparative Compound C-1 | 6.1 | 32.8 | 17 | Greenish blue |
| Comparative Example 3 | Comparative Compound C-2 | 6.3 | 36.5 | 18.8 | Greenish blue |
| Comparative Example 4 | Comparative Compound C-3 | 6.9 | 38.1 | 16.9 | Greenish blue |
| Comparative Example 5 | Comparative Compound C-4 | 5.9 | 31.5 | 19.9 | Greenish blue |

The resultant values are values at a current density of about 50 mA/cm$^2$. Referring to the results of Table 2, it was found that if the nitrogen-containing compound according to an embodiment of the inventive concept is utilized as a material for an emission layer, effects of decreasing the driving voltage and increasing the efficiency were attained. In addition, it was found that blue emission was accomplished.

In addition, Comparative Examples 2, 3 and 5, which utilized compounds having a structure in which another carbazole groups were substituted at positions 3 and/or 6 of a carbazole group, had a low singlet energy level and a high HOMO energy level, and tended to show red shifted emission wavelengths, and thus, were inappropriate as a material accomplishing deep blue color.

Meanwhile, Comparative Example 4 utilized a compound having a structure in which carbazole was bonded to an amine group, and had an increased HOMO energy level and a decreased singlet energy level, and thus also tended to show red shifted results.

In Comparative Examples 2 to 5, it was shown that the emission wavelengths were near green light, which is undesirable when blue light was intended.

The nitrogen-containing compound according to an embodiment of the inventive concept is favorable for accomplishing an organic electroluminescence device with high efficiency and deep blue color. The organic electroluminescence device according to an embodiment of the inventive concept has excellent efficiency and long life. The organic electroluminescence device according to an embodiment of the inventive concept has the effects of decreasing a driving voltage.

The organic electroluminescence device according to an embodiment of the inventive concept has excellent efficiency.

The nitrogen-containing compound according to an embodiment of the inventive concept may be applied to an organic electroluminescence device to contribute to high efficiency.

Expressions such as "at least one of" or "at least one selected from" when preceding a list of elements, modify the entire list of elements and do not modify the individual elements of the list. Further, the use of "may" when describing embodiments of the present invention refers to "one or more embodiments of the present invention." Also, the term "exemplary" is intended to refer to an example or illustration.

As used herein, the terms "substantially," "about," and similar terms are used as terms of approximation and not as terms of degree, and are intended to account for the inherent deviations in measured or calculated values that would be recognized by those of ordinary skill in the art.

Although the exemplary embodiments of the present invention have been described, it is understood that the present invention should not be limited to these exemplary embodiments but various changes and modifications can be made by one of ordinary skill in the art within the spirit and scope of the present invention as hereinafter claimed, and equivalents thereof.

What is claimed is:

1. An organic electroluminescence device, comprising:
a first electrode;
a hole transport region on the first electrode;
an emission layer on the hole transport region;
an electron transport region on the emission layer; and
a second electrode on the electron transport region,
wherein
the emission layer comprises a nitrogen-containing compound comprising a triazine moiety and a carbazole moiety,
when the triazine moiety and the carbazole moiety are connected through a phenylene group, the phenylene group is unsubstituted or substituted with only
I) a deuterium atom,
II) a substituted or unsubstituted aryl group having 6 to 30 carbon atoms for forming a ring, or
III) a substituted or unsubstituted heteroaryl group having 2 to 30 carbon atoms for forming a ring, and
in the carbazole moiety, one of position 2 or 7 is substituted, or at least two positions among 2, 3 and 7 are substituted,
wherein
1) each of positions 2 and 7 is independently substituted with a substituted or unsubstituted phenyl group, or a substituted or unsubstituted carbazole group,
2) one of position 2 or 7 is substituted with a substituted or unsubstituted phenyl group, or a substituted or unsubstituted carbazole group, and position 3 is substituted with a substituted or unsubstituted phenyl group,
3) at least one of position 2 or 7 is substituted with a substituted or unsubstituted carbazole group, or a substituted phenyl group,
4) the triazine moiety is substituted with a phenyl group that is substituted with a carbazole group, or a substituted or unsubstituted heteroaryl group having 2 to 30 carbon atoms for forming a ring, or
5) the triazine moiety and the carbazole moiety are connected through a phenylene group, and
the phenylene group is substituted with a substituted or unsubstituted aryl group having 6 to 30 carbon atoms for forming a ring, or a substituted or unsubstituted heteroaryl group having 2 to 30 carbon atoms for forming a ring, and
wherein when one of position 2 or position 7 is a substituted or unsubstituted phenyl group and an other one of position 2 or position 7 is hydrogen, positions 3 and 6 are each hydrogen, and when the triazine moiety and the carbazole moiety are connected through meta or para position of the phenylene group substituted with a substituted aryl group, a substituent of the substituted aryl group is selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocyclic group,
when each of position 2 and position 7 is a substituted or unsubstituted phenyl group, and when the triazine moiety and the carbazole moiety are connected through meta or para position of the phenylene group substituted with a substituted aryl group, a substituent of the substituted aryl group is selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocyclic group,
when each of position 2 and position 7 is a substituted or unsubstituted phenyl group, and when the triazine moiety and the carbazole moiety are connected through meta or para position of an unsubstituted phenylene group, the triazine moiety is substituted with a heterocyclic group or a phenyl group that is substituted with a carbazole group, and
when the triazine moiety and the carbazole moiety are connected through ortho position of a phenylene group,
i) at least one of position 2 or position 7 is substituted with a substituted or unsubstituted carbazole group,
ii) one of position 2 or position 7 is substituted with a substituted or unsubstituted phenyl group, or a substituted or unsubstituted carbazole group, and position 3 is substituted with a substituted or unsubstituted phenyl group,
iii) one of position 2 or 7 is substituted with a substituted or unsubstituted phenyl group, and a remainder of position 2 or 7 is not substituted, and position 3 is not substituted, or
iv) the triazine moiety is substituted with a heterocyclic group.

2. The organic electroluminescence device of claim 1, wherein one of positions 2 and 3 is unsubstituted.

3. The organic electroluminescence device of claim 1, wherein the nitrogen-containing compound comprises one or two carbazole moieties.

4. The organic electroluminescence device of claim 1, wherein the triazine moiety is substituted with one or more substituted or unsubstituted phenyl groups.

5. The organic electroluminescence device of claim 1, wherein the emission layer comprises a host and a dopant, and
the dopant comprises the nitrogen-containing compound.

6. The organic electroluminescence device of claim 5, wherein the dopant is a thermally activated delayed fluorescence dopant.

7. The organic electroluminescence device of claim 1, wherein the emission layer comprises a host and a dopant, and
the host comprises the nitrogen-containing compound.

8. The organic electroluminescence device of claim 1, wherein the nitrogen-containing compound is represented by following Formula 1:

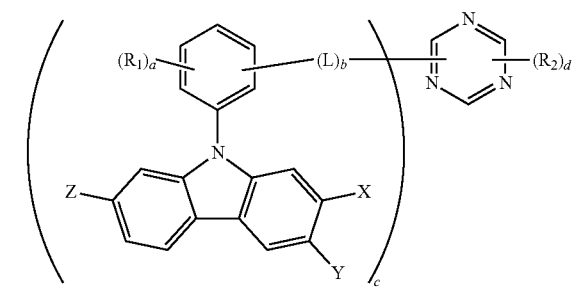

Formula 1 wherein in Formula 1,

X and Z are each independently a hydrogen atom, a deuterium atom, a substituted or unsubstituted phenyl group, or a substituted or unsubstituted carbazole group, Y is a hydrogen atom, a deuterium atom, or a substituted or unsubstituted phenyl group, one of X or Z is not a hydrogen atom and is not a deuterium atom, or at least two of X, Y or Z are not a hydrogen atom and is not a deuterium atom, one of X and Y is a hydrogen atom or a deuterium atom, $R_1$ and $R_2$ are each independently a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring, L is a substituted or unsubstituted arylene group having 6 to 30 carbon atoms for forming a ring, or a substituted or unsubstituted heteroarylene group having 2 to 30 carbon atoms for forming a ring, a is an integer of 0 to 4, b is an integer of 0 to 2, c is 1 or 2, and d is 1 or 2, and wherein 1) each of X and Z is independently a substituted or unsubstituted phenyl group, or a substituted or unsubstituted carbazole group, 2) one of X or Z is a substituted or unsubstituted phenyl group, or a substituted or unsubstituted carbazole group, and Y is a substituted or unsubstituted phenyl group, 3) at least one of X or Z is a substituted or unsubstituted carbazole group, or a substituted phenyl group, 4) d is 1 or 2, and at least one $R_2$ is a phenyl group that is substituted with a carbazole group, or a substituted or unsubstituted heteroaryl group having 2 to 30 carbon atoms for forming a ring, or 5) a is an integer of 1 to 4, and at least one $R_1$ is a substituted or unsubstituted aryl group having 6 to 30 carbon atoms for forming a ring, or a substituted or unsubstituted heteroaryl group having 2 to 30 carbon atoms for forming a ring, and wherein when one of X or Z is a substituted or unsubstituted phenyl group and an other one of X or Z is hydrogen, Y is hydrogen, the triazine moiety and the carbazole moiety are connected through meta or para position of the phenylene group, and when a is 1 and $R_1$ is a substituted aryl group, a substituent of the substituted aryl group is selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocyclic group, when each of X and Z is a substituted or unsubstituted phenyl group, the triazine moiety and the carbazole moiety are connected through meta or para position of the phenylene group, and when a is 1 and $R_1$ is a substituted aryl group, a substituent of the substituted aryl group is selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocyclic group, when each of X and Z is a substituted or unsubstituted phenyl group, the triazine moiety and the carbazole moiety are connected through meta or para position of the phenylene group, and when $(R_1)_a$ is hydrogen, at least one $R_2$ is a heterocyclic group or a phenyl group that is substituted with a carbazole group, and when the triazine moiety and the carbazole moiety are connected through ortho position of the phenylene group,
  i) at least one of X or Z is a substituted or unsubstituted carbazole group,
  ii) one of X or Z is a substituted or unsubstituted phenyl group, or a substituted or unsubstituted carbazole group, and Y is a substituted or unsubstituted phenyl group,
  iii) one of X or Z is a substituted or unsubstituted phenyl group, another one of X or Z is a hydrogen atom, and Y is a hydrogen atom, or
  iv) d is 1 or 2, and at least one $R_2$ is a heterocyclic group.

9. The organic electroluminescence device of claim 8, wherein Z is an unsubstituted phenyl group, or a phenyl group substituted with at least one selected from a cyano group, a halogen atom, an alkyl group having 1 to 5 carbon atoms, and an aryl group having 6 to 15 carbon atoms for forming a ring.

10. The organic electroluminescence device of claim 8, wherein a is 0 or 1,
wherein when a is 1, $R_1$ is a substituted or unsubstituted dibenzothiophene group, or a substituted or unsubstituted dibenzofuran group.

11. The organic electroluminescence device of claim 8, wherein b is 0.

12. The organic electroluminescence device of claim 8, wherein the nitrogen-containing compound represented by Formula 1 is represented by following Formula 1-1 or Formula 1-2:

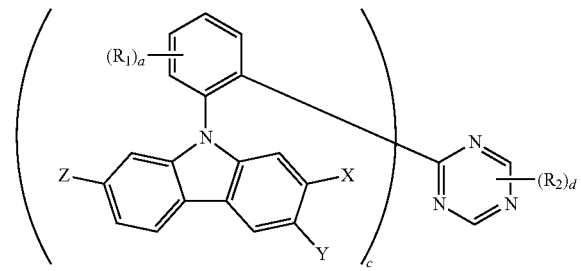

Formula 1-1

-continued
Formula 1-2
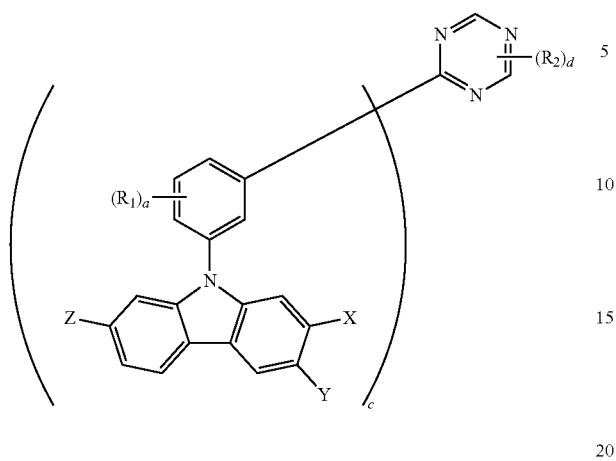
wherein in Formulae 1-1 and 1-2,
X, Y, Z, $R_1$, $R_2$, a, c and d are the same as respectively defined in Formula 1.
13. The organic electroluminescence device of claim 1, wherein the nitrogen-containing compound is one selected from compounds represented in following Compound Group 1:
Compound Group 1
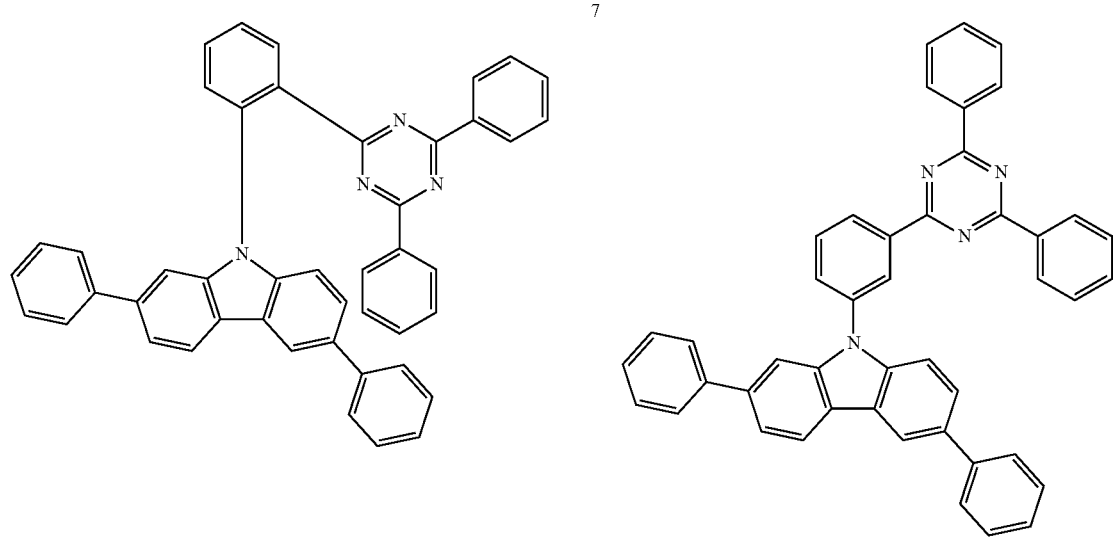

-continued
9
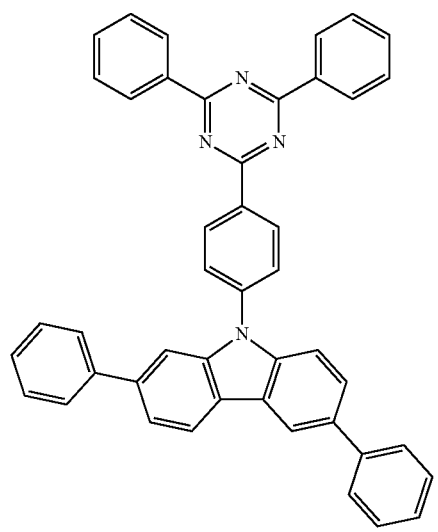
10
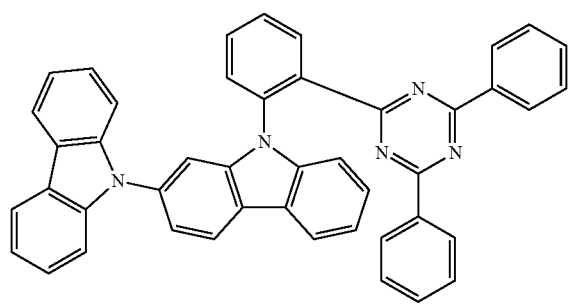
11
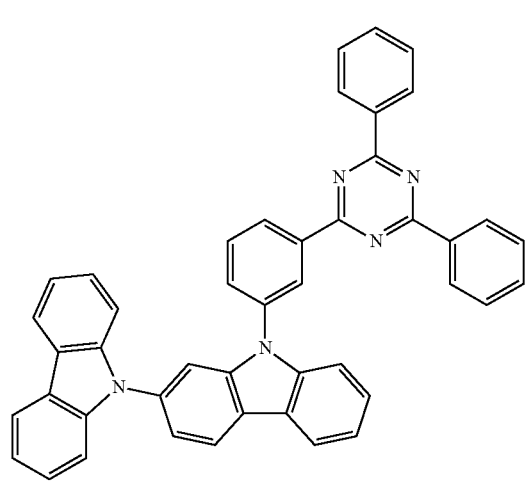
12
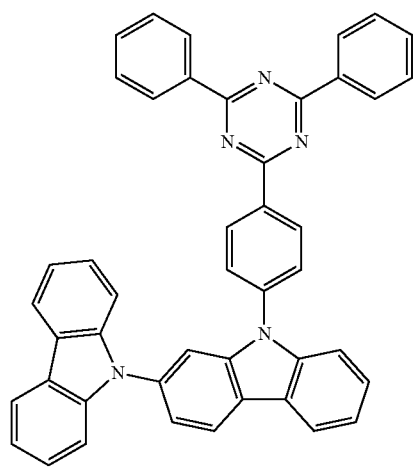
13
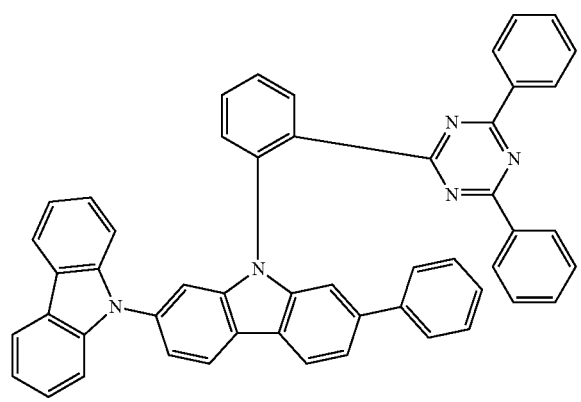
14
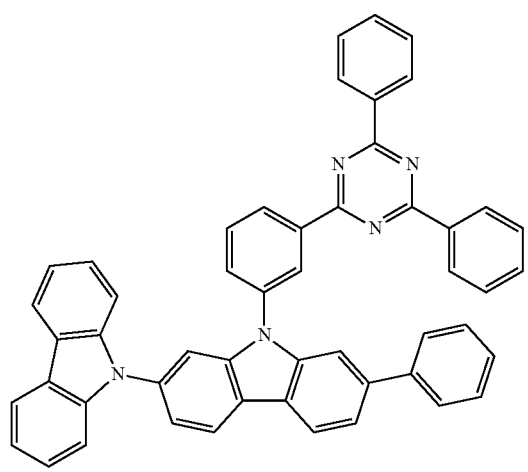

-continued
15
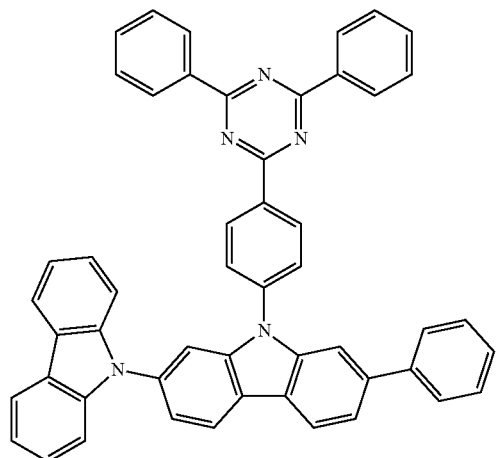
16
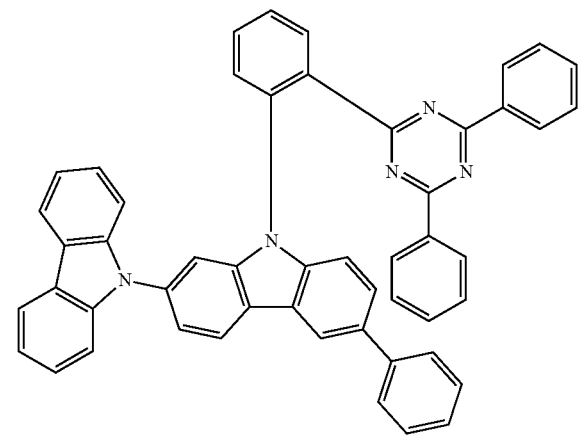
17
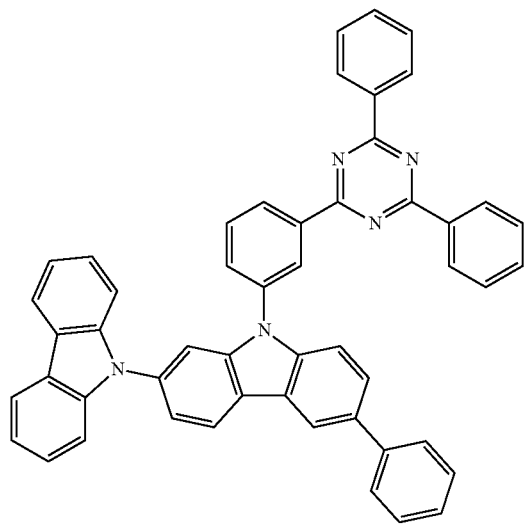
18
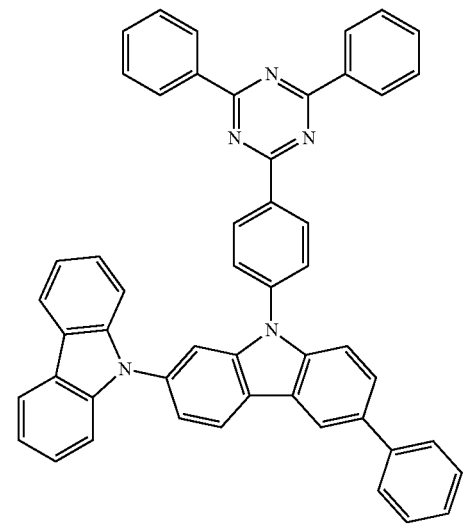
19
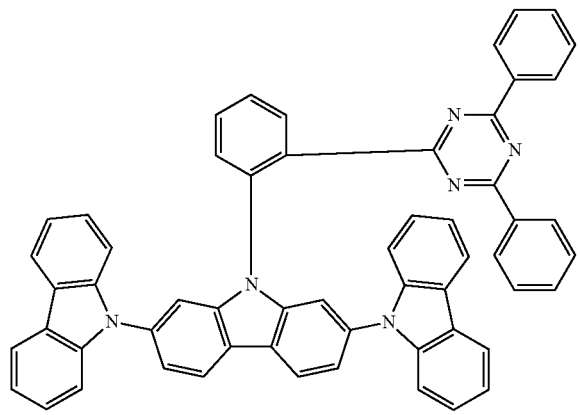
20
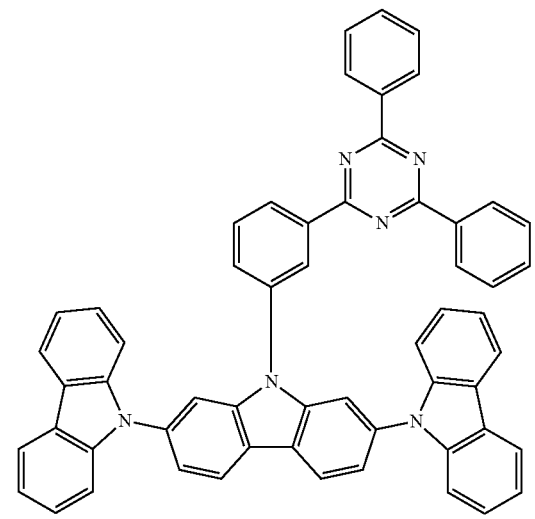

-continued
21
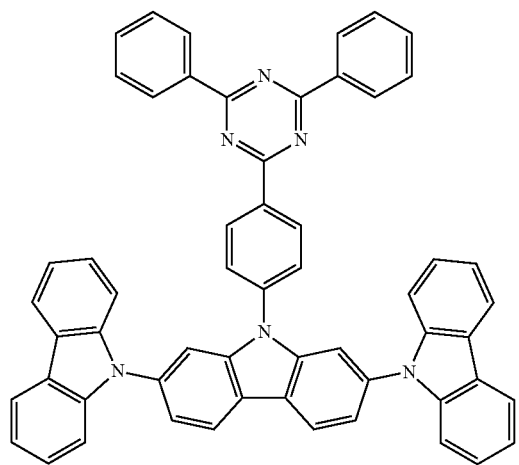
22
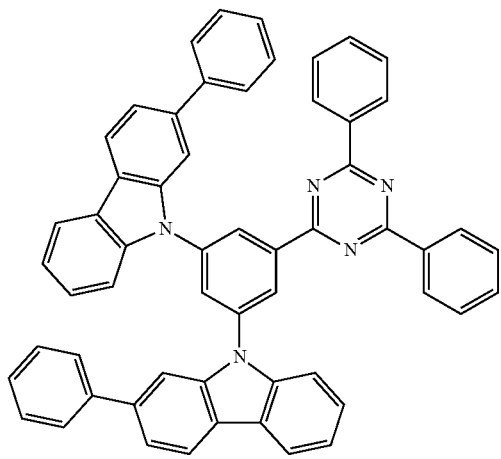
23
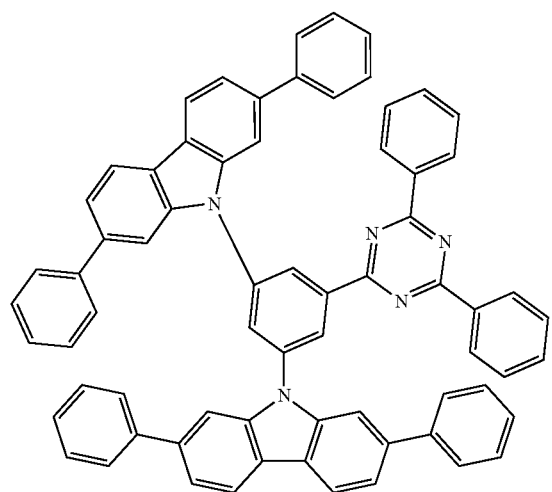
24
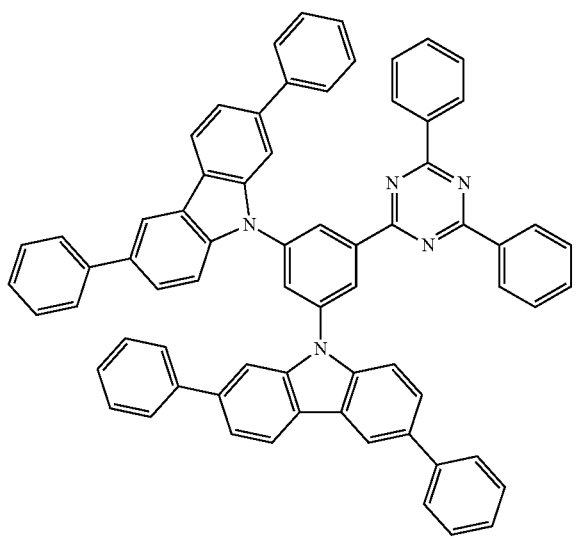
25
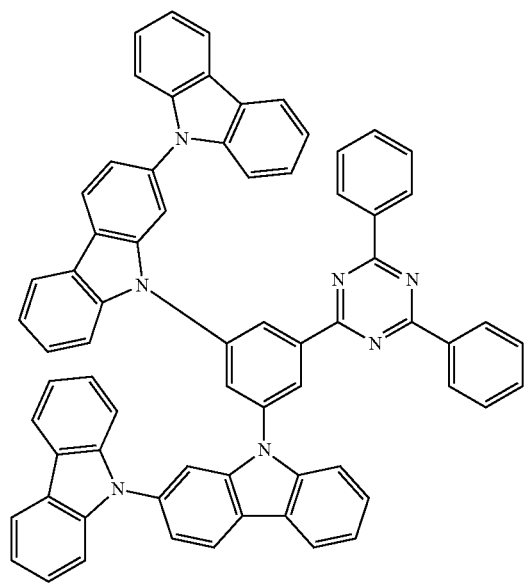
26
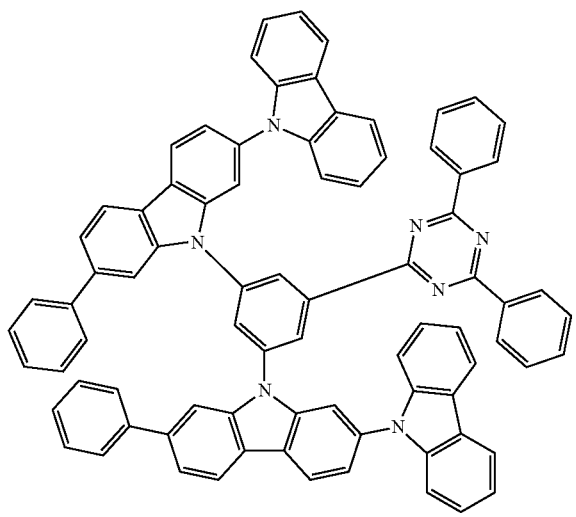

-continued
27
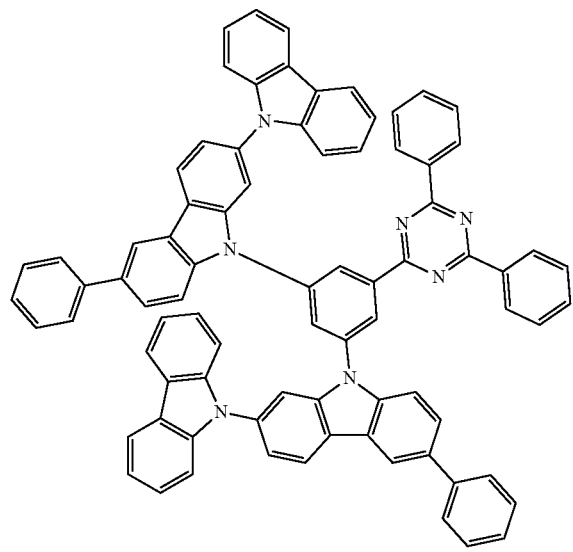
28
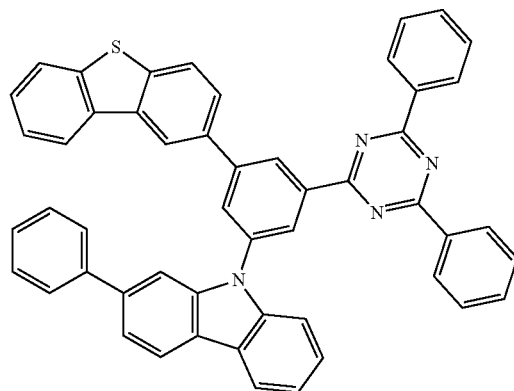
29
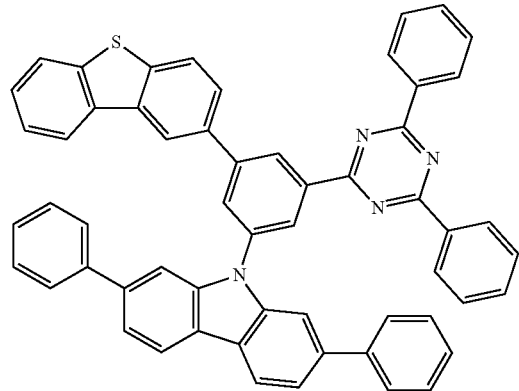
30
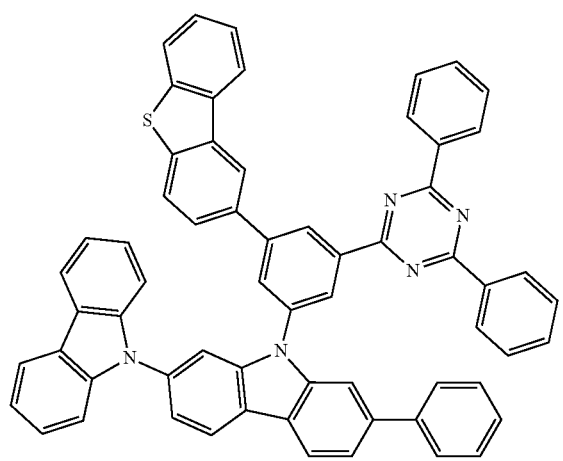
31
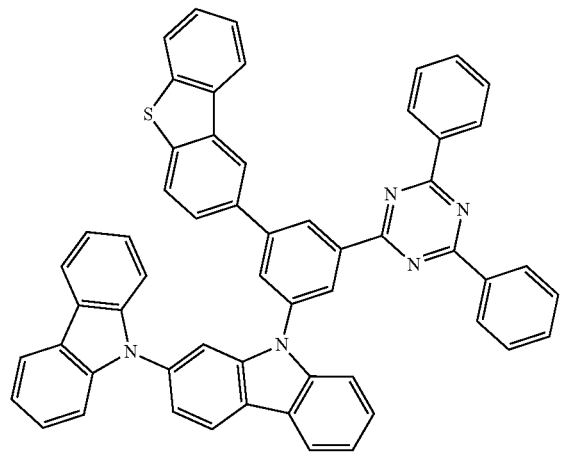
32
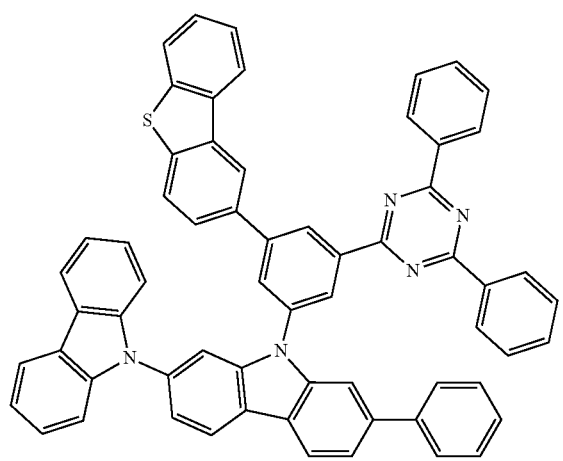

-continued
33
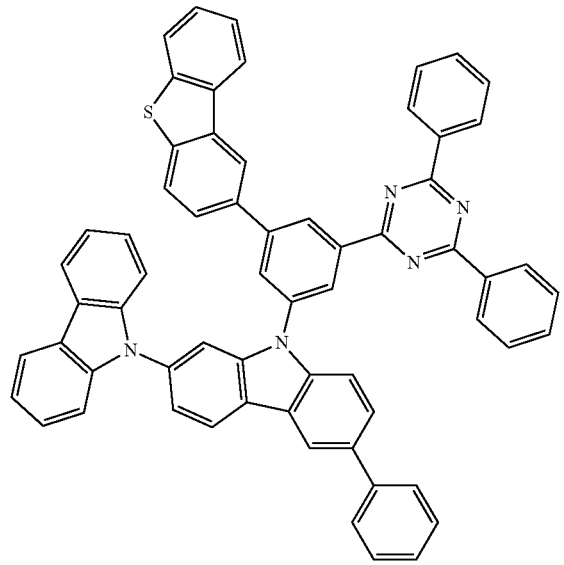
34
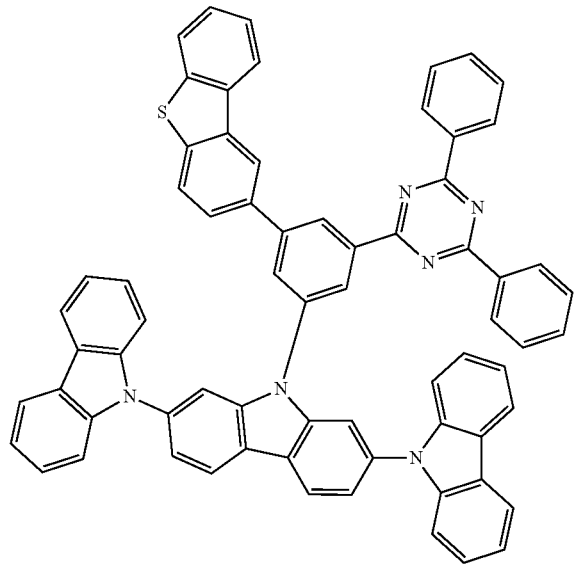
35
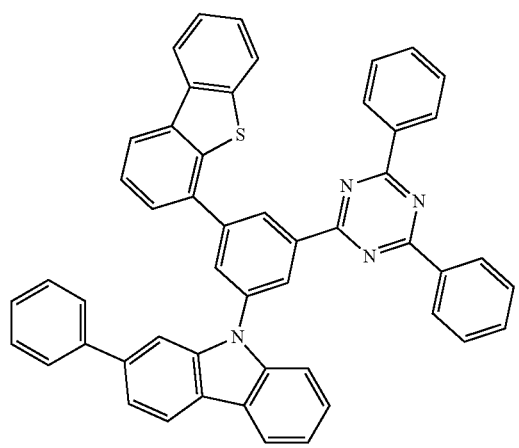
36
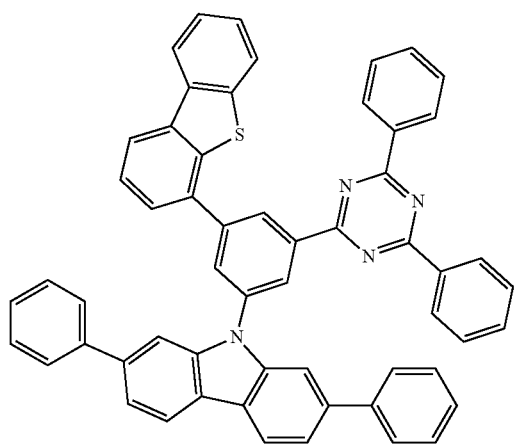
37
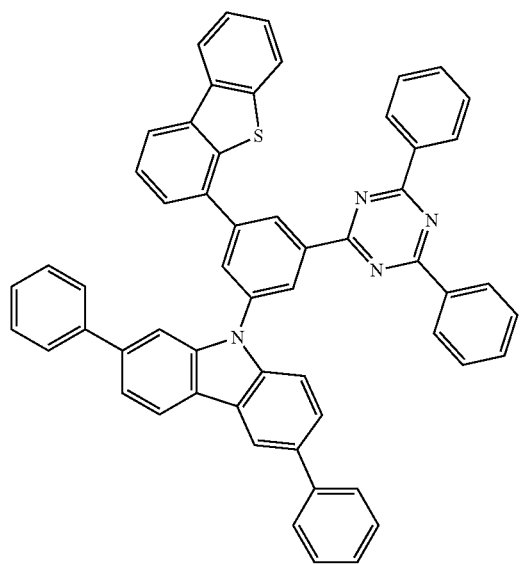
38
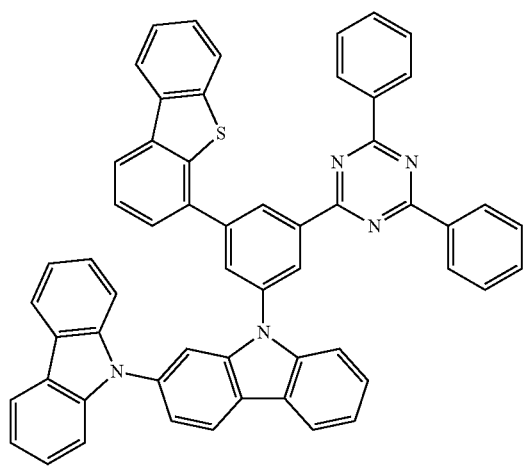

-continued
39
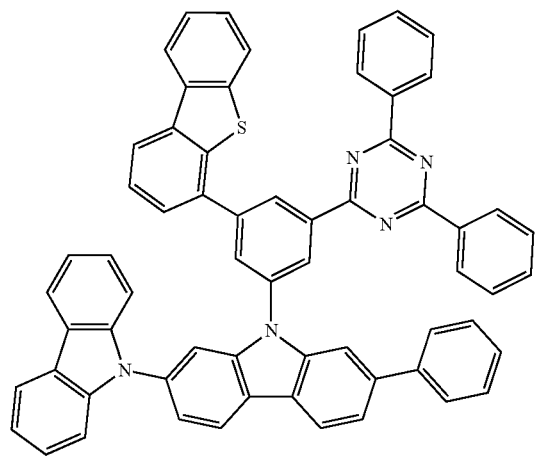
40
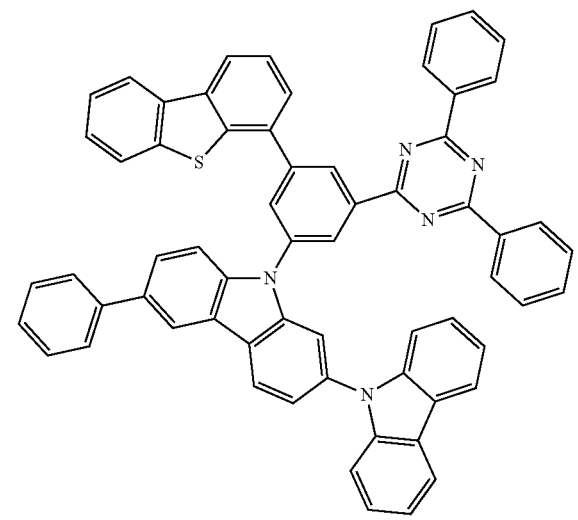
41
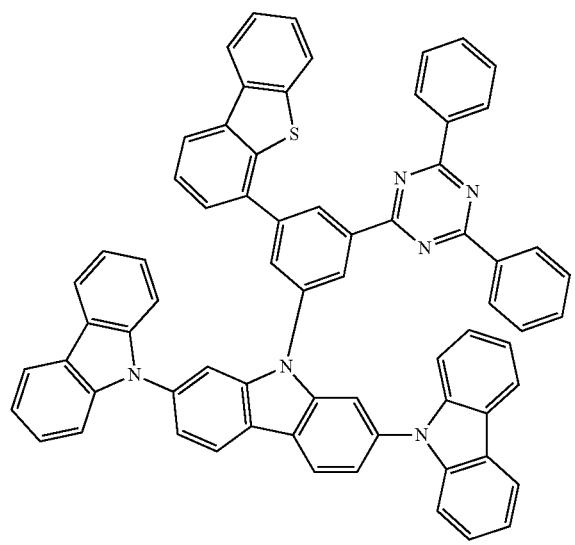
42
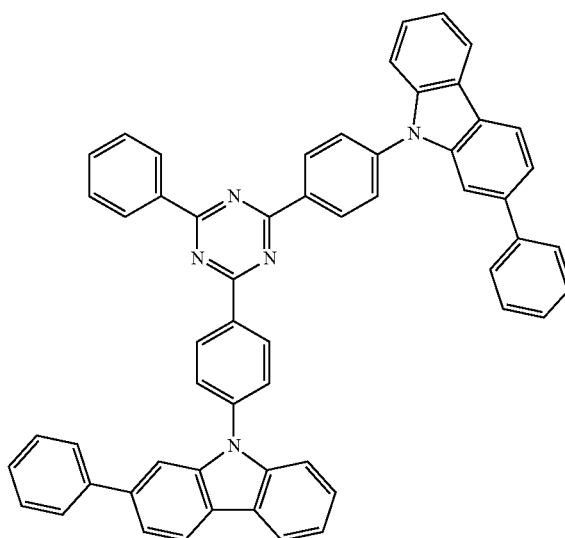
43
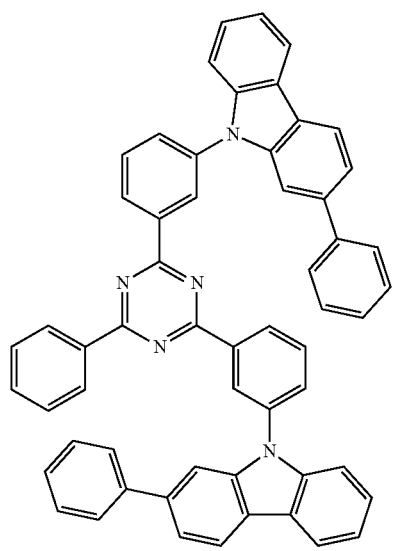

44
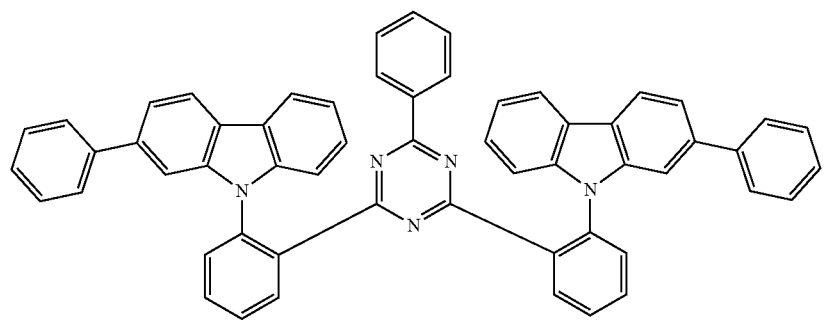
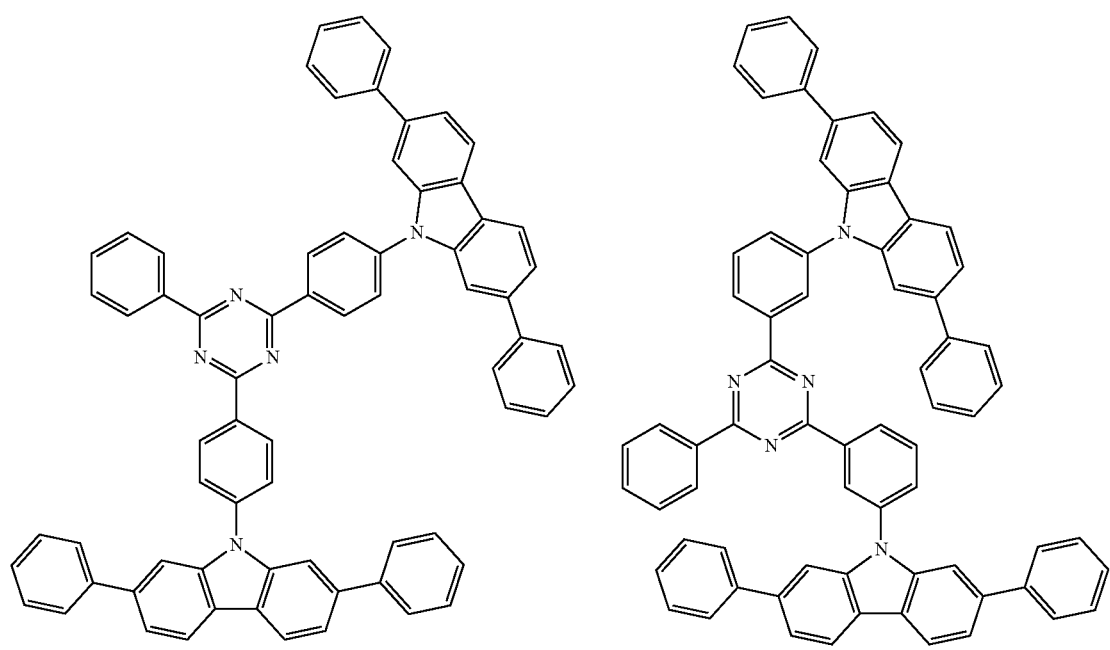
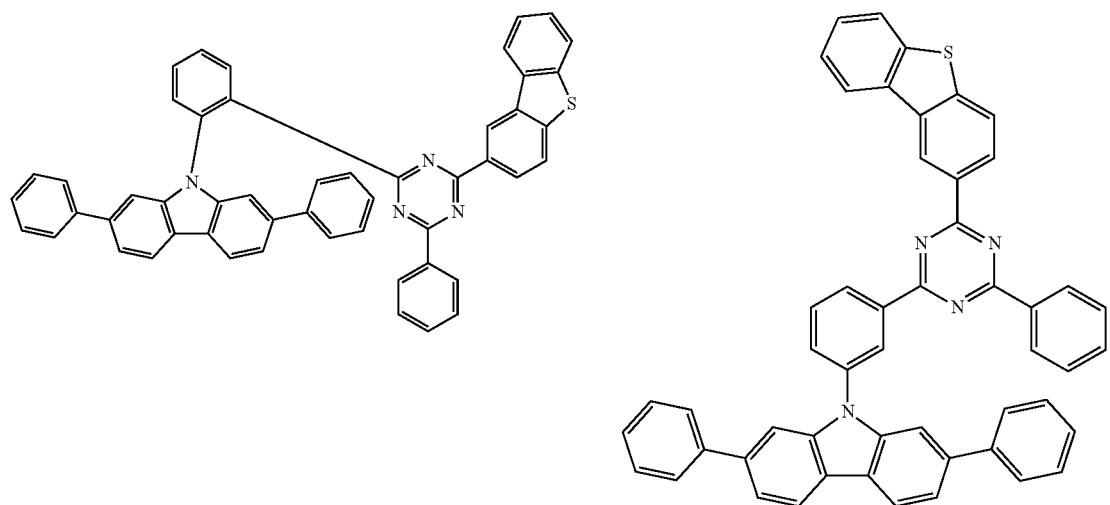

-continued
53
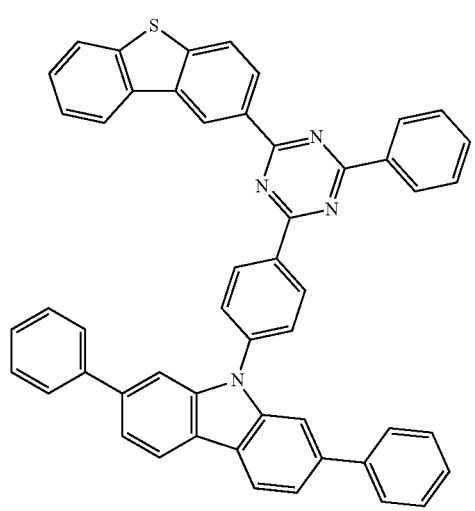
54
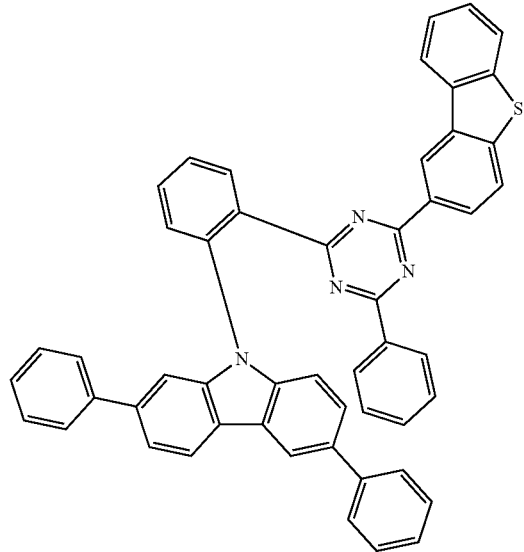
55
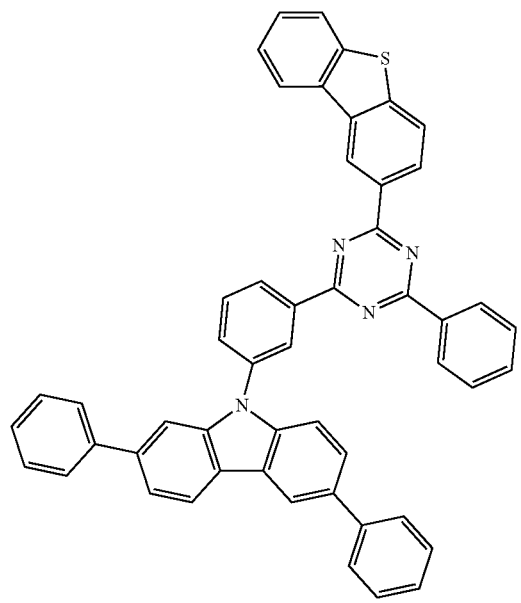
56
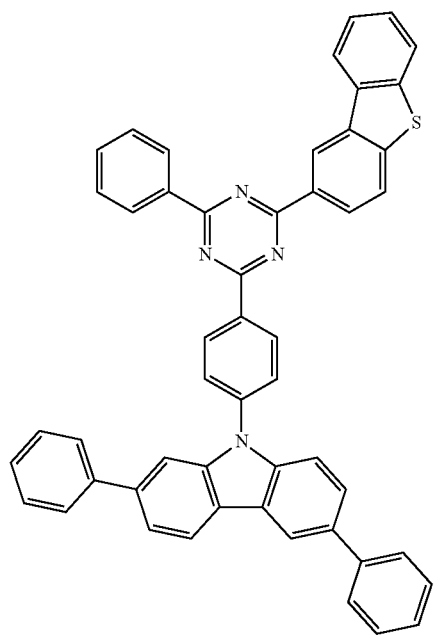

57
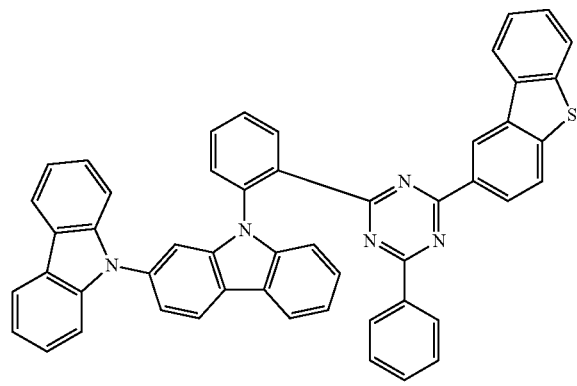
58
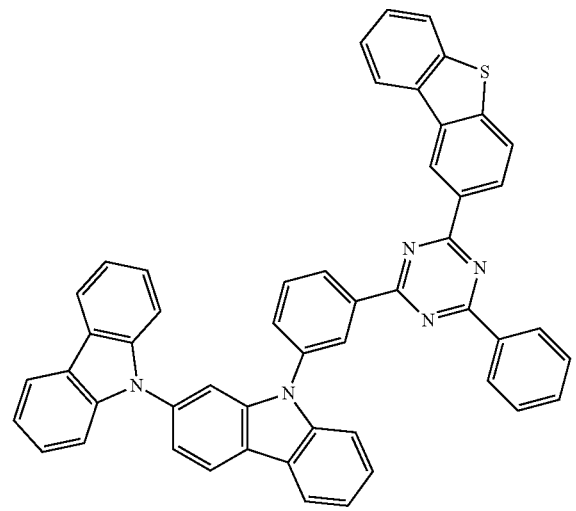
59
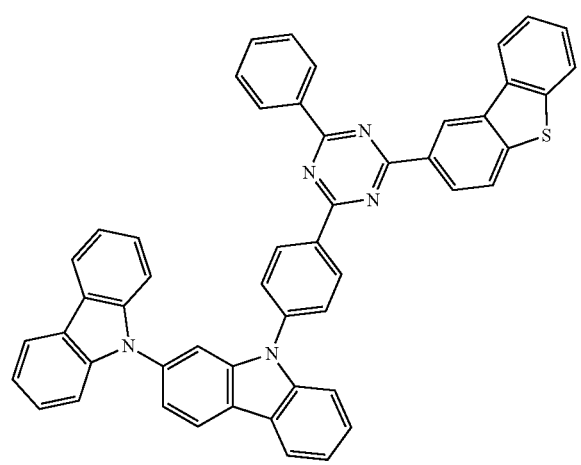
60
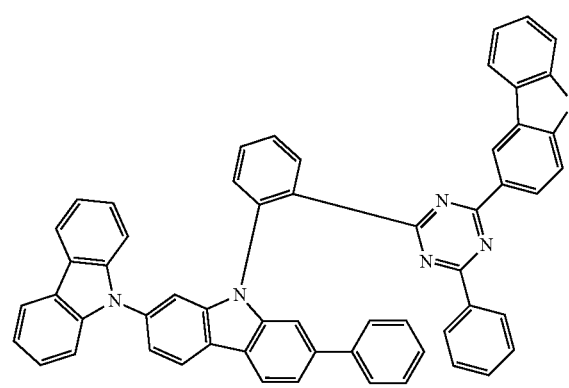
61
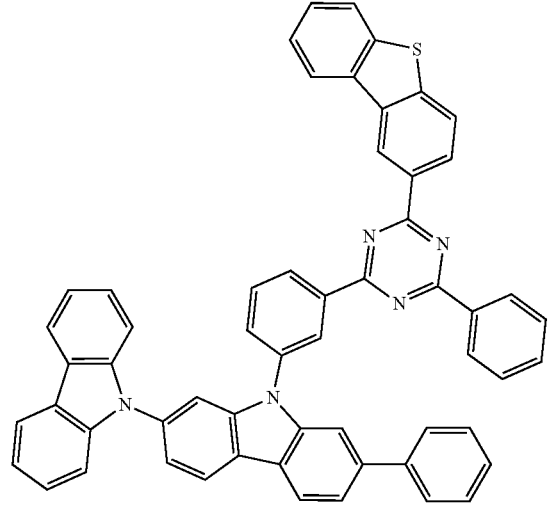
62
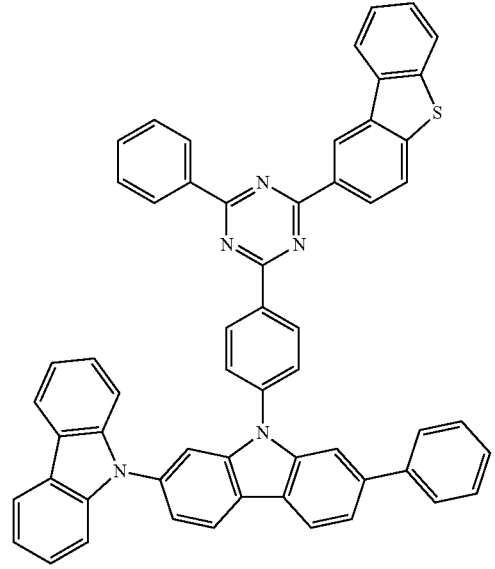

-continued
63
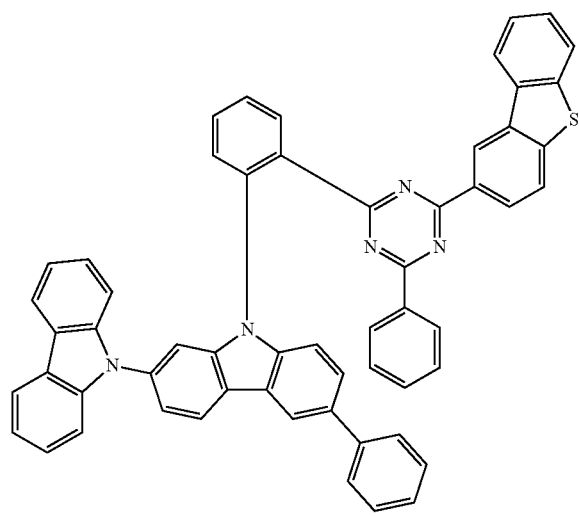
64
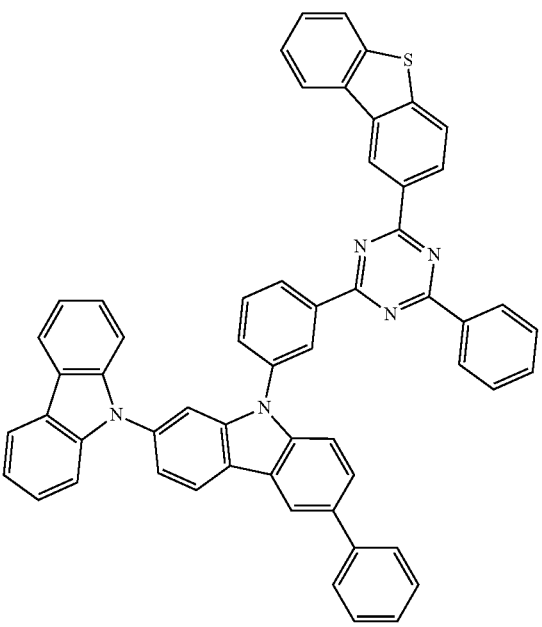
65
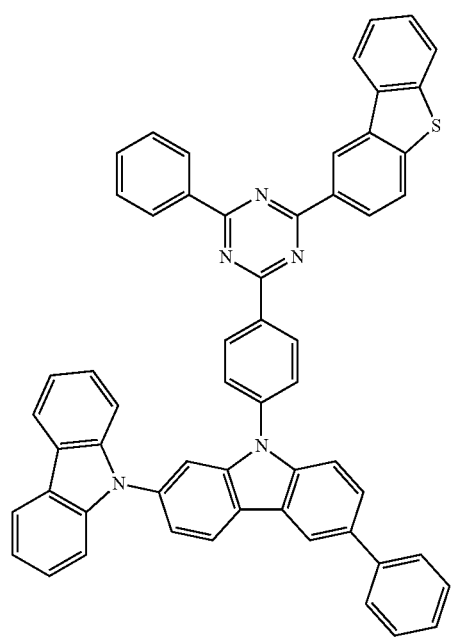
66
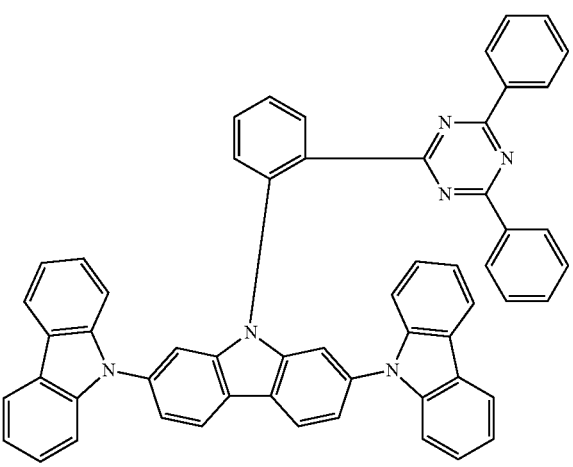

-continued
67
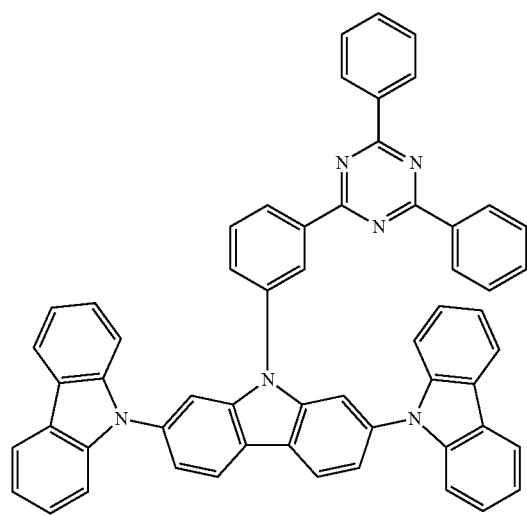
68
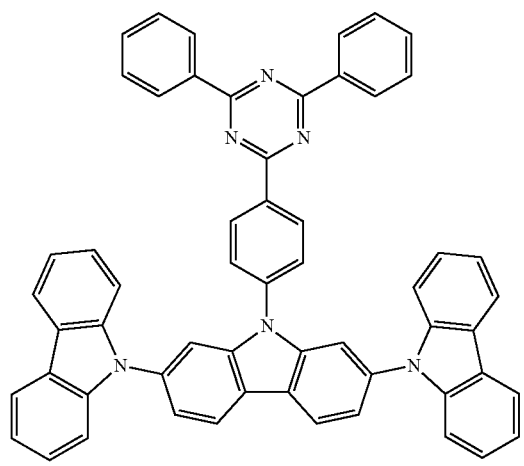
69
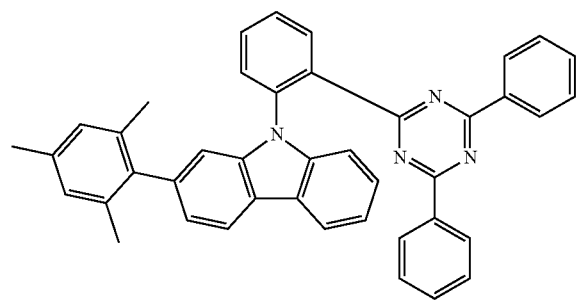
70
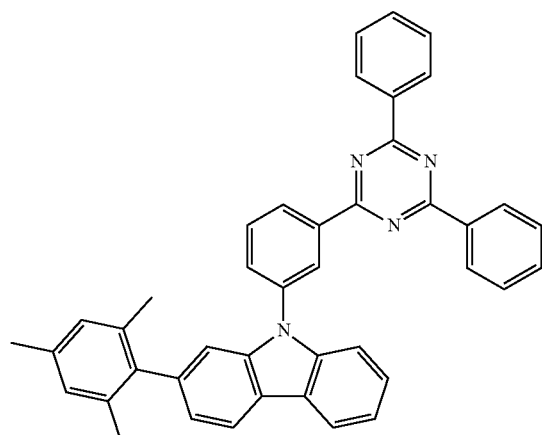
71
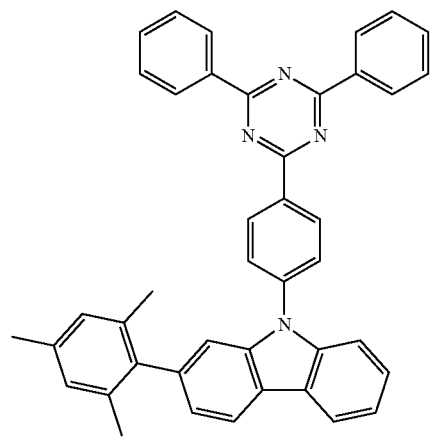
73
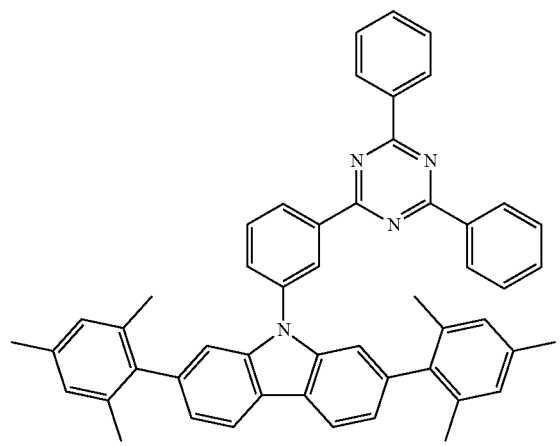

-continued
74
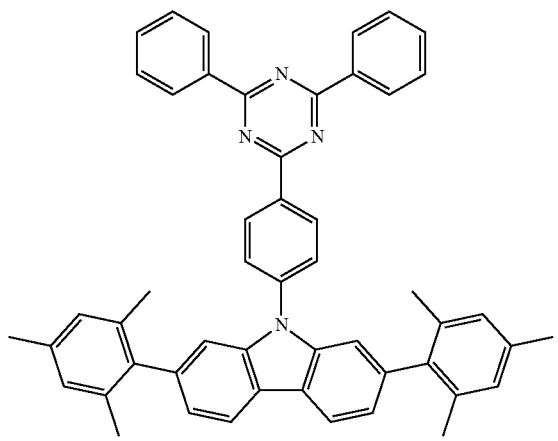
75
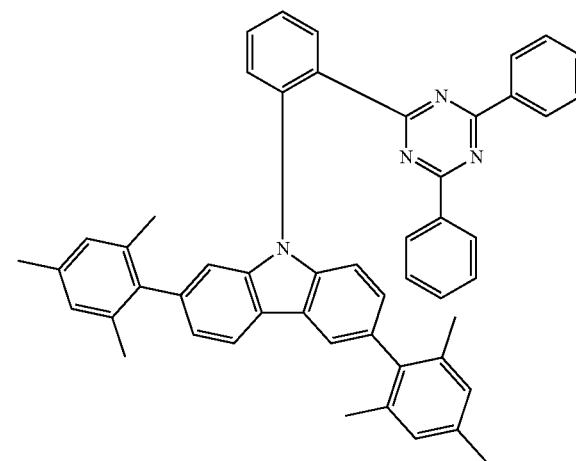
76
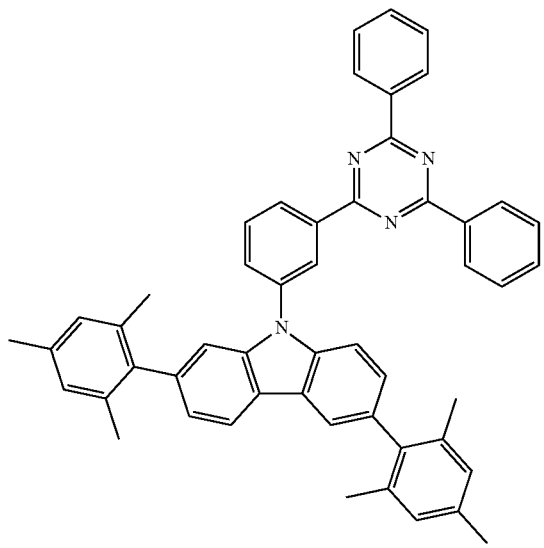
77
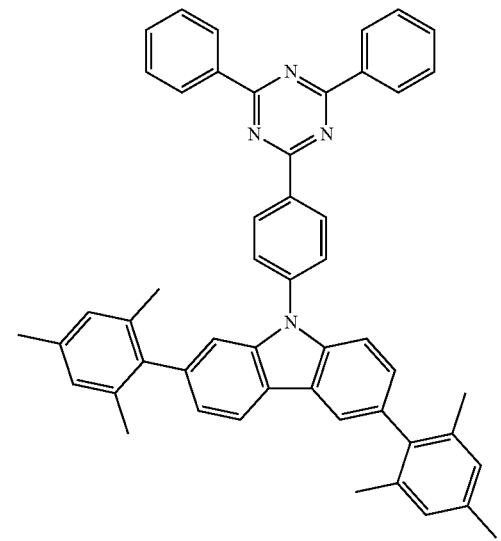
78
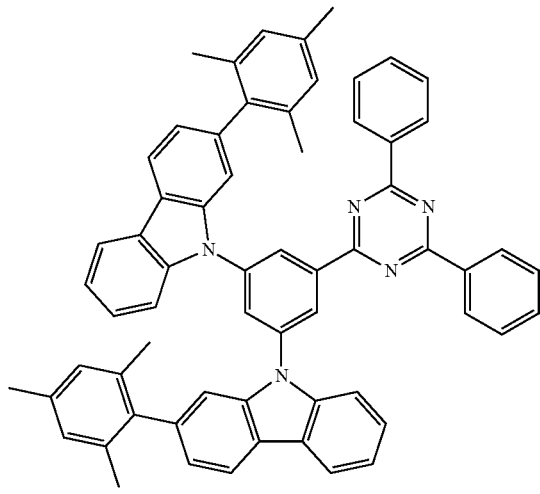
79
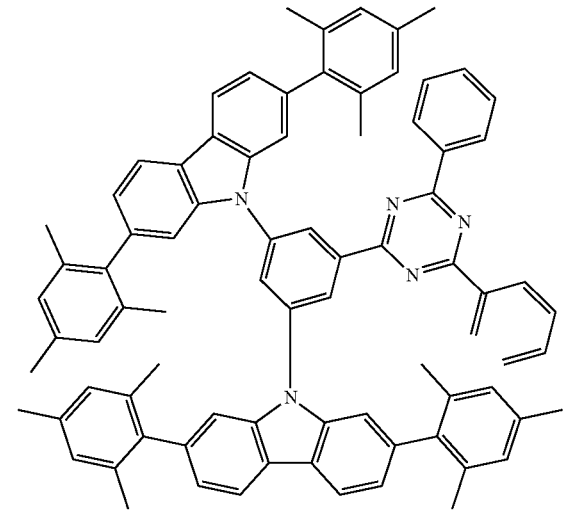

80
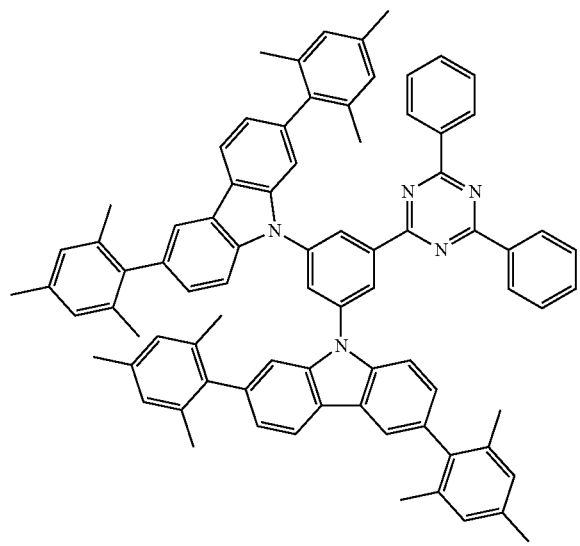
81
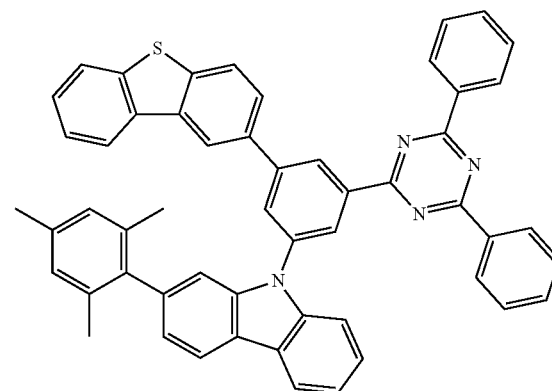
82
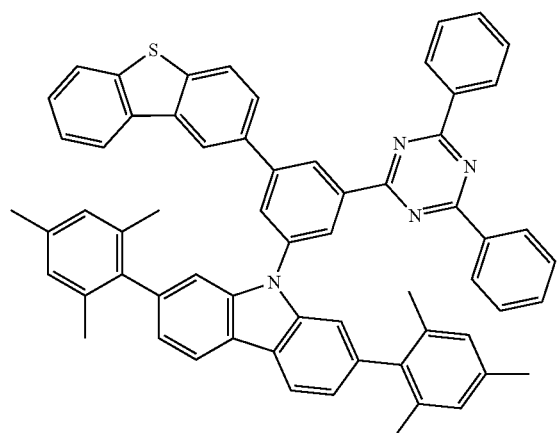
83
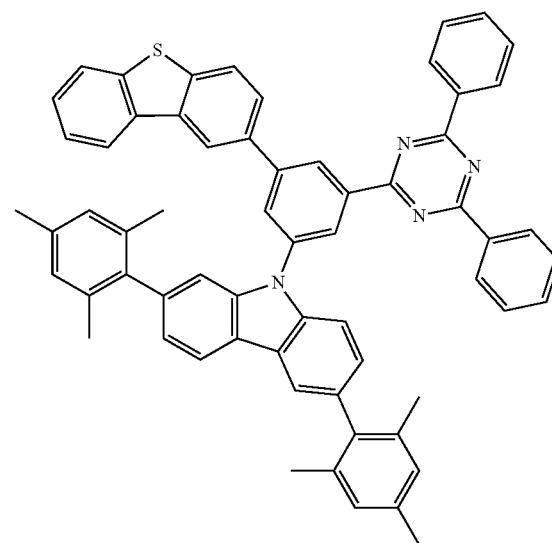

84

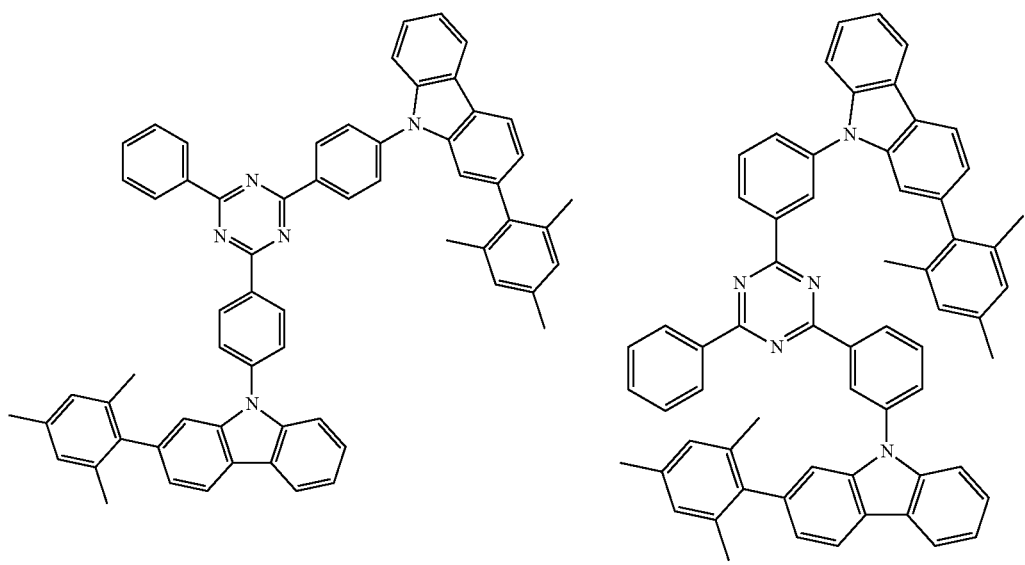

85

86

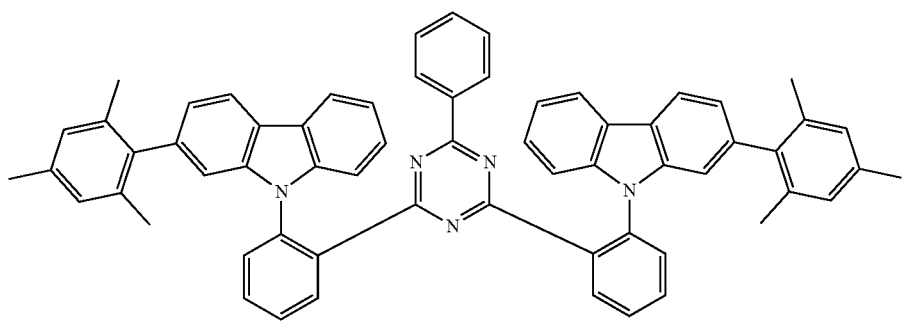

87

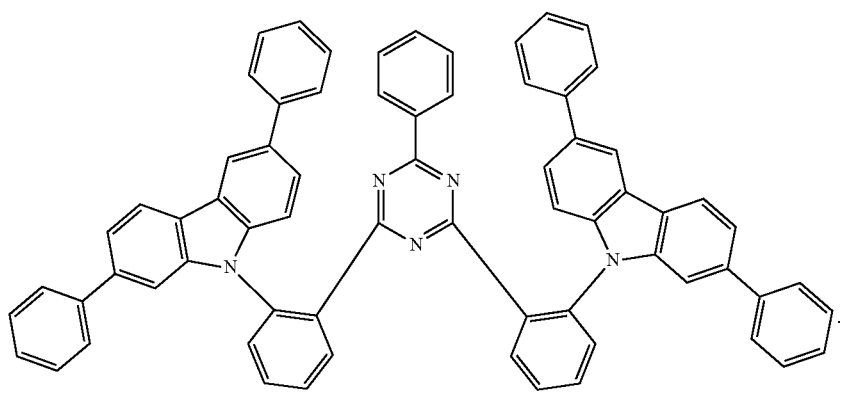

14. An organic electroluminescence device, comprising:
a first electrode;
a hole transport region on the first electrode;
an emission layer on the hole transport region;
an electron transport region on the emission layer; and
a second electrode on the electron transport region, wherein the first electrode and the second electrode each independently comprise at least one selected from the group consisting of Ag, Mg, Cu, Al, Pt, Pd, Au, Ni, Nd, Ir, Cr, Li, Ca, LiF/Ca, LiF/Al, Mo, Ti, In, Sn, Zn, compounds of two or more thereof, mixtures of two or more thereof, and oxides thereof, and wherein the emission layer comprises a nitrogen-containing compound represented by following Formula 1:

Formula 1

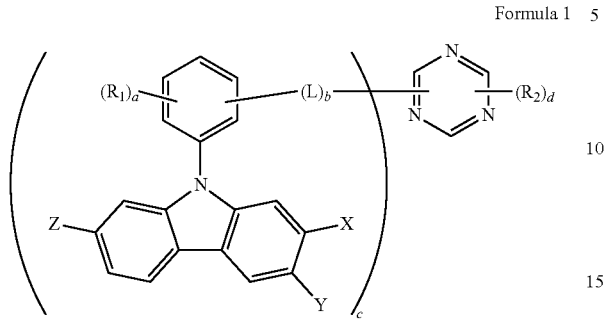

wherein in Formula 1,
X and Z are each independently a hydrogen atom, a deuterium atom, a substituted or unsubstituted phenyl group, or a substituted or unsubstituted carbazole group,
Y is a hydrogen atom, a deuterium atom, or a substituted or unsubstituted phenyl group,
one of X or Z is not a hydrogen atom and is not a deuterium atom, or at least two of X, Y or Z are not a hydrogen atom and is not a deuterium atom,
one of X and Y is a hydrogen atom or a deuterium atom,
$R_1$ and $R_2$ are each independently a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring,
L is a substituted or unsubstituted arylene group having 6 to 30 carbon atoms for forming a ring, or a substituted or unsubstituted heteroarylene group having 2 to 30 carbon atoms for forming a ring,
a is an integer of 0 to 4,
b is an integer of 0 to 2,
c is 1 or 2, and
d is 1 or 2, and
wherein
1) each of X and Z is independently a substituted or unsubstituted phenyl group, or a substituted or unsubstituted carbazole group,
2) one of X or Z is a substituted or unsubstituted phenyl group, or a substituted or unsubstituted carbazole group, and Y is a substituted or unsubstituted phenyl group,
3) at least one of X or Z is a substituted or unsubstituted carbazole group, or a substituted phenyl group,
4) d is 1 or 2, and at least one $R_2$ is a phenyl group that is substituted with a carbazole group, or a substituted or unsubstituted heteroaryl group having 2 to 30 carbon atoms for forming a ring, or
5) a is an integer of 1 to 4, and at least one $R_1$ is a substituted or unsubstituted aryl group having 6 to 30 carbon atoms for forming a ring, or a substituted or unsubstituted heteroaryl group having 2 to 30 carbon atoms for forming a ring, and
wherein when one of X or Z is a substituted or unsubstituted phenyl group and an other one of X or Z is hydrogen, Y is hydrogen, the triazine moiety and the carbazole moiety are connected through meta or para position of the phenylene group, and when a is 1 and $R_1$ is a substituted aryl group, a substituent of the substituted aryl group is selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocyclic group, when each of X and Z is a substituted or unsubstituted phenyl group, the triazine moiety and the carbazole moiety are connected through meta or para position of the phenylene group, and when a is 1 and $R_1$ is a substituted aryl group, a substituent of the substituted aryl group is selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocyclic group, when each of X and Z is a substituted or unsubstituted phenyl group, the triazine moiety and the carbazole moiety are connected through meta or para position of the phenylene group, and when $(R_1)_a$ is hydrogen, at least one $R_2$ is a heterocyclic group or a phenyl group that is substituted with a carbazole group, and when the triazine moiety and the carbazole moiety are connected through ortho position of the phenylene group,
i) at least one of X or Z is a substituted or unsubstituted carbazole group,
ii) one of X or Z is a substituted or unsubstituted phenyl group, or a substituted or unsubstituted carbazole group, and Y is a substituted or unsubstituted phenyl group,
iii) one of X or Z is a substituted or unsubstituted phenyl group, another one of X or Z is a hydrogen atom, and Y is a hydrogen atom, or
iv) d is 1 or 2, and at least one $R_2$ is a heterocyclic group.

15. The organic electroluminescence device of claim 14, wherein Z is an unsubstituted phenyl group, or a phenyl group substituted with at least one of a cyano group, a halogen atom, an alkyl group having 1 to 5 carbon atoms, or an aryl group having 6 to 15 carbon atoms for forming a ring.

16. The organic electroluminescence device of claim 14, wherein the nitrogen-containing compound represented by Formula 1 is represented by following Formula 1-1 or Formula 1-2:

Formula 1-1

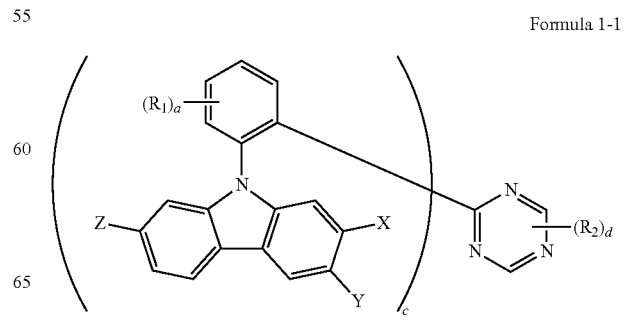

-continued
Formula 1-2
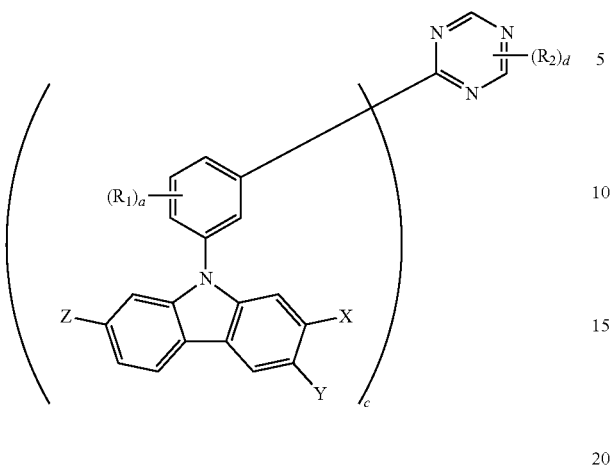
wherein in Formulae 1-1 and 1-2,
X, Y, Z, $R_1$, $R_2$, a, c and d are the same as respectively defined in Formula 1.
17. The organic electroluminescence device of claim 14, wherein the nitrogen-containing compound is one selected from compounds represented in following Compound Group 1:
Compound Group 1
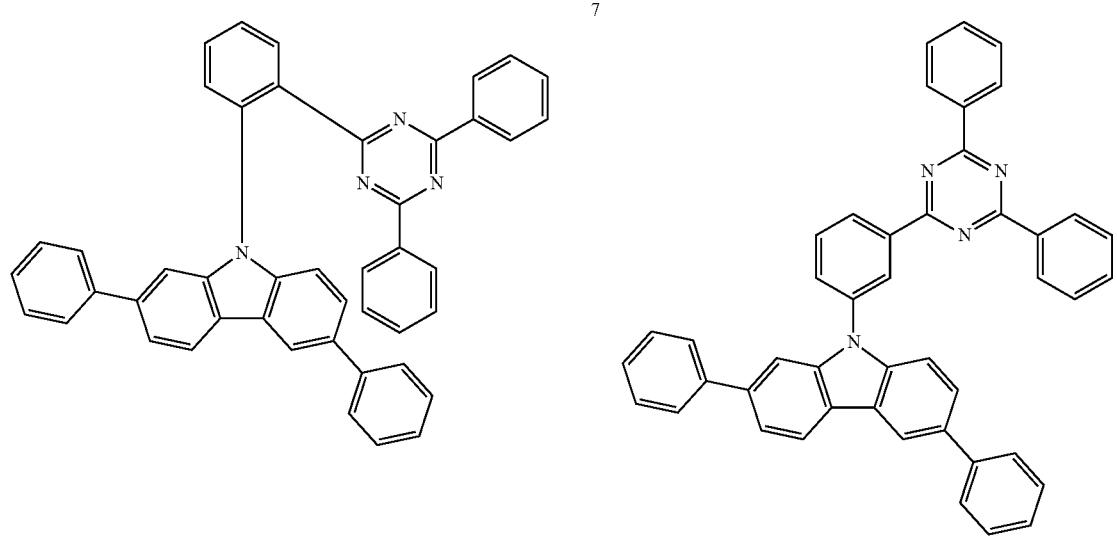

9
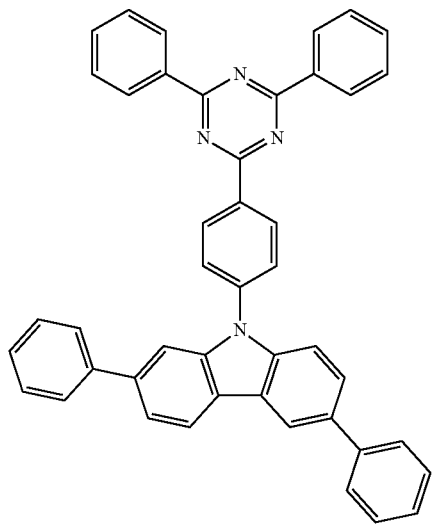
10
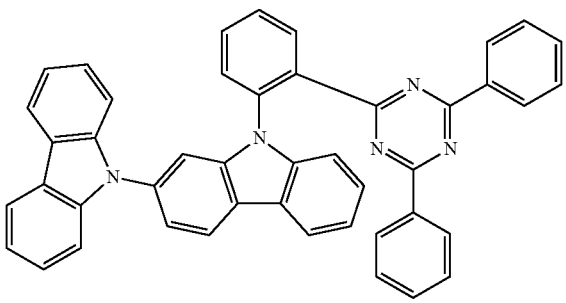
11
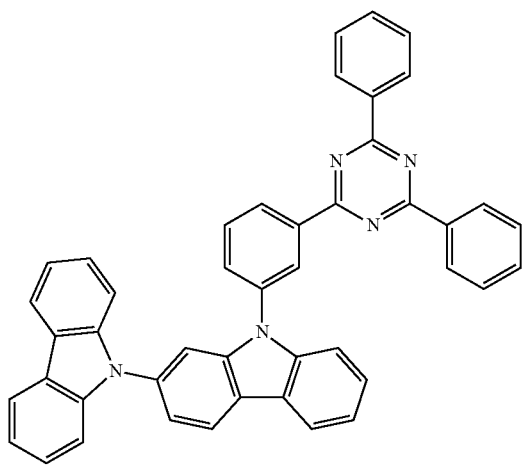
12
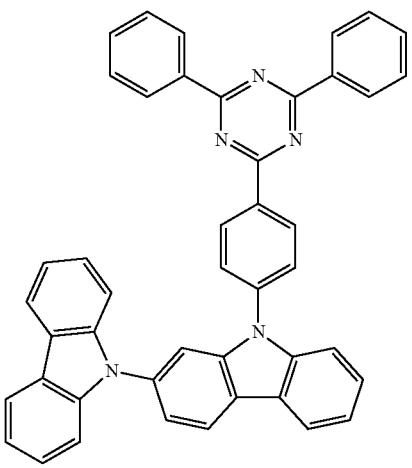
13
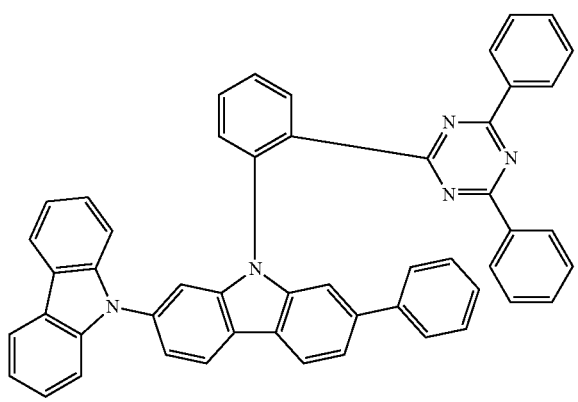
14
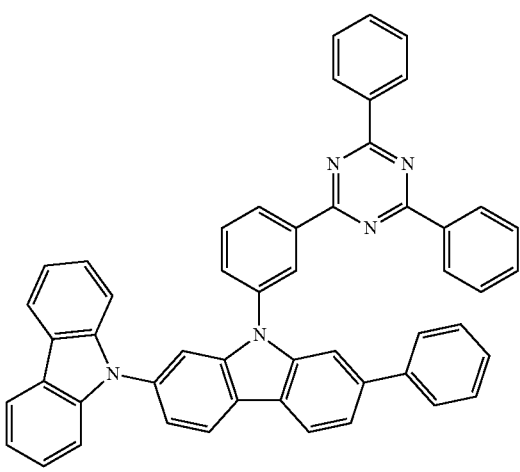

15
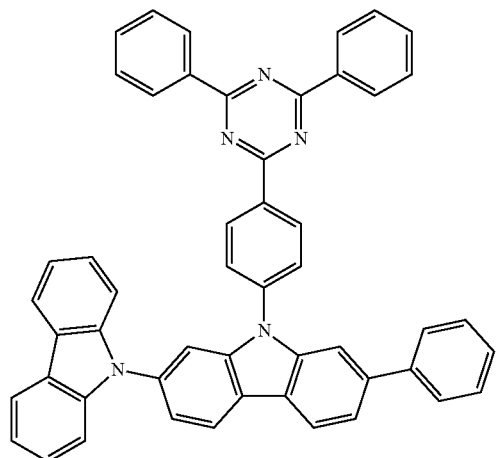
16
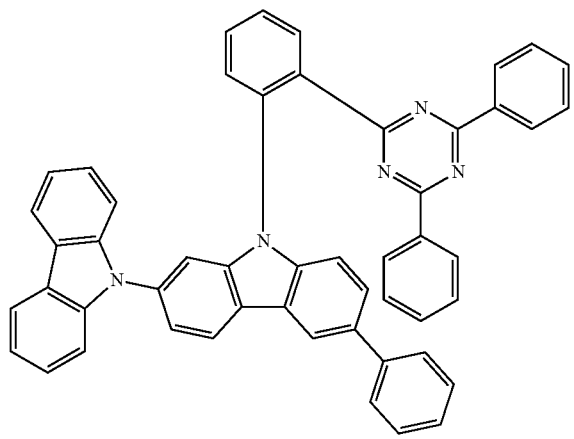
17
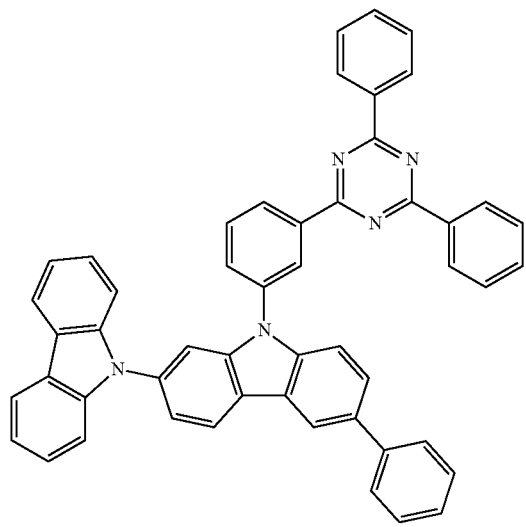
18
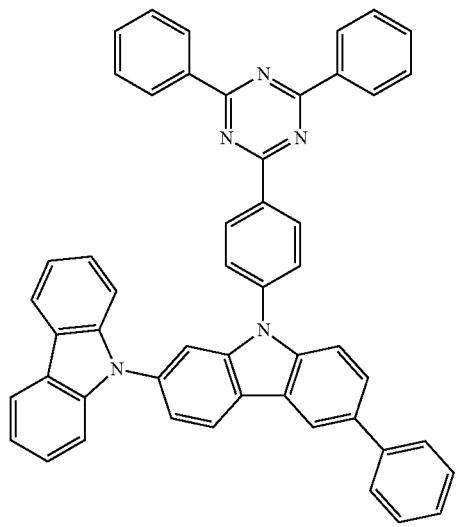
19
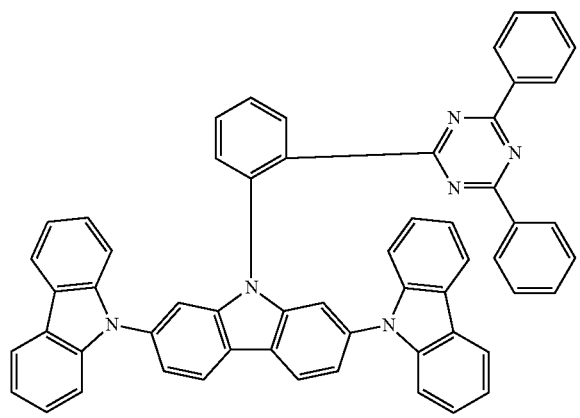
20
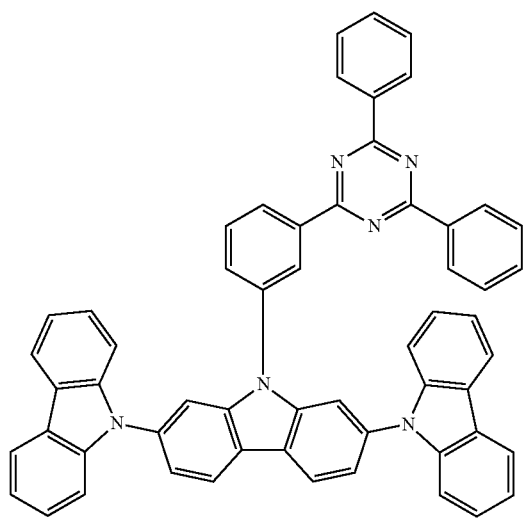

-continued
21
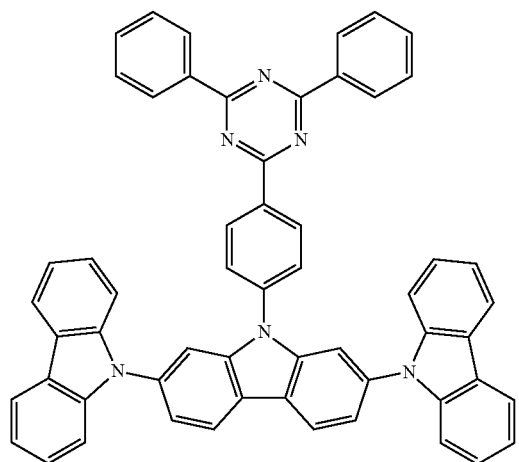
22
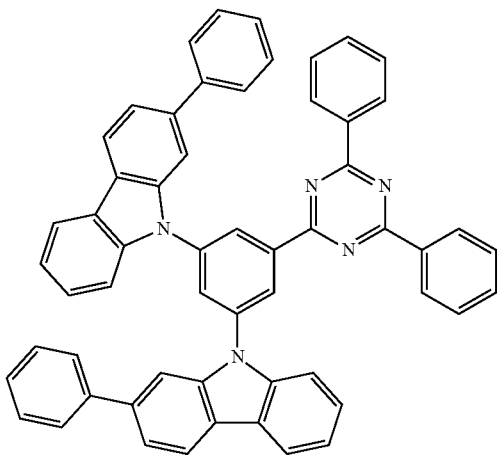
23
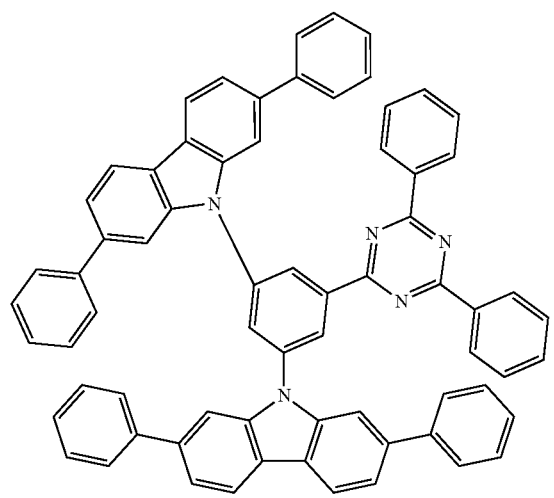
24
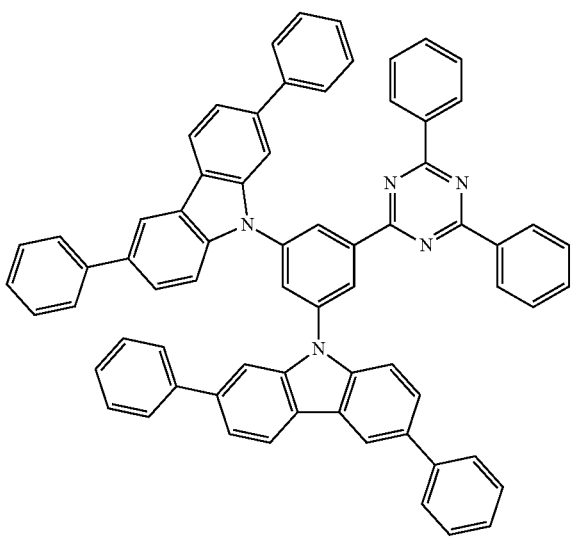
25
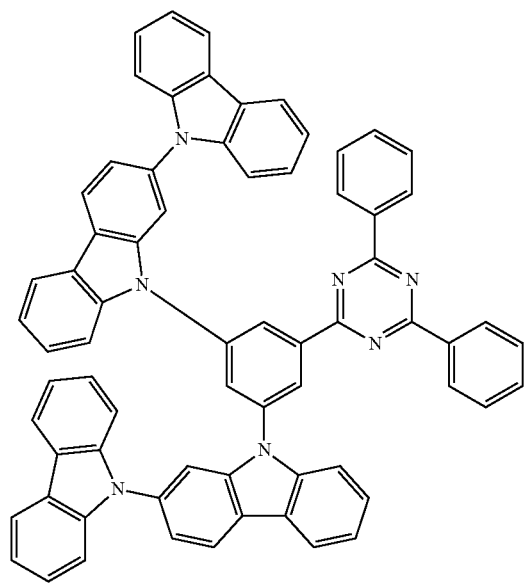
26
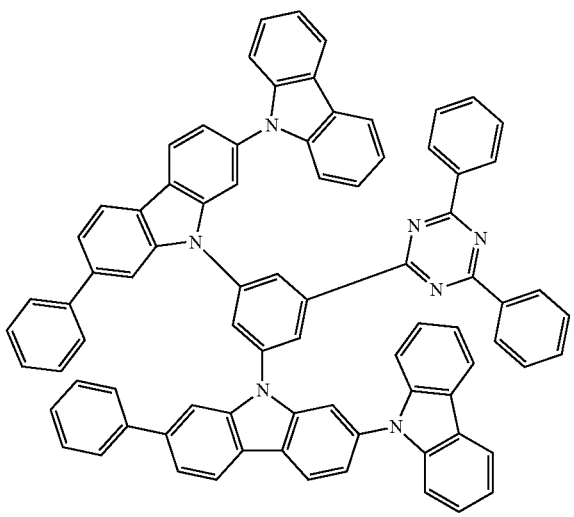

27
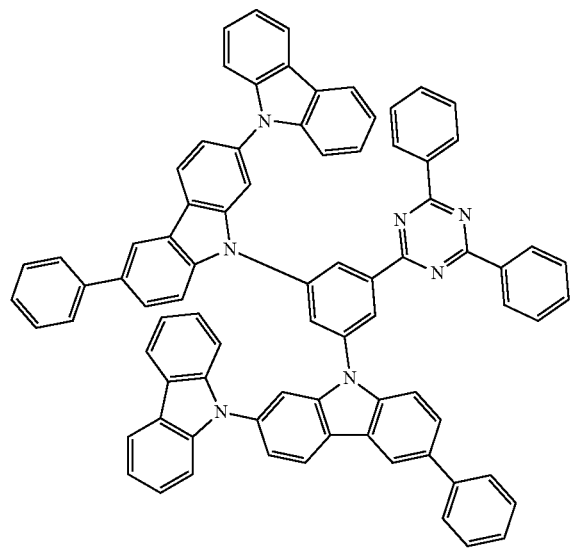
28
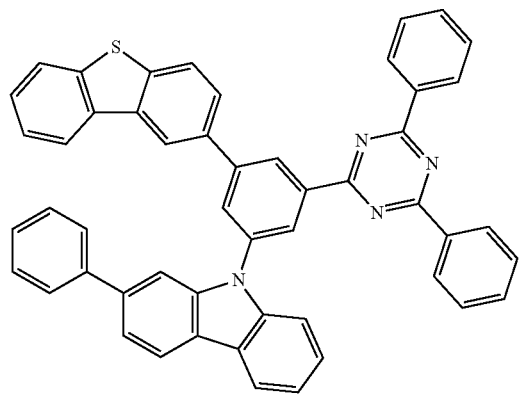
29
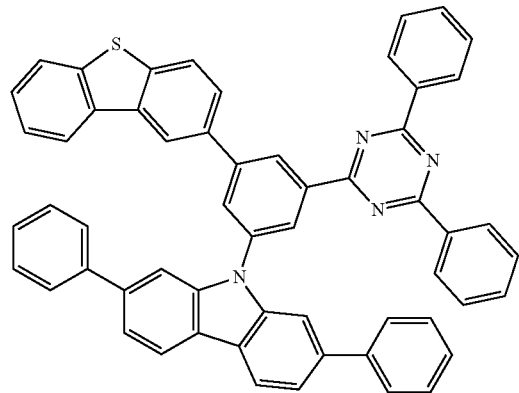
30
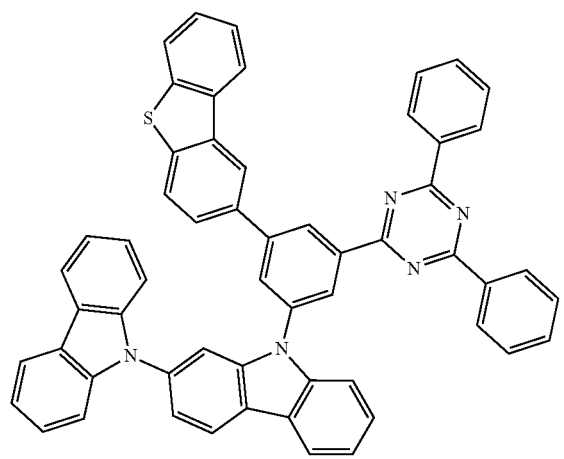
31
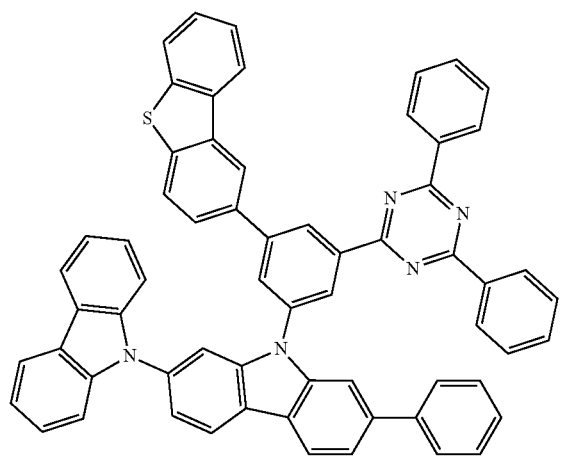
32

-continued
33
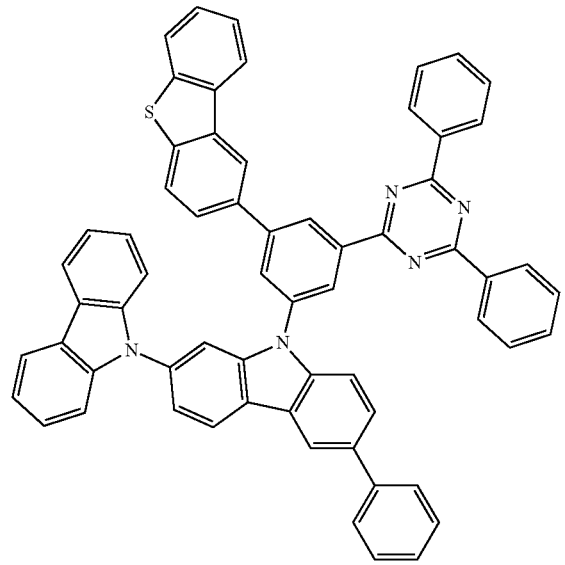
34
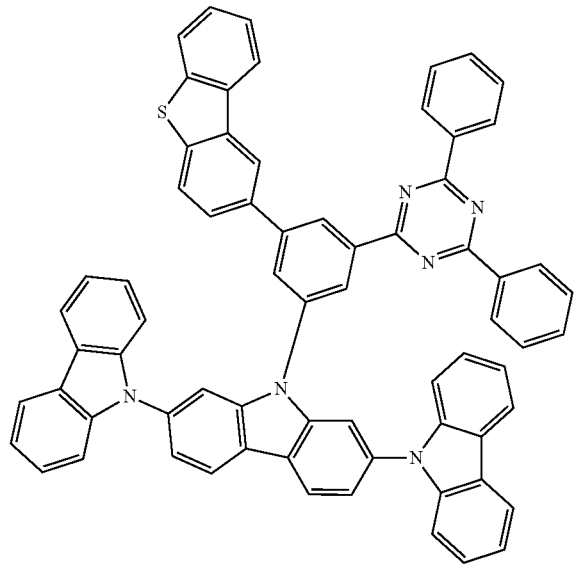
35
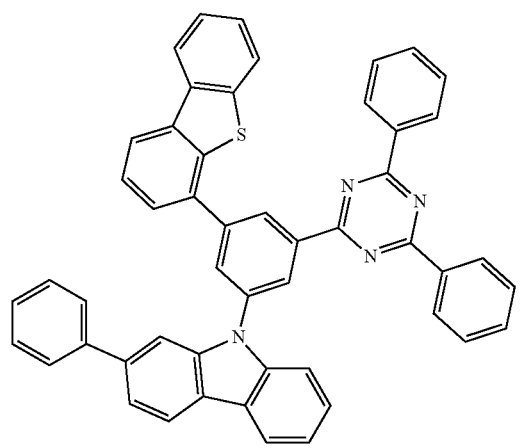
36
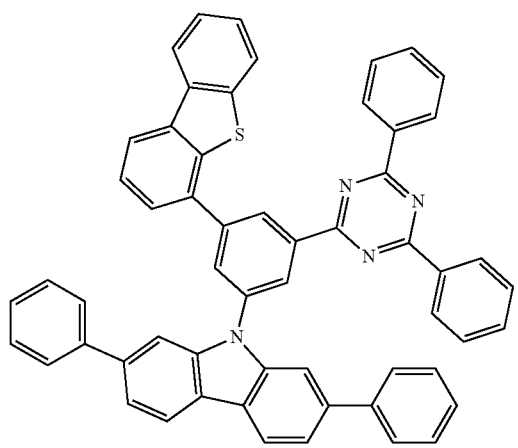
37
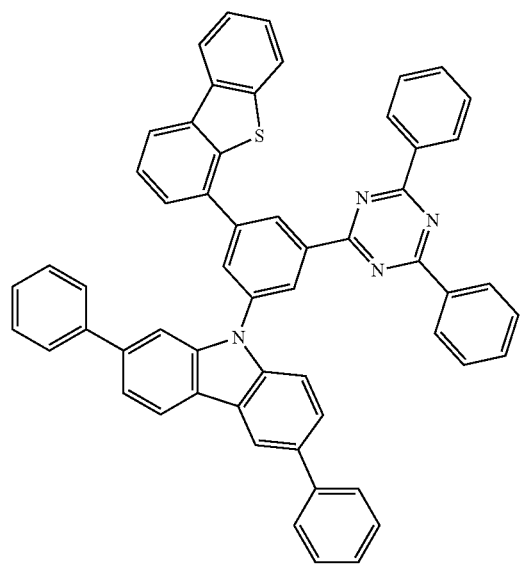
38
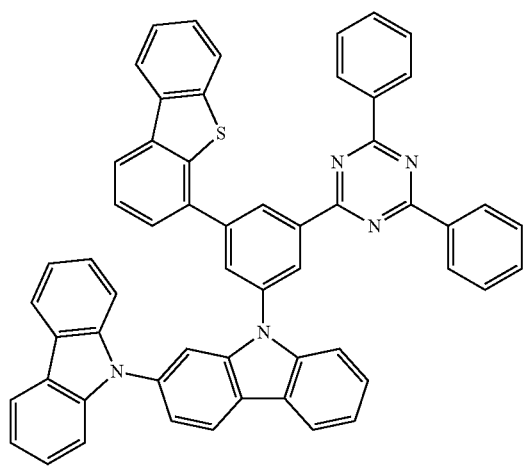

39
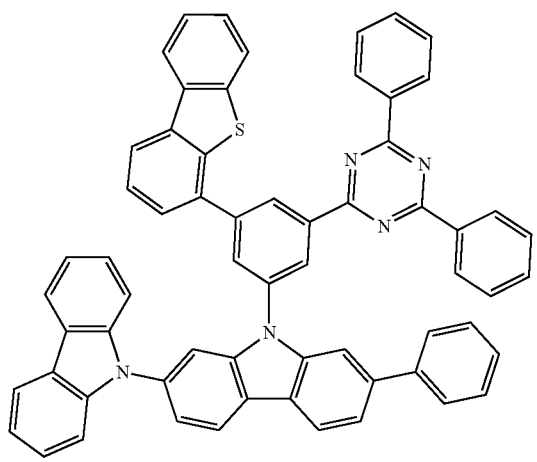
40
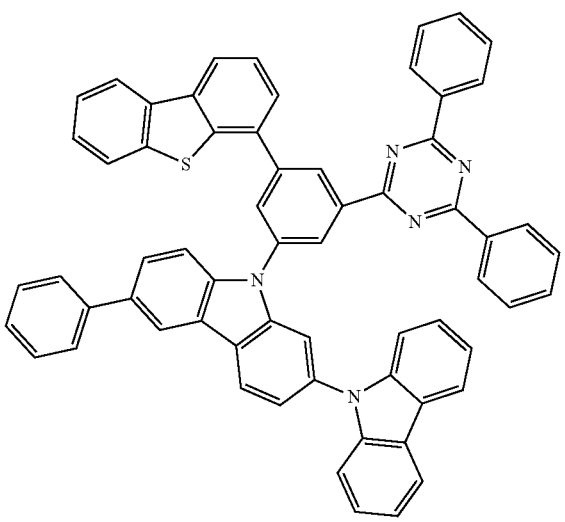
41
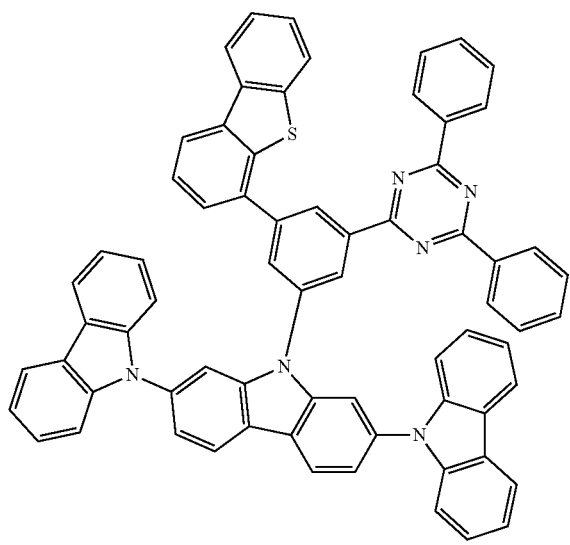
42
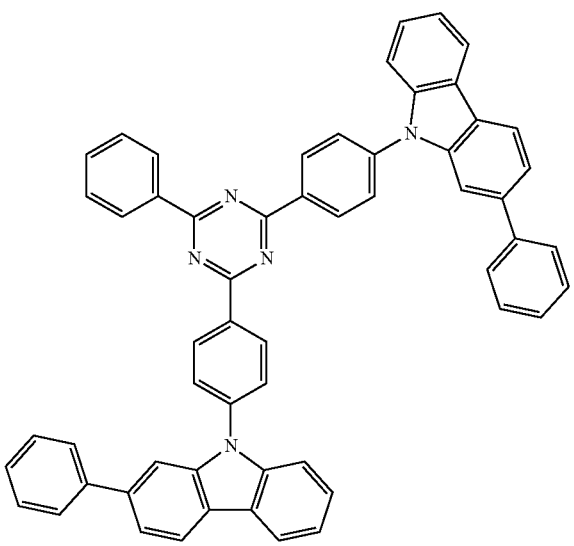
43
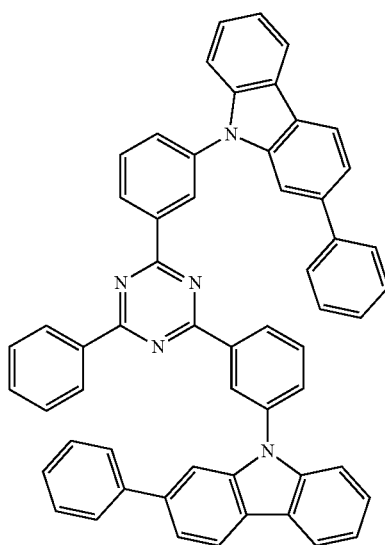

44
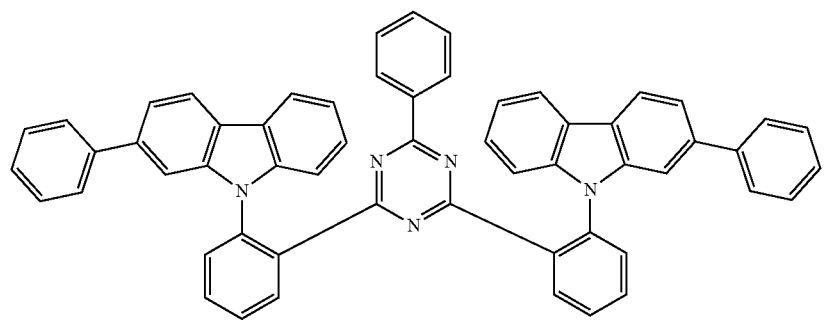
45 46
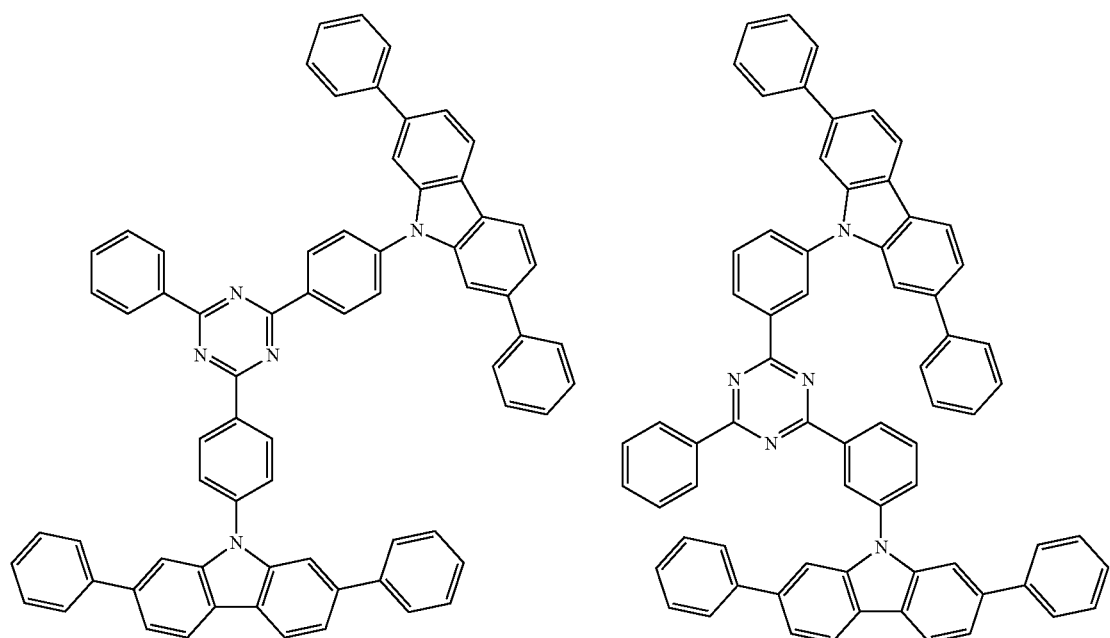
51 52
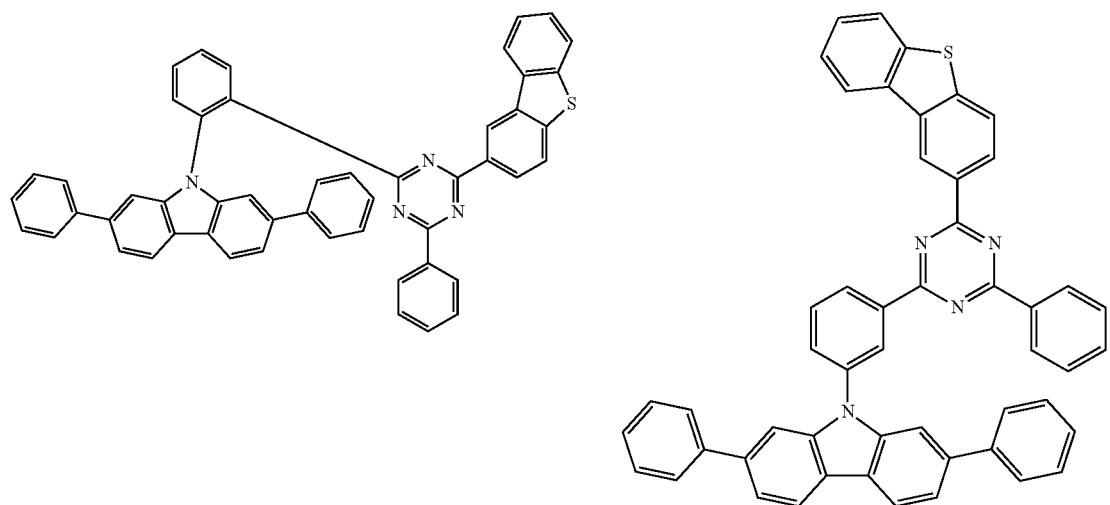

-continued
123
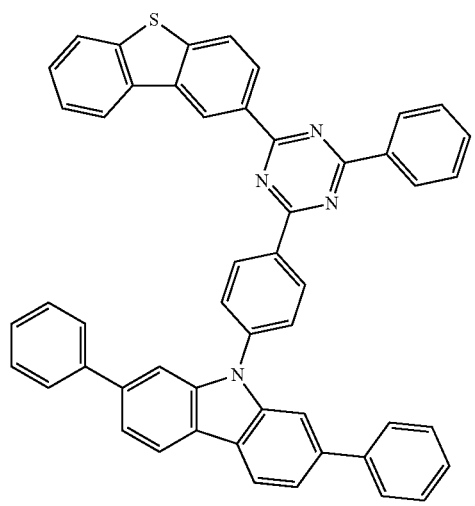
124
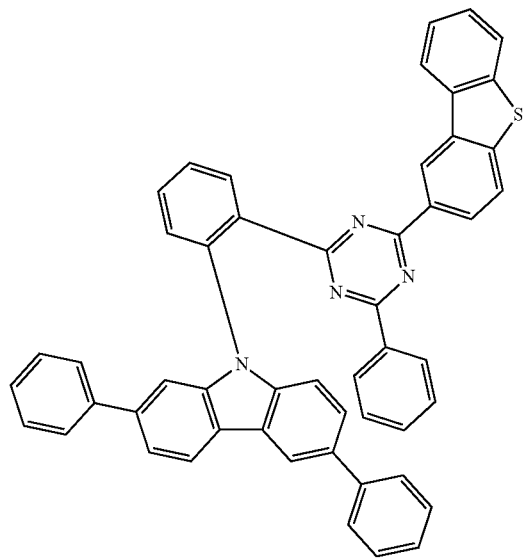
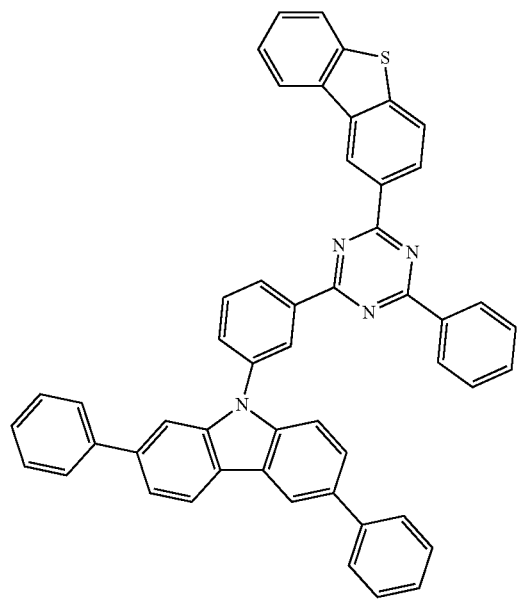
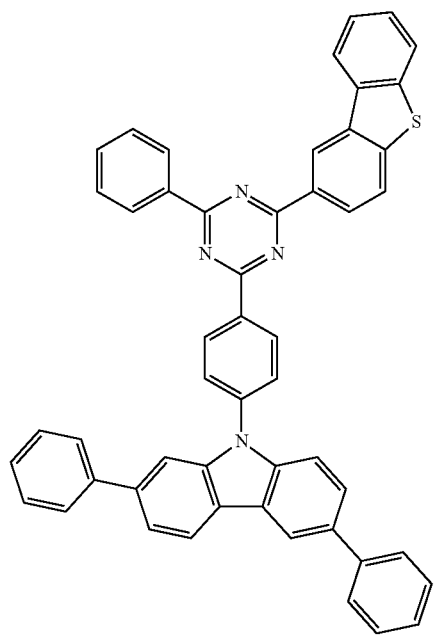

-continued
57
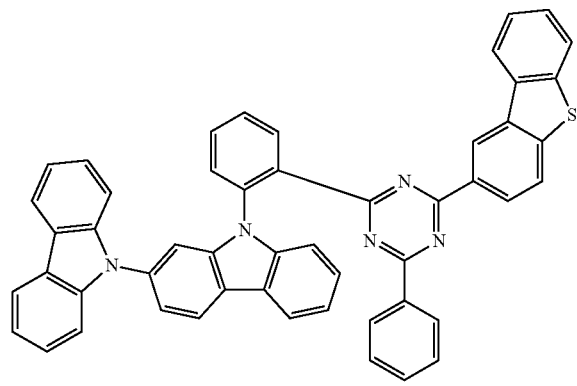
58
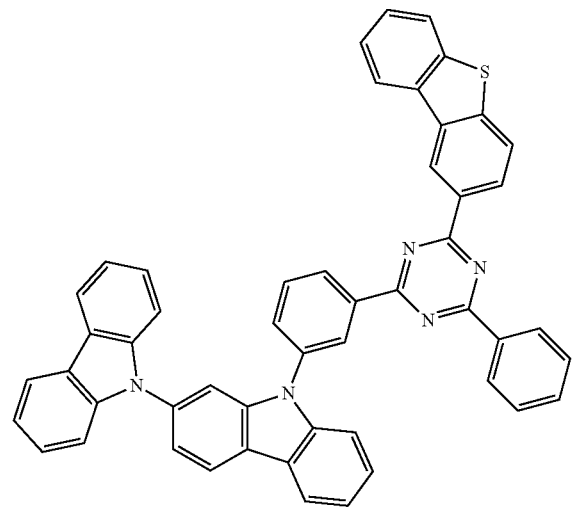
59
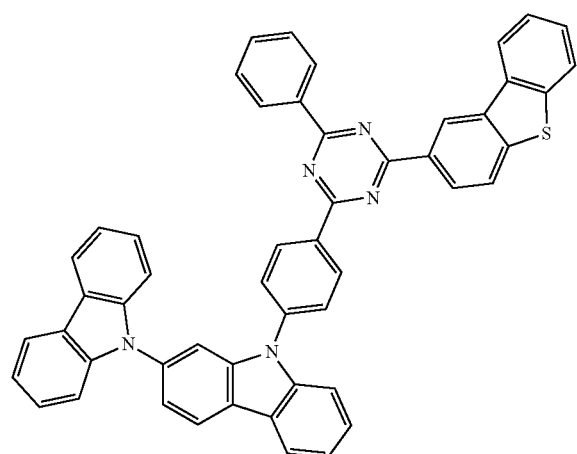
60
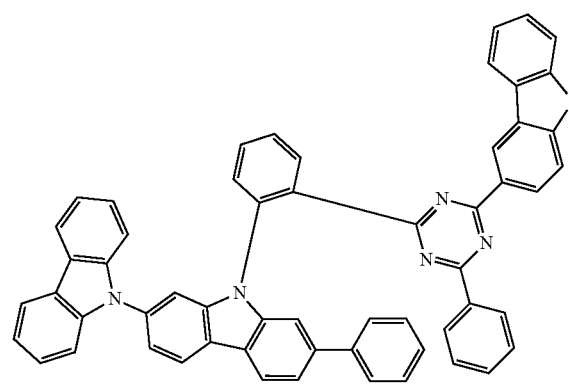
61
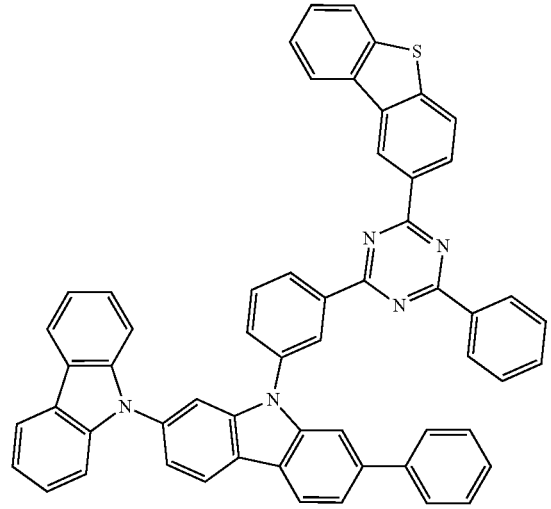
62
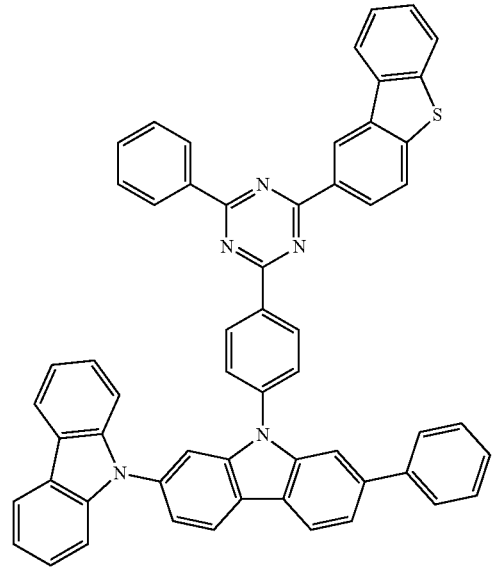

-continued
127
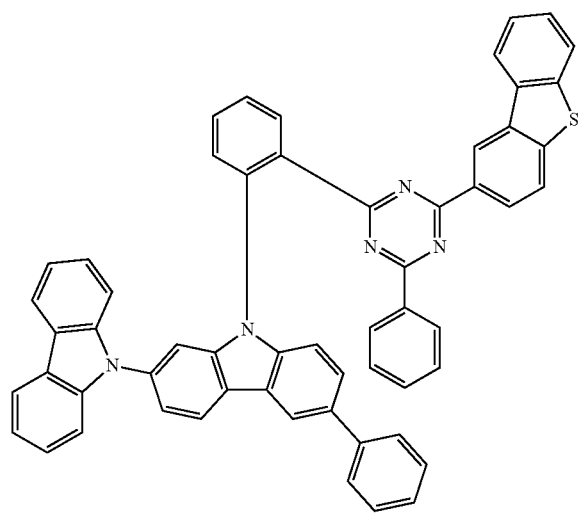
128
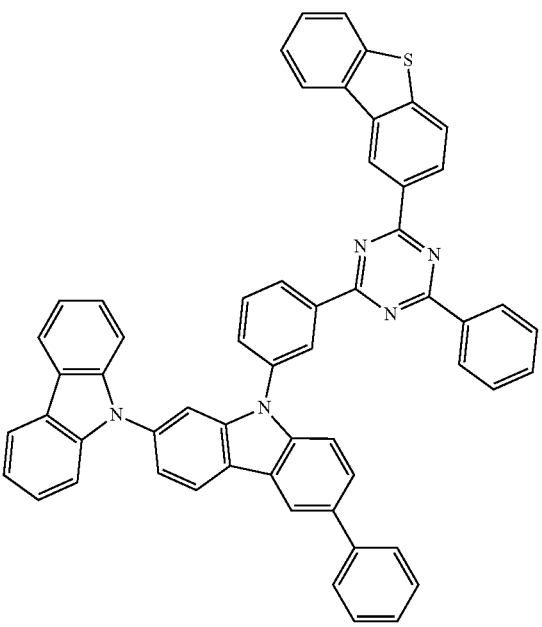
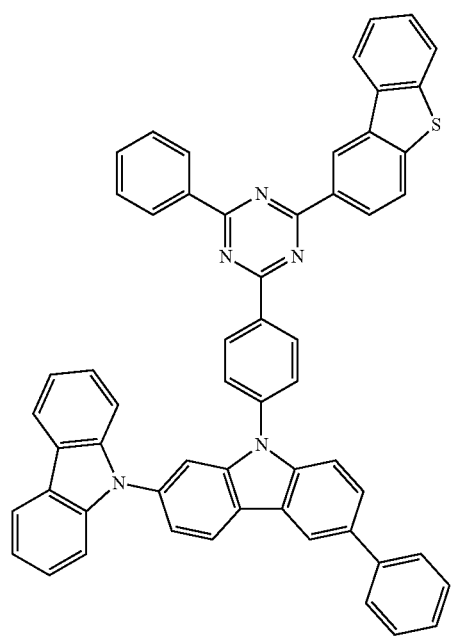
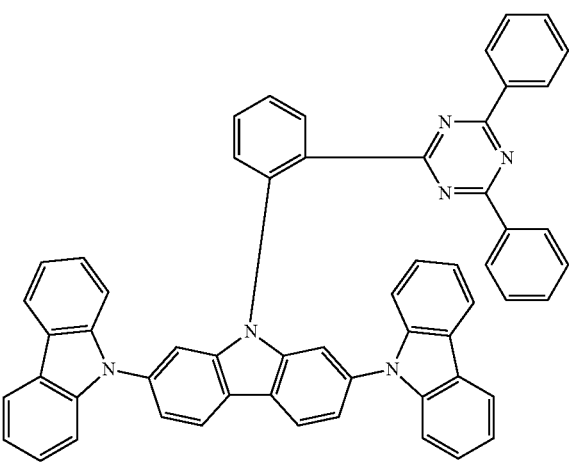

-continued
67
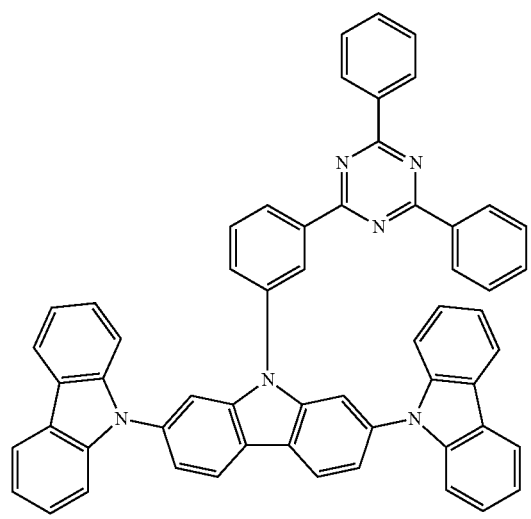
68
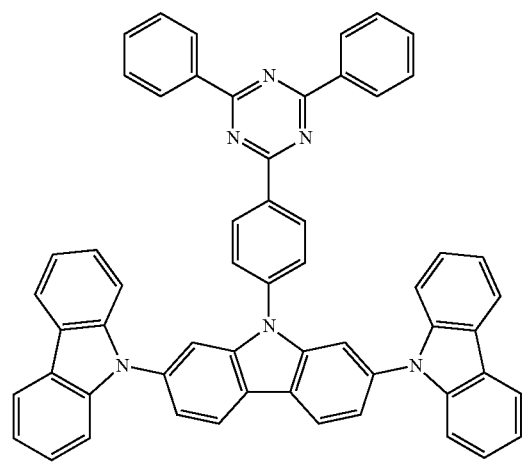
69
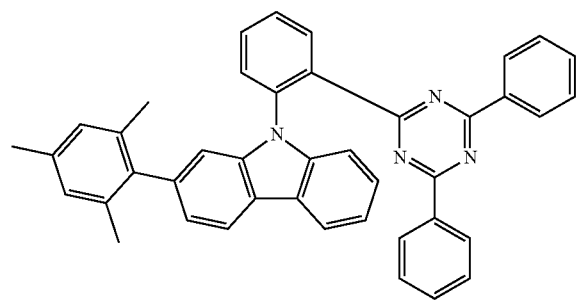
70
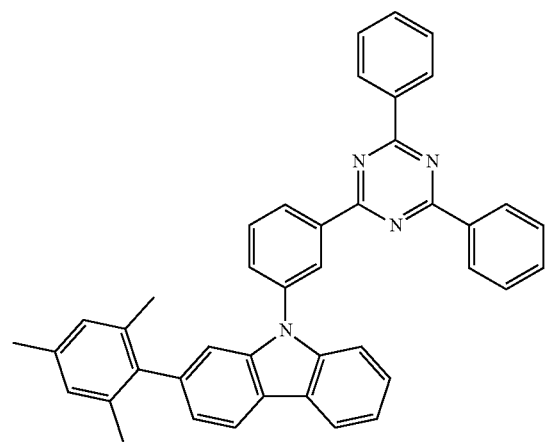
71
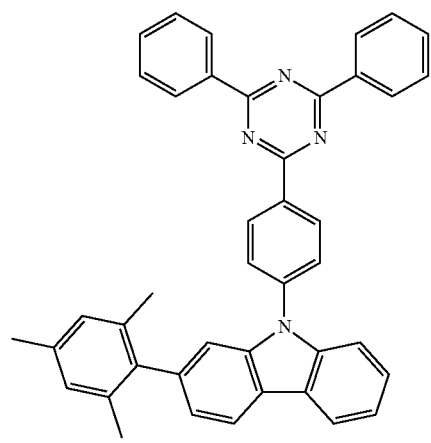
73
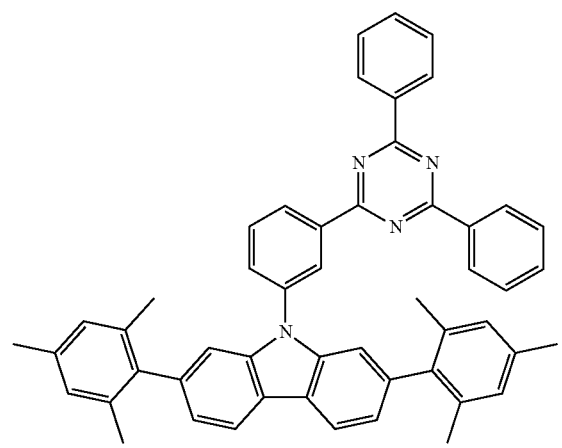

-continued
74
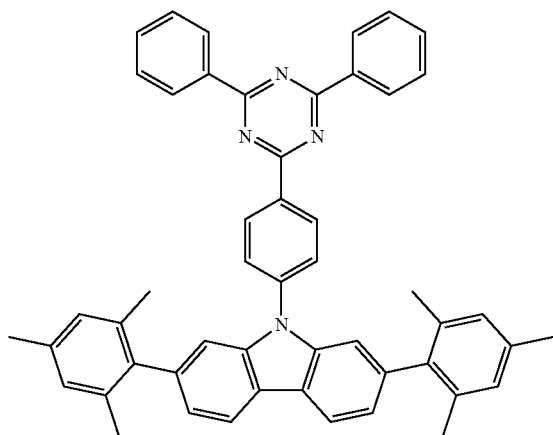
75
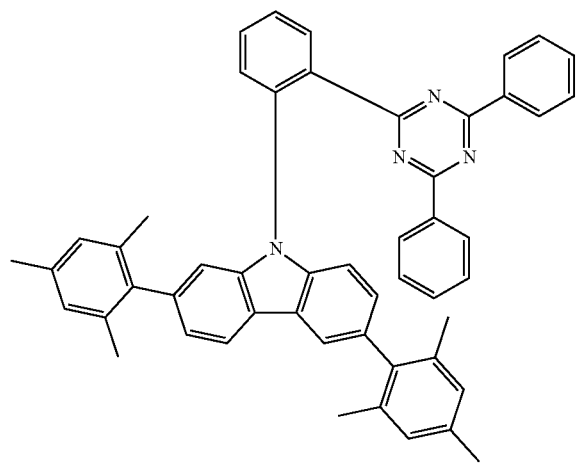
76
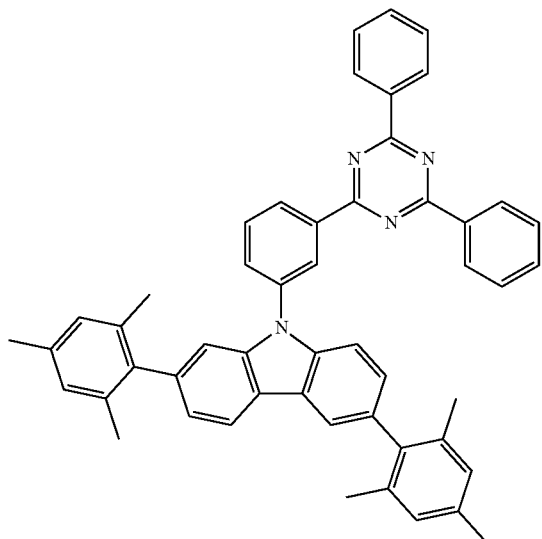
77
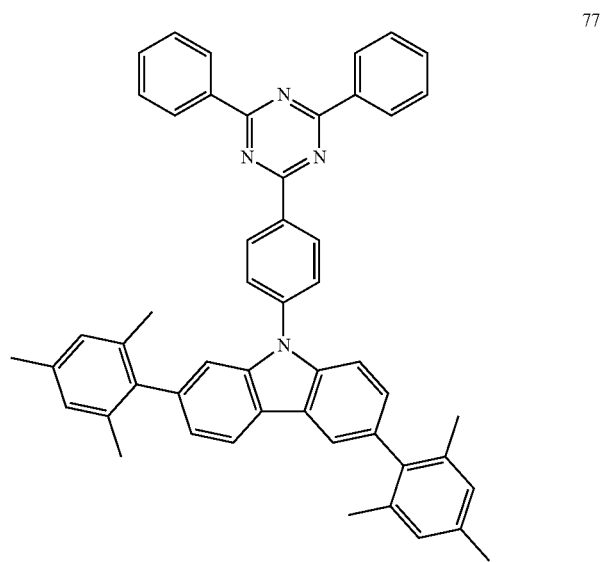
78
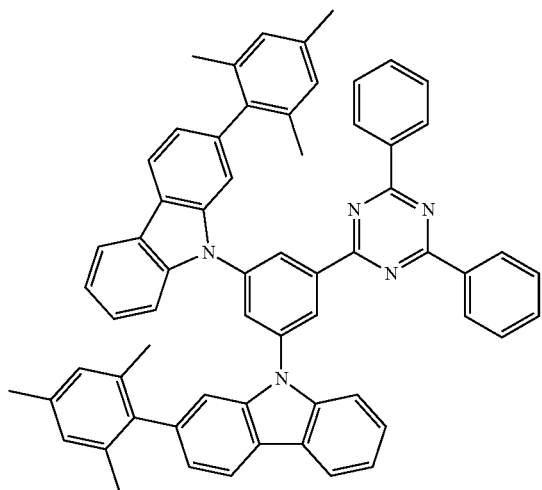
79
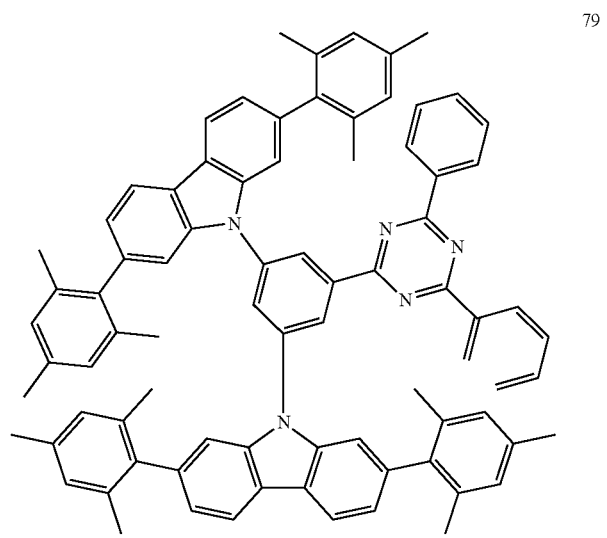

-continued
80
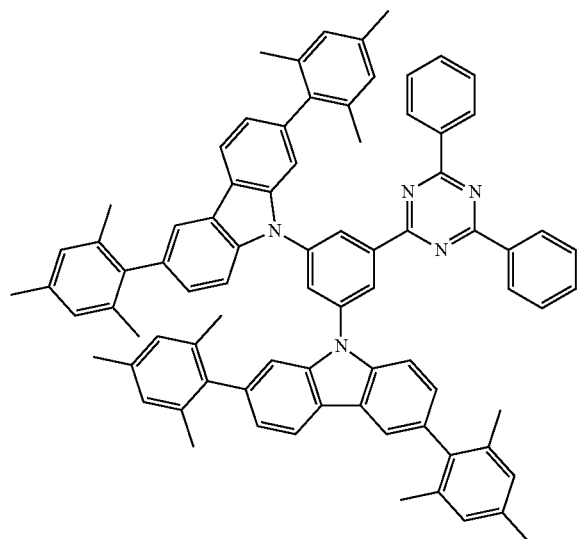
81
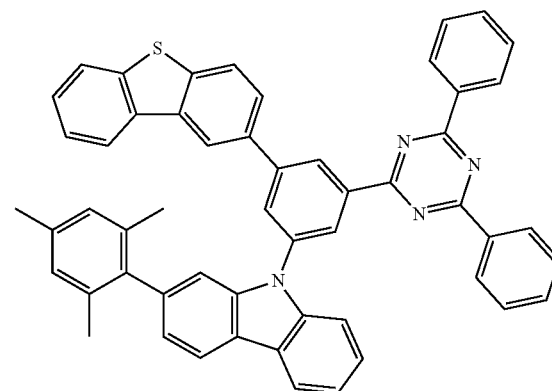
82
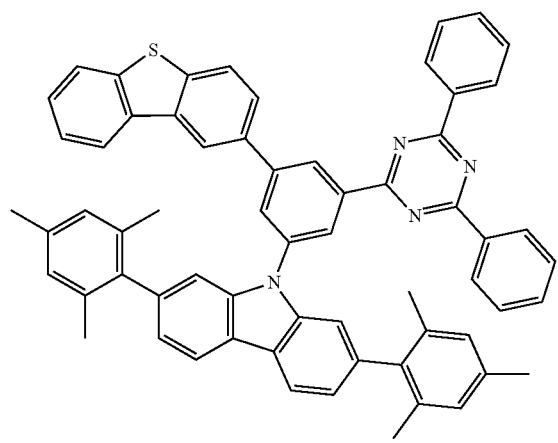
83
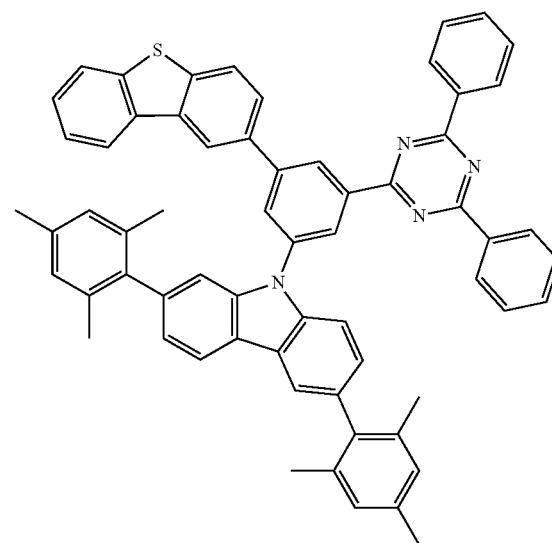

-continued
84
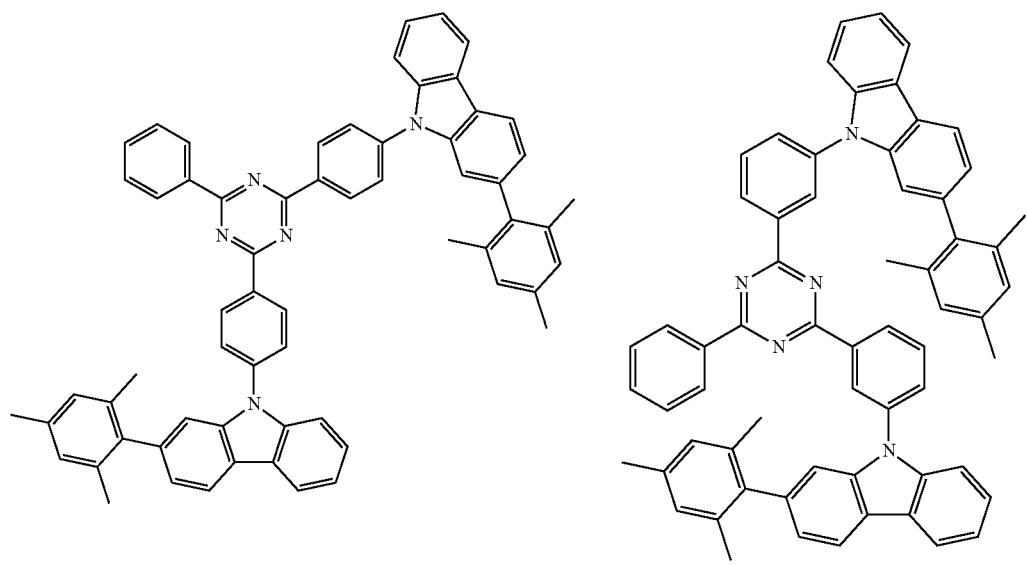
85
86
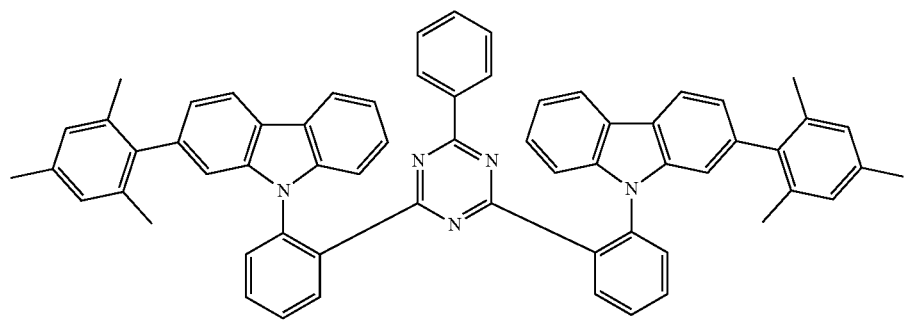
87
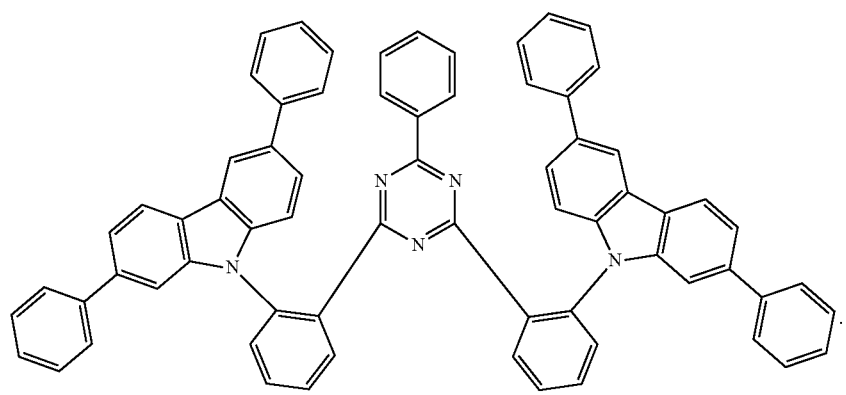

18. A nitrogen-containing compound represented by following Formula 1:

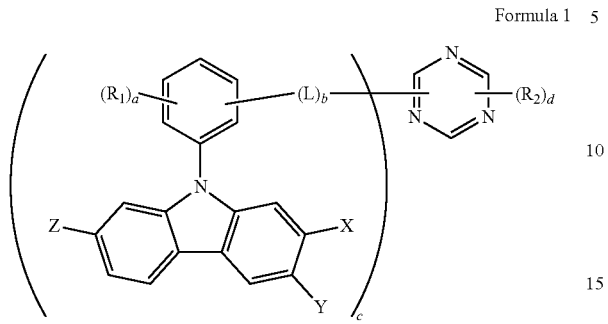

Formula 1 wherein in Formula 1,
X and Z are each independently a hydrogen atom, a deuterium atom, a substituted or unsubstituted phenyl group, or a substituted or unsubstituted carbazole group,
Y is a hydrogen atom, a deuterium atom, or a substituted or unsubstituted phenyl group,
one of X or Z is not a hydrogen atom and is not a deuterium atom, or at least two of X, Y or Z are not a hydrogen atom and is not a deuterium atom,
one of X and Y is a hydrogen atom or a deuterium atom,
$R_1$ and $R_2$ are each independently a hydrogen atom, a deuterium atom, a substituted or unsubstituted aryl group having 6 to 30 carbon atoms for forming a ring, or a substituted or unsubstituted heteroaryl group having 2 to 30 carbon atoms for forming a ring,
L is a substituted or unsubstituted arylene group having 6 to 30 carbon atoms for forming a ring, or a substituted or unsubstituted heteroarylene group having 2 to 30 carbon atoms for forming a ring,
a is an integer of 0 to 4,
b is an integer of 0 to 2,
c is 1 or 2, and
d is 1 or 2,
wherein
1) each of X and Z is independently a substituted or unsubstituted phenyl group, or a substituted or unsubstituted carbazole group,
2) one of X or Z is a substituted or unsubstituted phenyl group, or a substituted or unsubstituted carbazole group, and Y is a substituted or unsubstituted phenyl group,
3) at least one of X or Z is a substituted or unsubstituted carbazole group, or a substituted phenyl group,
4) d is 1 or 2, and at least one $R_2$ is a phenyl group that is substituted with a carbazole group, or a substituted or unsubstituted heteroaryl group having 2 to 30 carbon atoms for forming a ring, or
5) a is an integer of 1 to 4, and at least one $R_1$ is a substituted or unsubstituted aryl group having 6 to 30 carbon atoms for forming a ring, or a substituted or unsubstituted heteroaryl group having 2 to 30 carbon atoms for forming a ring, and
wherein when one of X or Z is a substituted or unsubstituted phenyl group and an other one of X or Z is hydrogen, Y is hydrogen, the triazine moiety and the carbazole moiety are connected through meta or para position of the phenylene group, and when a is 1 and $R_1$ is a substituted aryl group, a substituent of the substituted aryl group is selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocyclic group, when each of X and Z is a substituted or unsubstituted phenyl group, the triazine moiety and the carbazole moiety are connected through meta or para position of the phenylene group, and when a is 1 and $R_1$ is a substituted aryl group, a substituent of the substituted aryl group is selected from the group consisting of a deuterium atom, a halogen atom, a nitro group, an amino group, a silyl group, a boron group, a phosphine oxide group, a phosphine sulfide group, an alkyl group, an alkenyl group, an aryl group, and a heterocyclic group, when each of X and Z is a substituted or unsubstituted phenyl group, the triazine moiety and the carbazole moiety are connected through meta or para position of the phenylene group, and when $(R_1)_a$ is hydrogen, at least one $R_2$ is a heterocyclic group or a phenyl group that is substituted with a carbazole group, and when the triazine moiety and the carbazole moiety are connected through ortho position of the phenylene group,
i) at least one of X or Z is a substituted or unsubstituted carbazole group,
ii) one of X or Z is a substituted or unsubstituted phenyl group, or a substituted or unsubstituted carbazole group, and Y is a substituted or unsubstituted phenyl group,
iii) one of X or Z is a substituted or unsubstituted phenyl group, another one of X or Z is a hydrogen atom, and Y is a hydrogen atom, or
iv) d is 1 or 2, and at least one $R_2$ is a heterocyclic group.

19. The nitrogen-containing compound of claim 18, wherein Z is an unsubstituted phenyl group, or a phenyl group substituted with at least one of a cyano group, a halogen atom, an alkyl group having 1 to 5 carbon atoms, or an aryl group having 6 to 15 carbon atoms for forming a ring.

20. The nitrogen-containing compound of claim 18, wherein the nitrogen-containing compound represented by Formula 1 is represented by following Formula 1-1 or Formula 1-2:

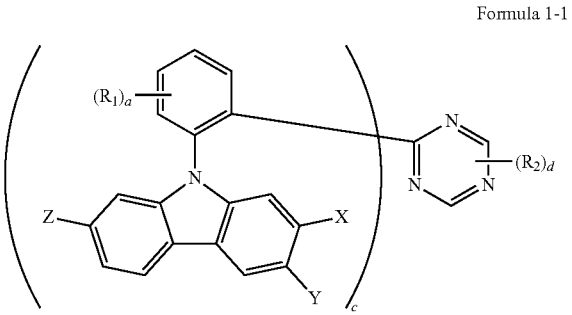

Formula 1-1

-continued
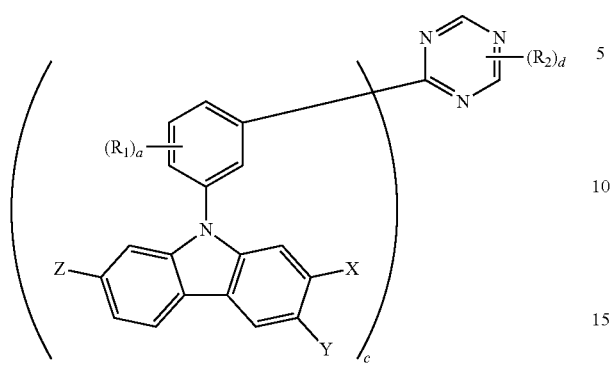
Formula 1-2
wherein in Formulae 1-1 and 1-2,
X, Y, Z, $R_1$, $R_2$, a, c and d are the same as respectively defined in Formula 1.
21. The nitrogen-containing compound of claim 18, wherein the nitrogen-containing compound is one selected from compounds represented in following Compound Group 1:
Compound Group 1
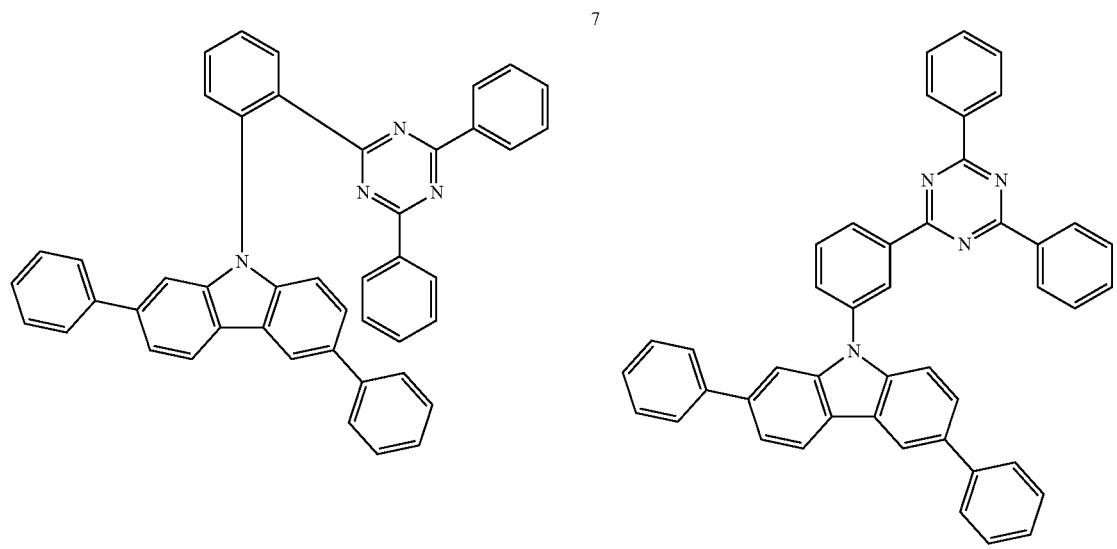

-continued
9
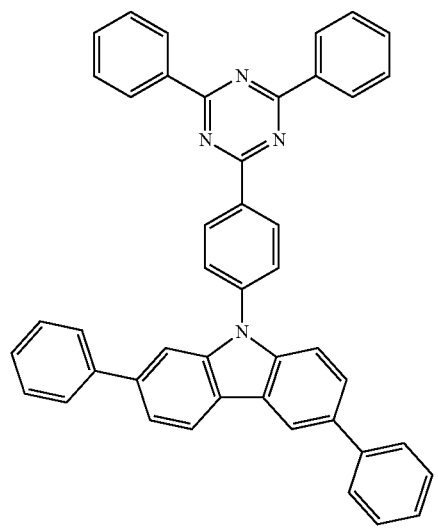
10
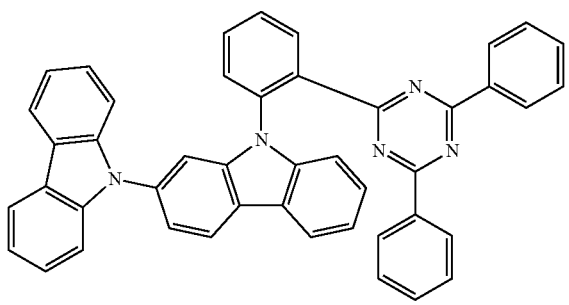
11
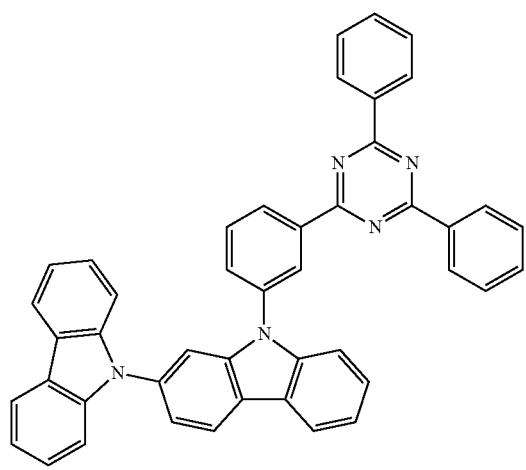
12
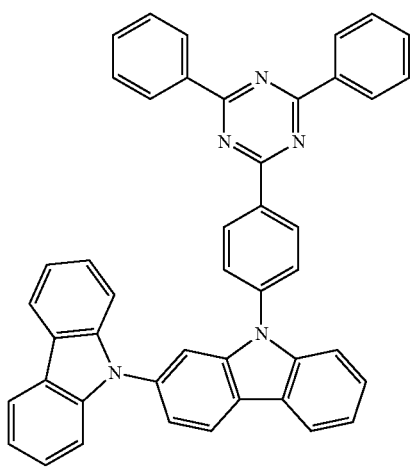
13
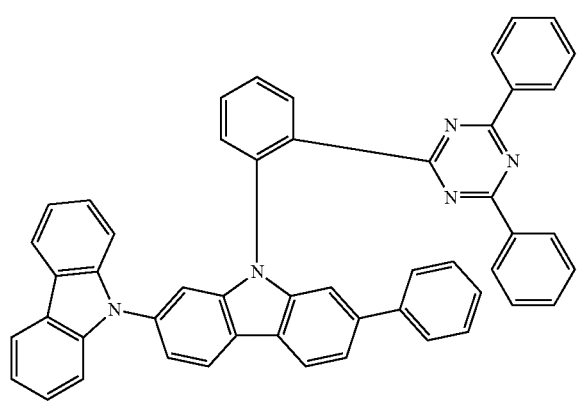
14
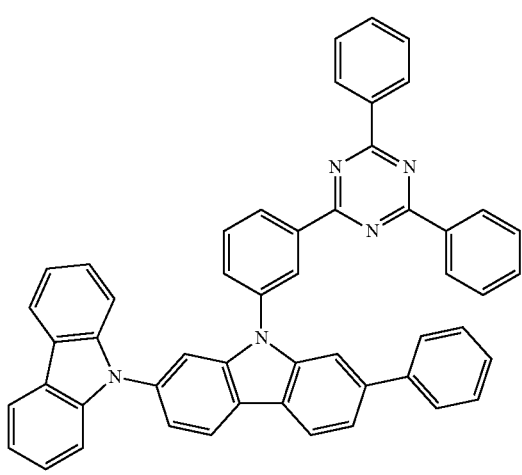

-continued
15
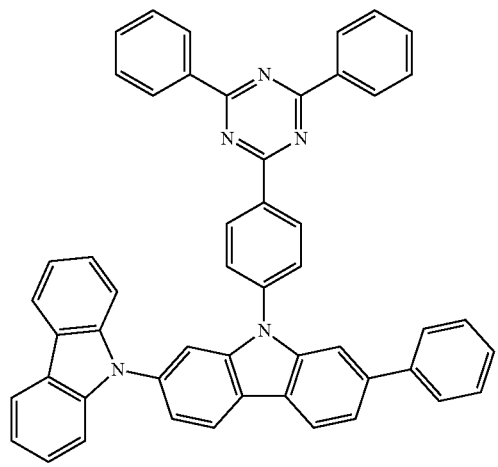
16
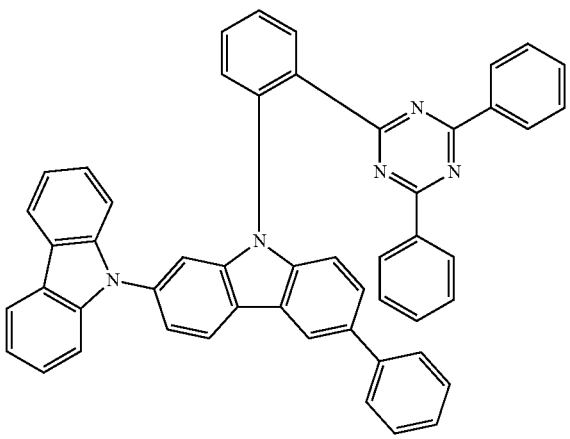
17
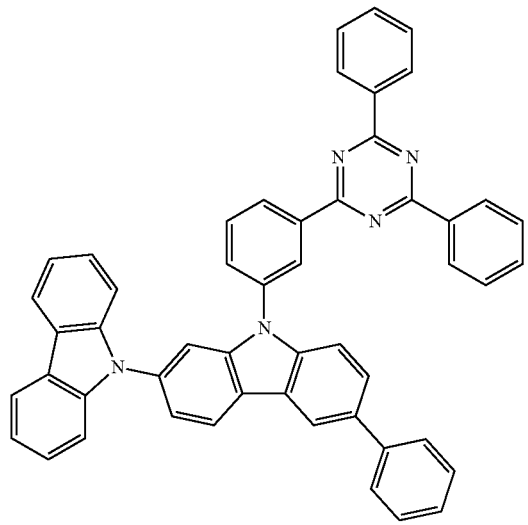
18
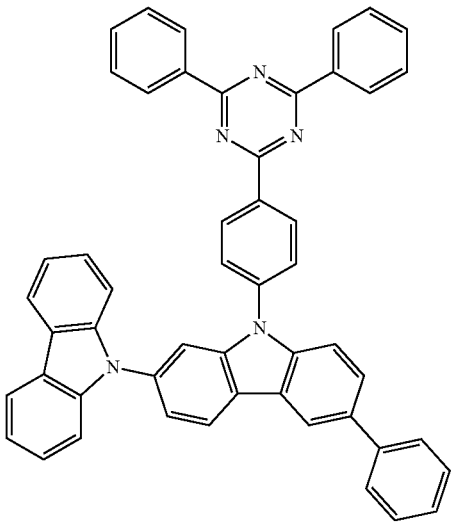
19
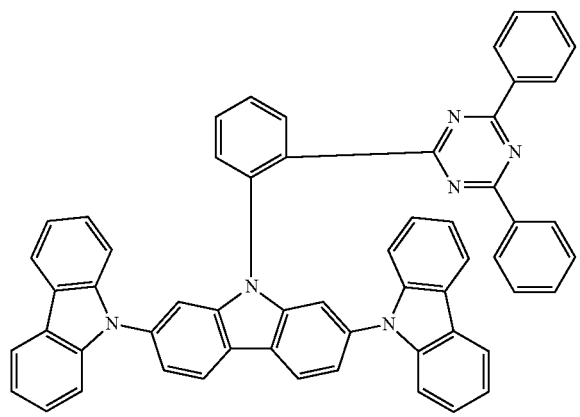
20
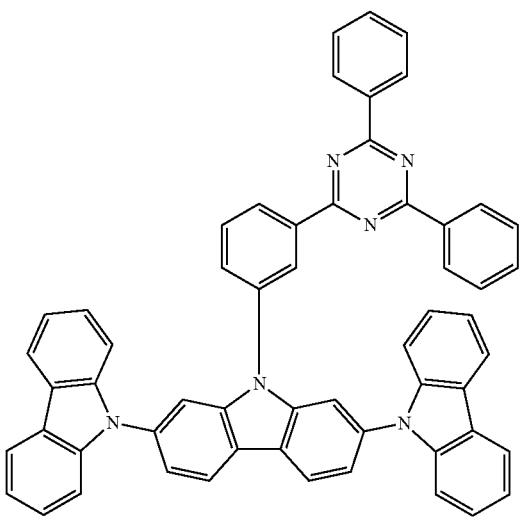

-continued
21
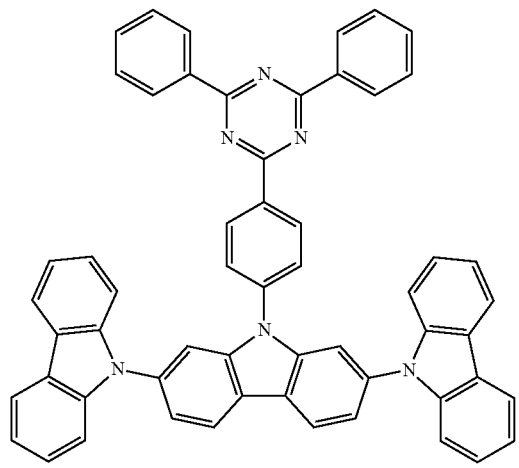
22
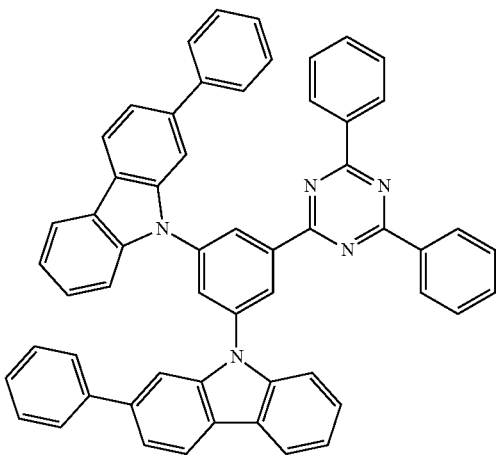
23
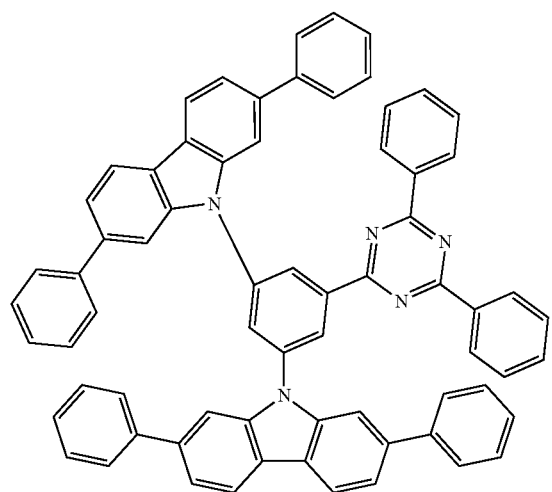
24
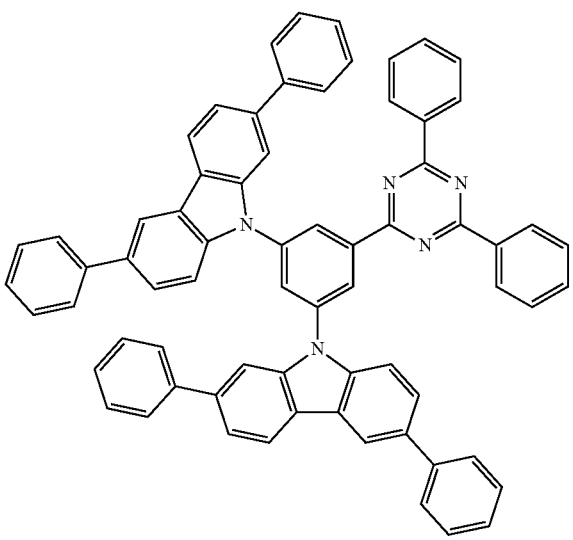
25
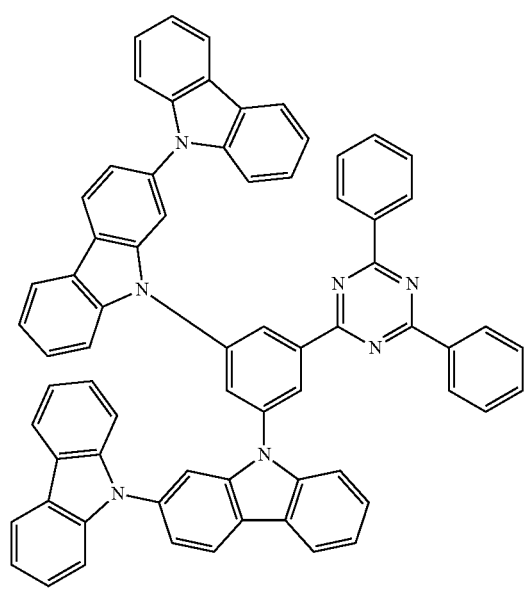
26
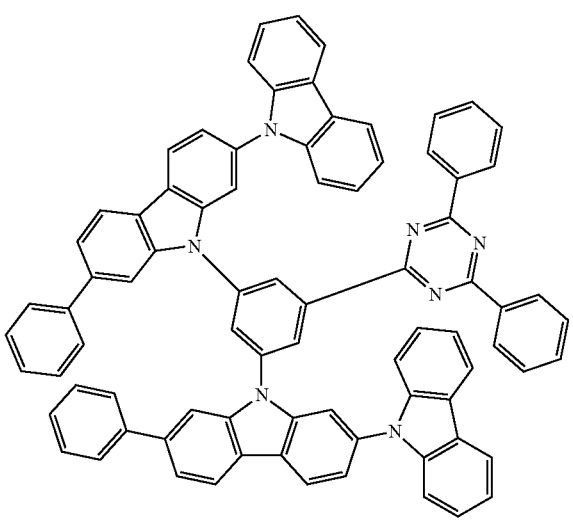

-continued
27
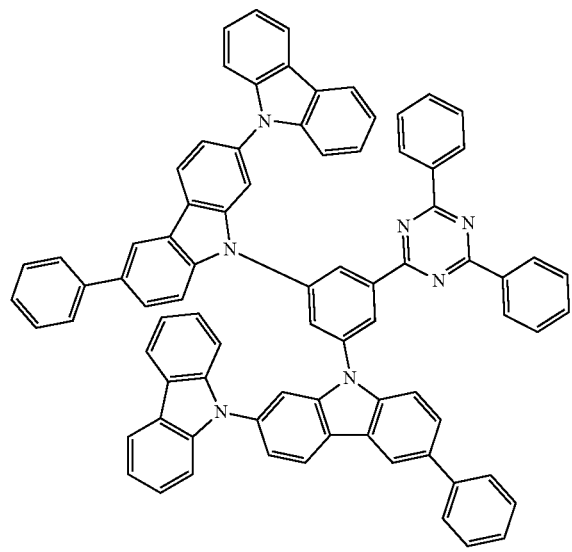
28
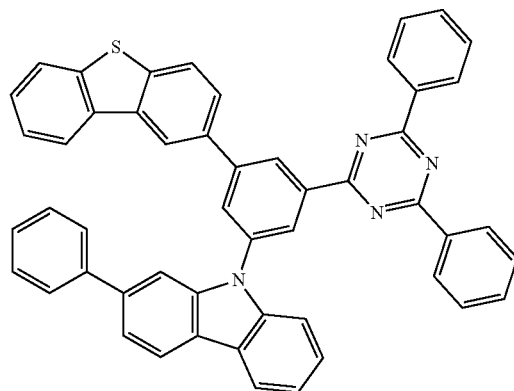
29
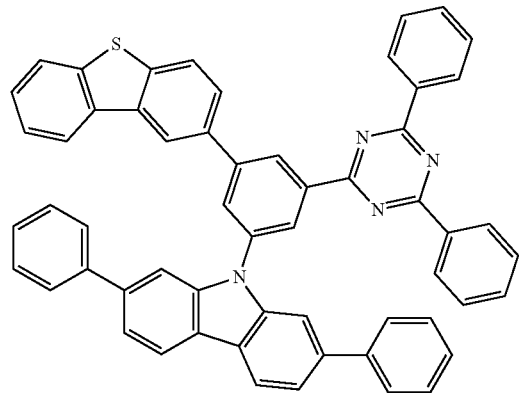
30
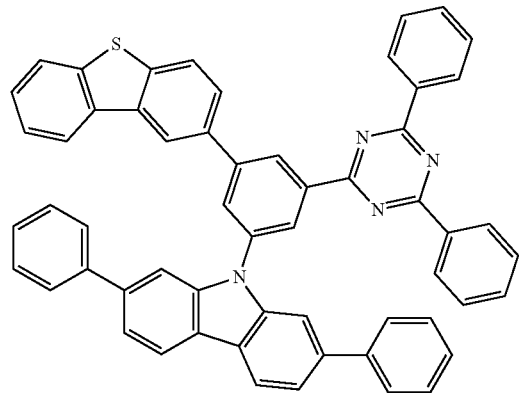
31
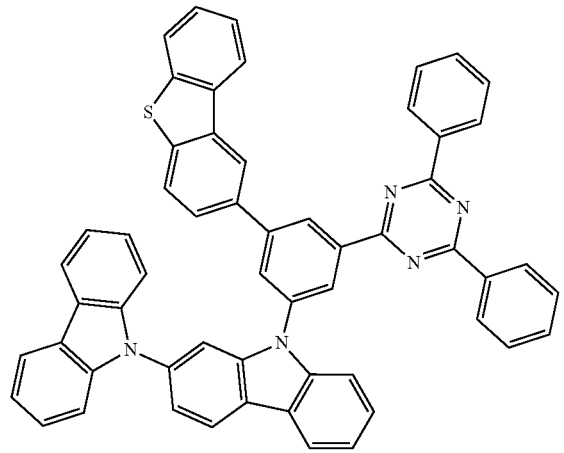
32
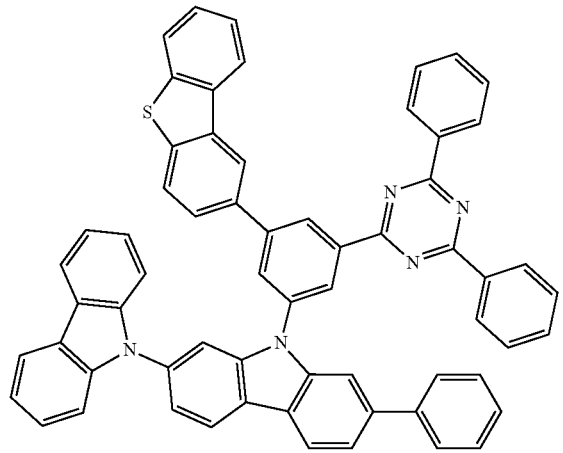

-continued
33
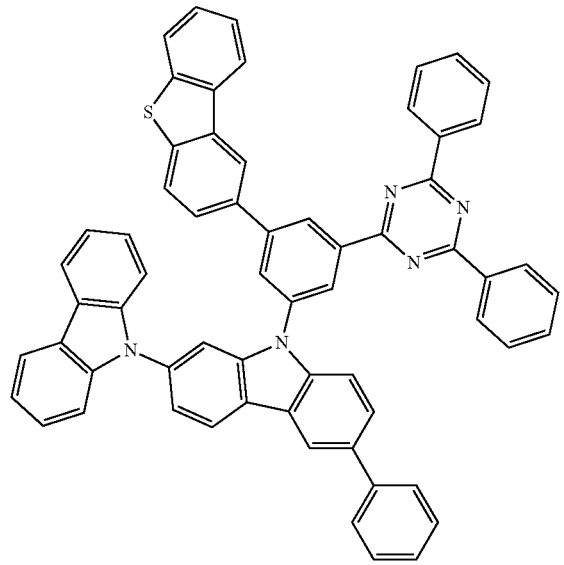
34
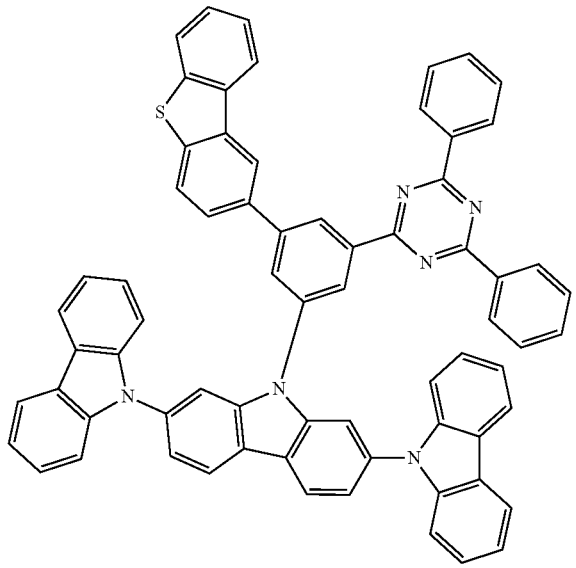
35
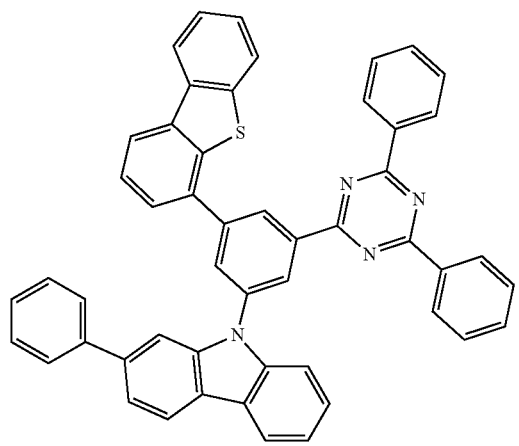
36
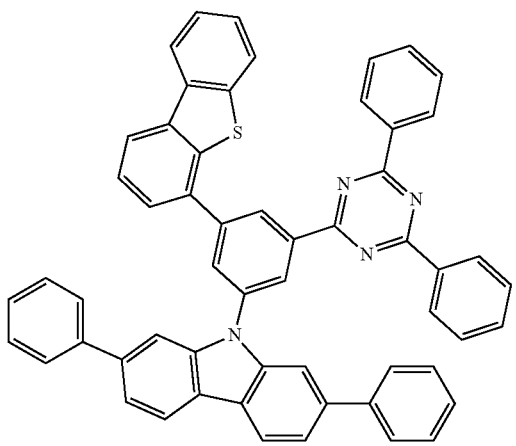
37
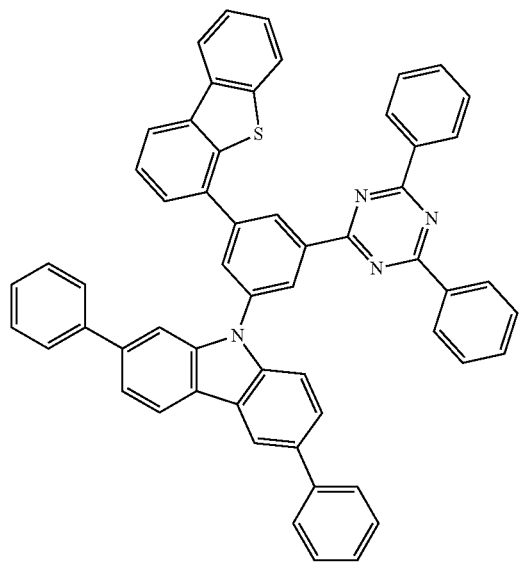
38
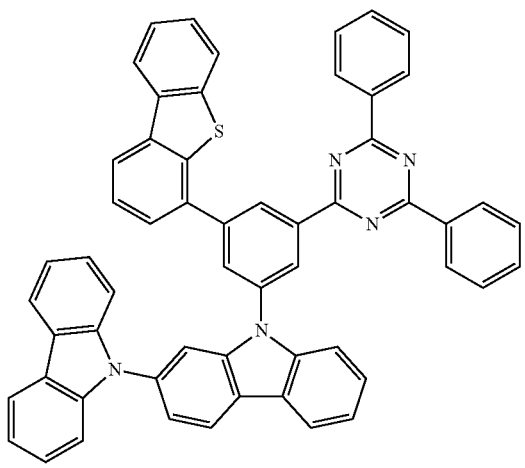

-continued
39
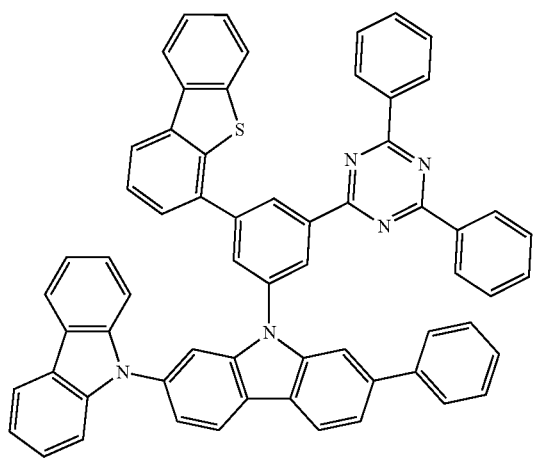
40
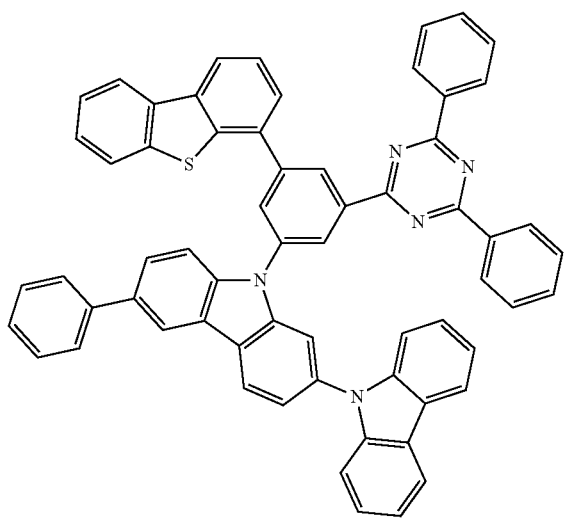
41
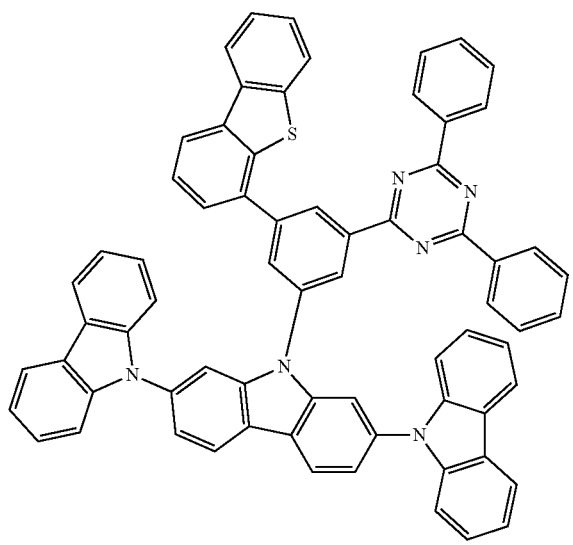
42
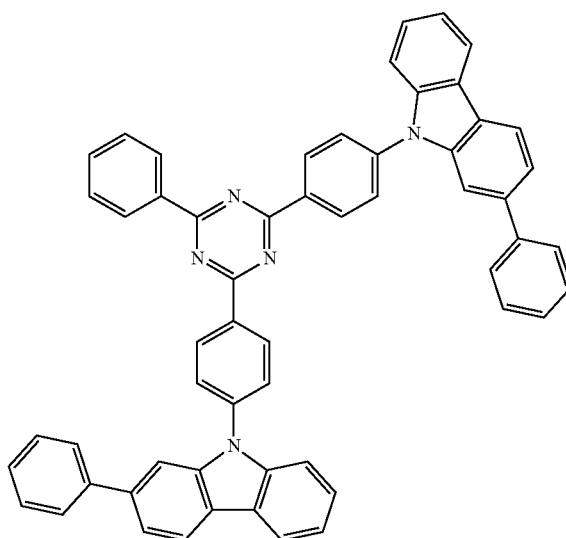
43
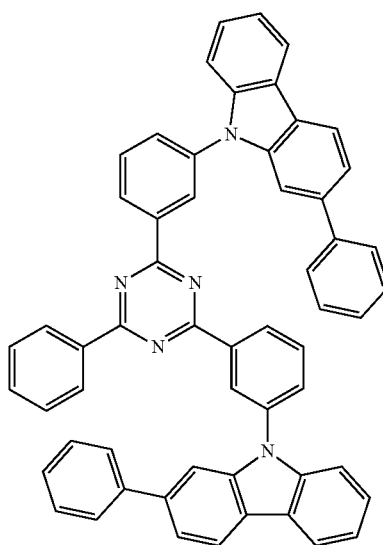

44
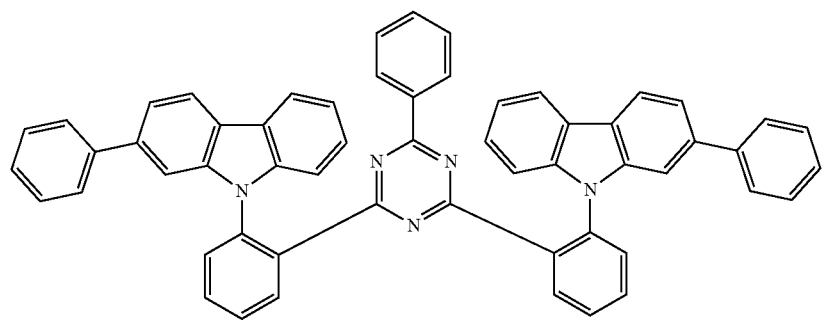
45 46
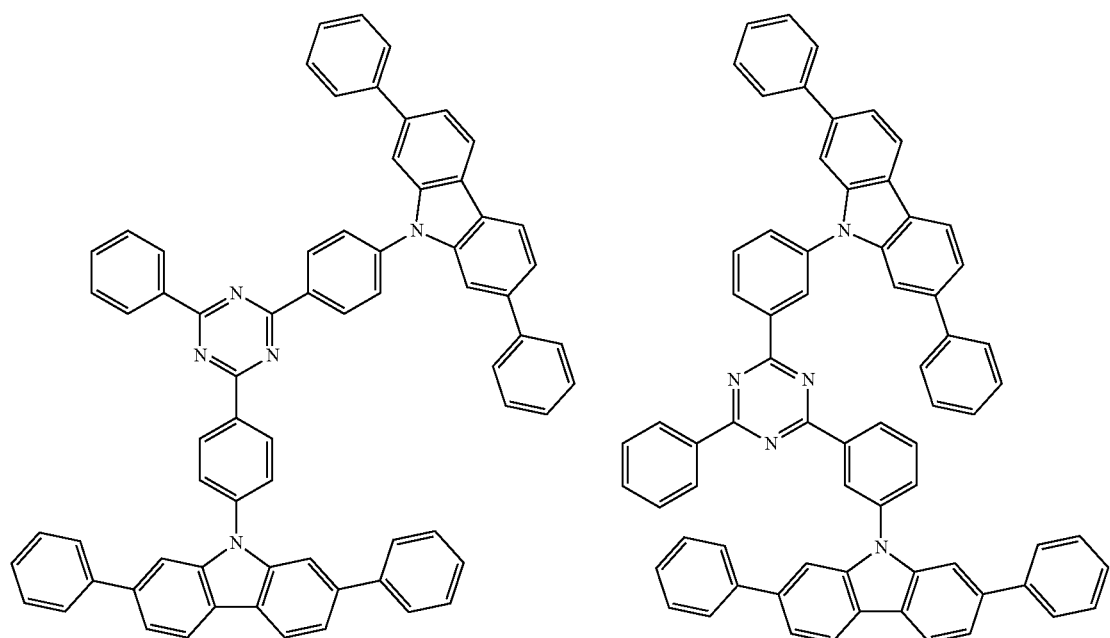
51 52
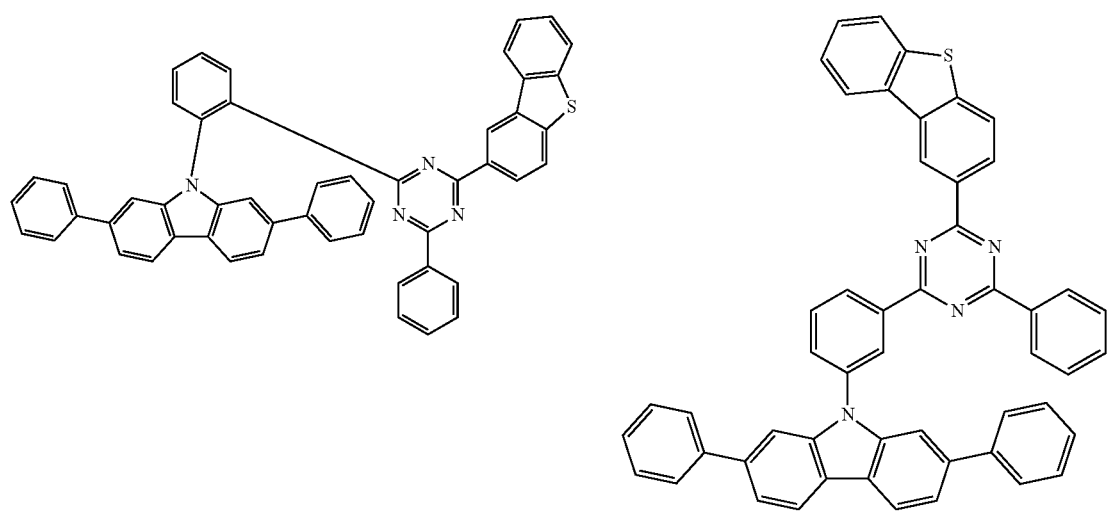

53
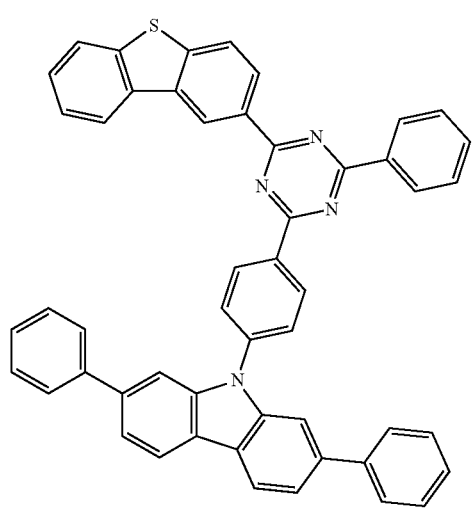
54
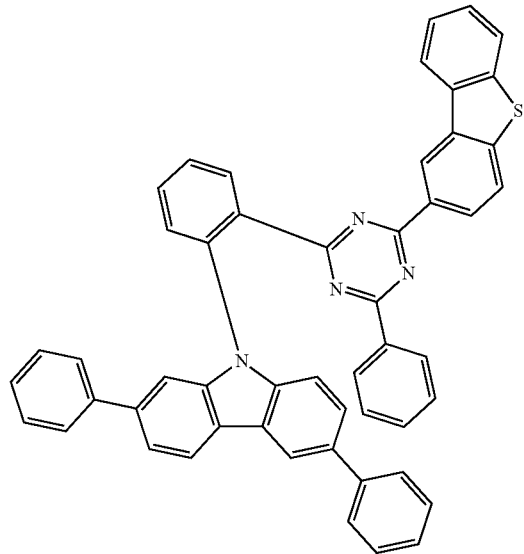
55
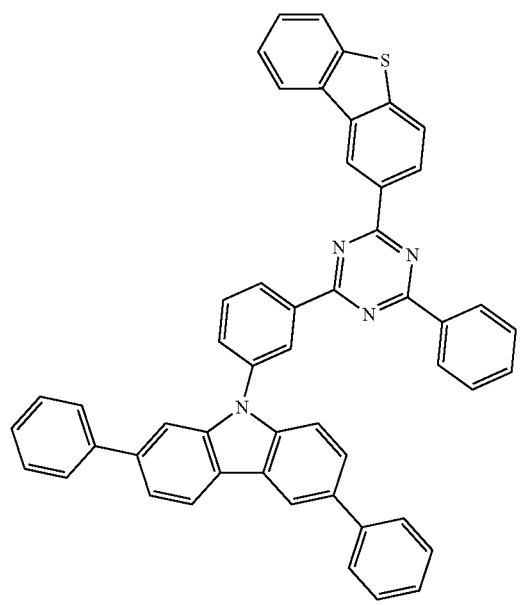
56
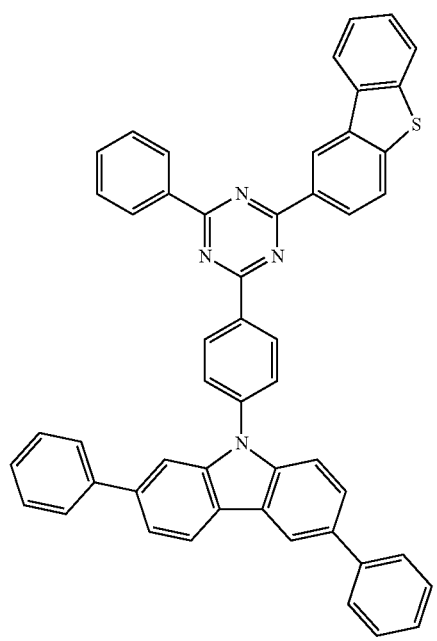

57
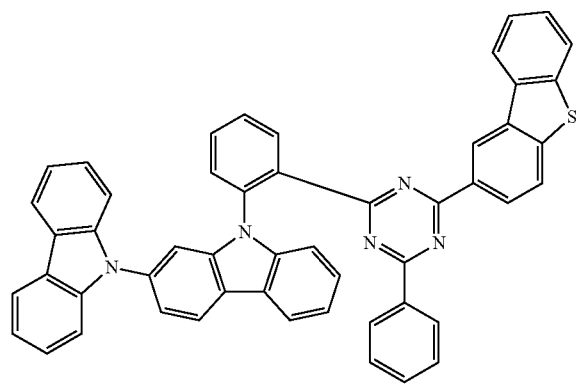
58
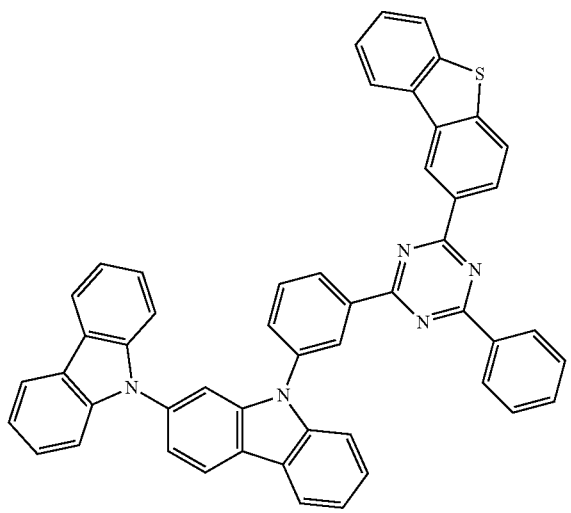
59
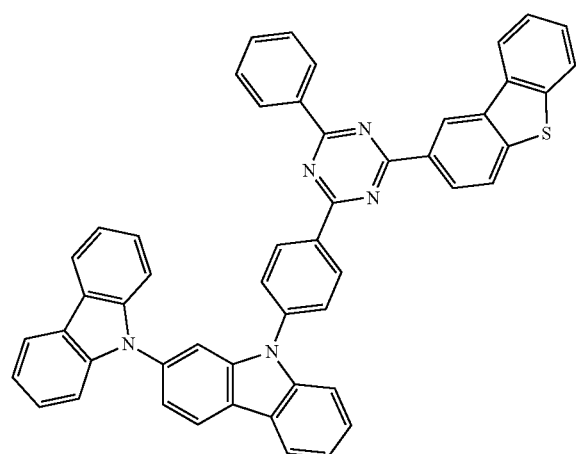
60
61
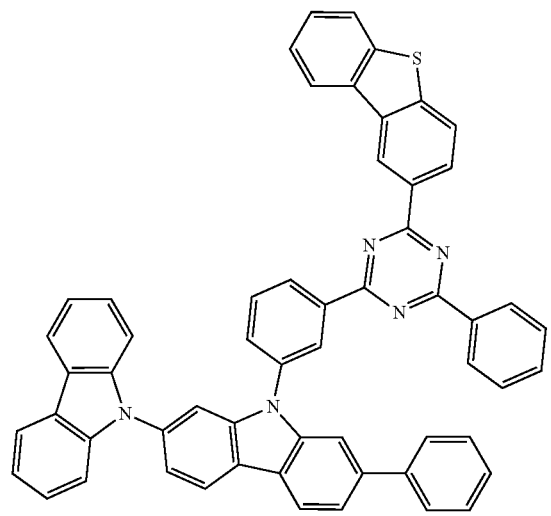
62
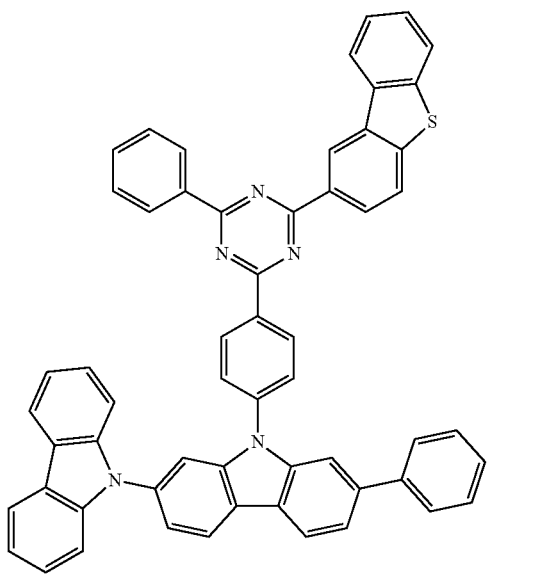

-continued
63
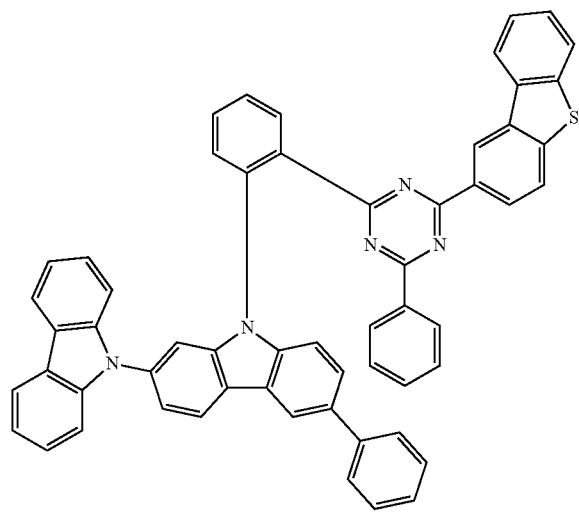
64
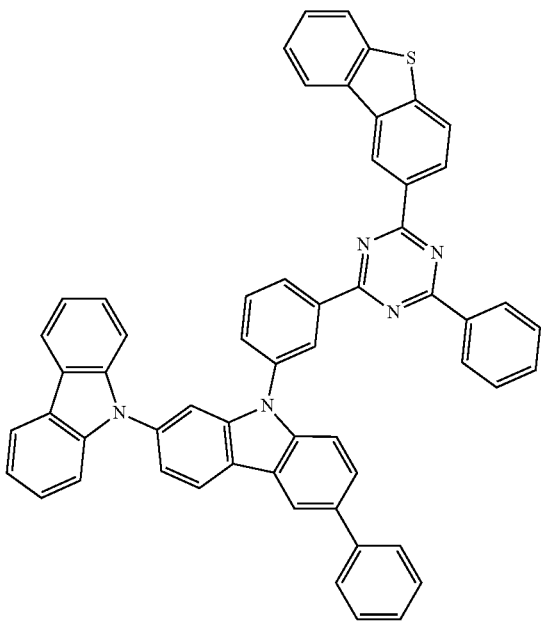
65
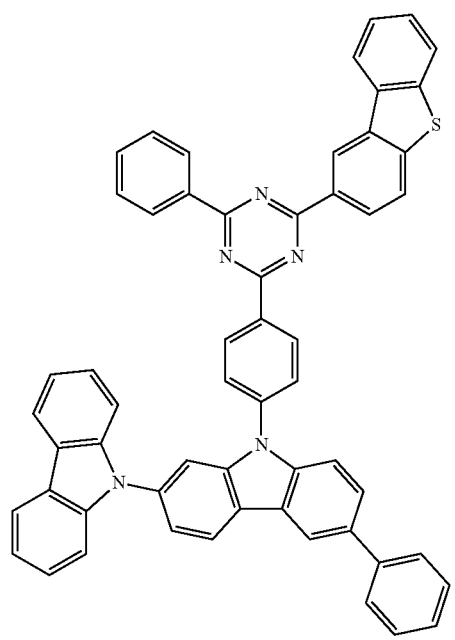
66
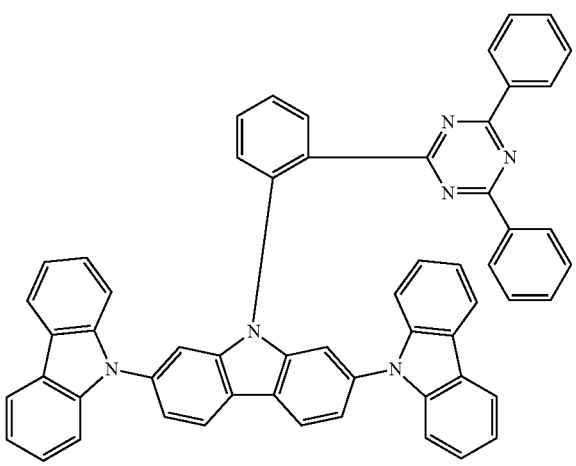

-continued
67
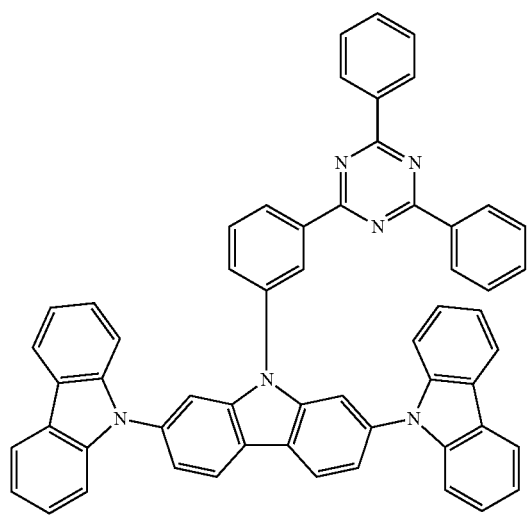
68
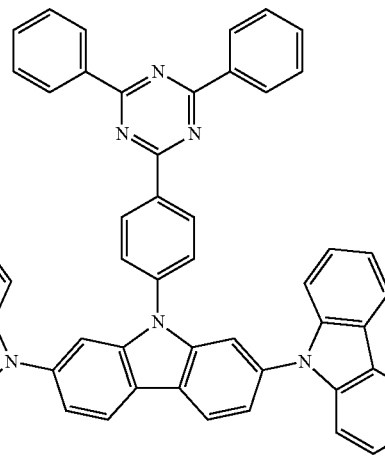
69
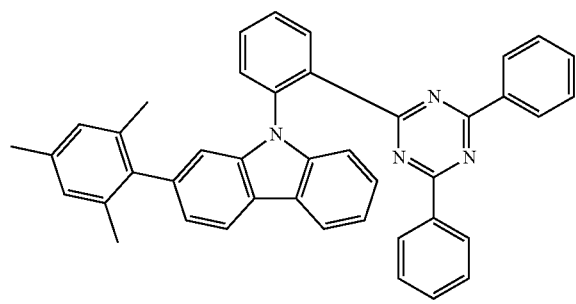
70
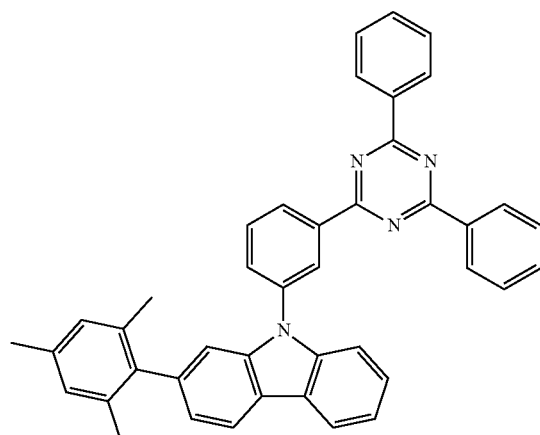
71
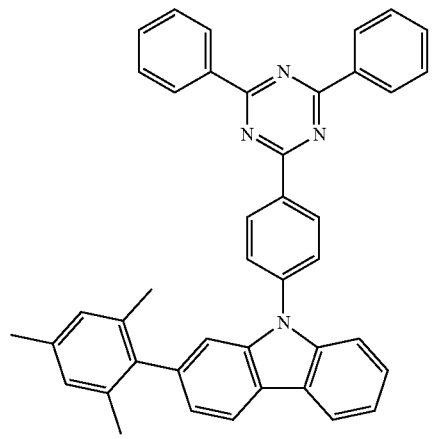
73
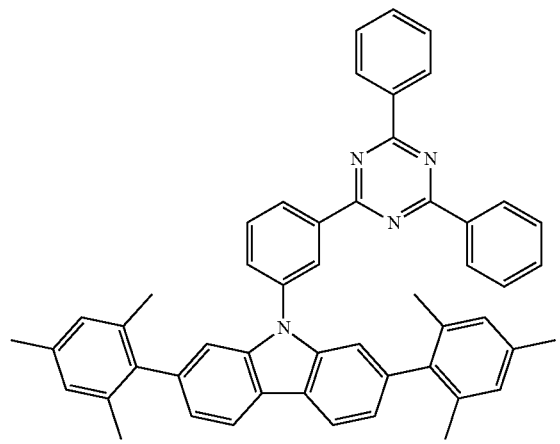

-continued
74
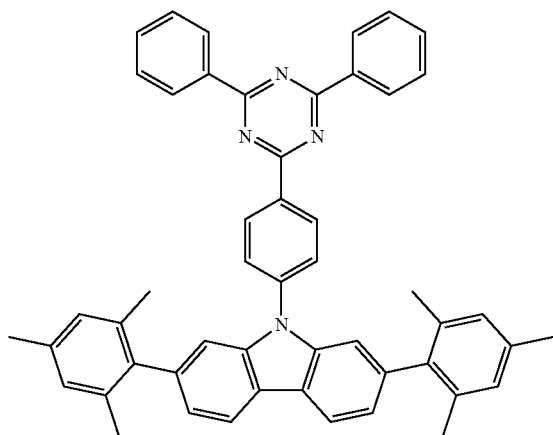
75
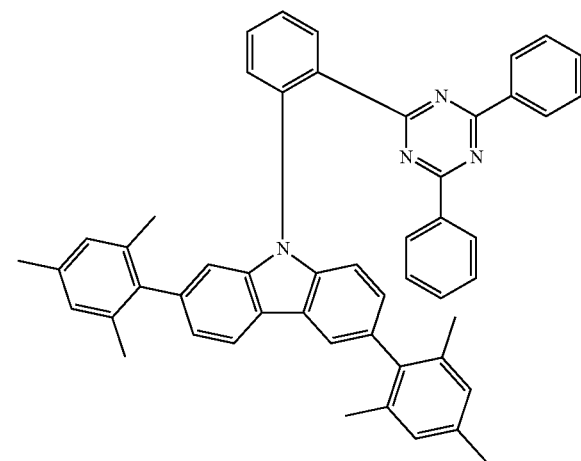
76
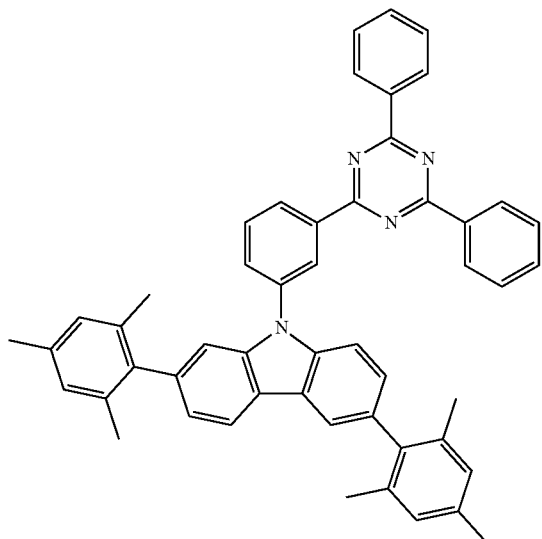
77
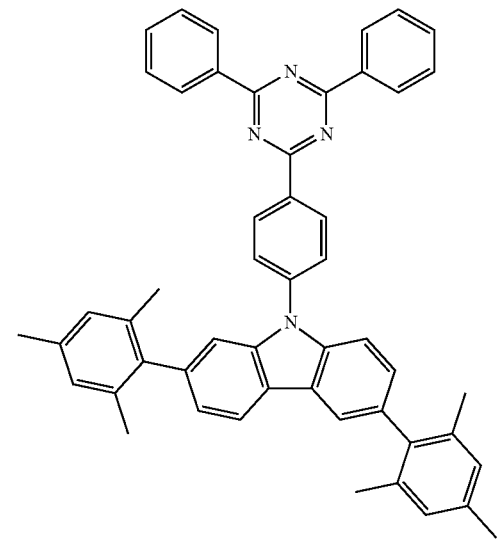
78
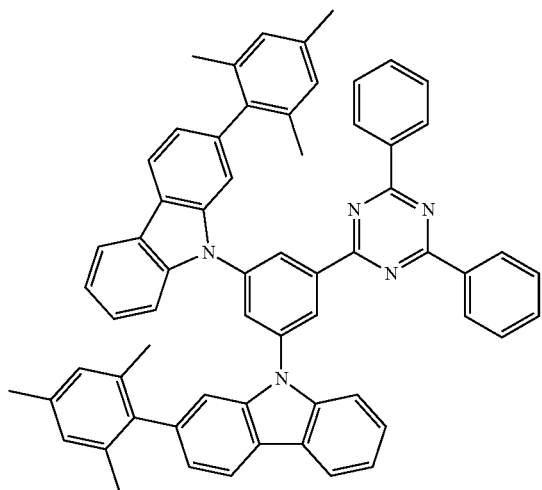
79
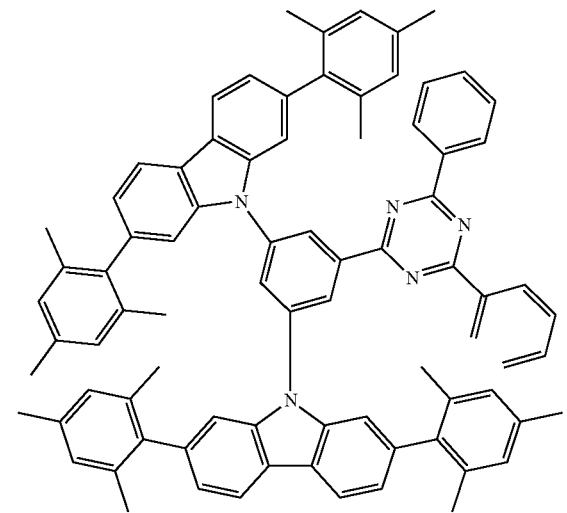

80
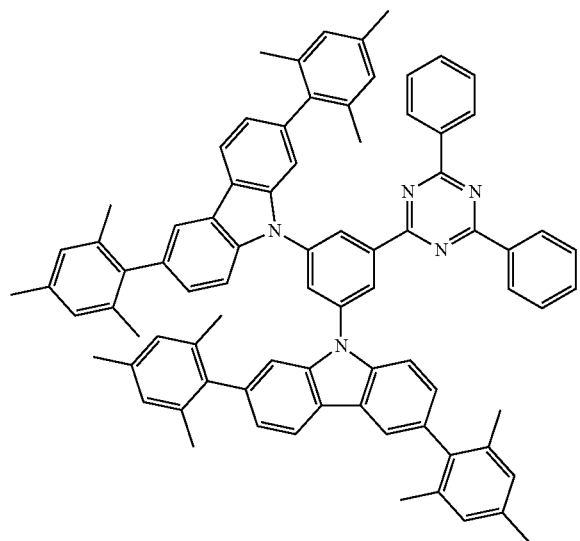
81
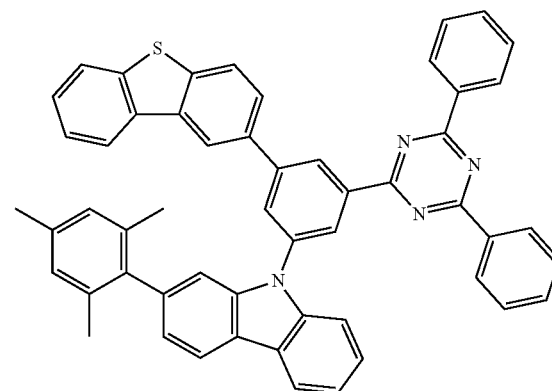
82
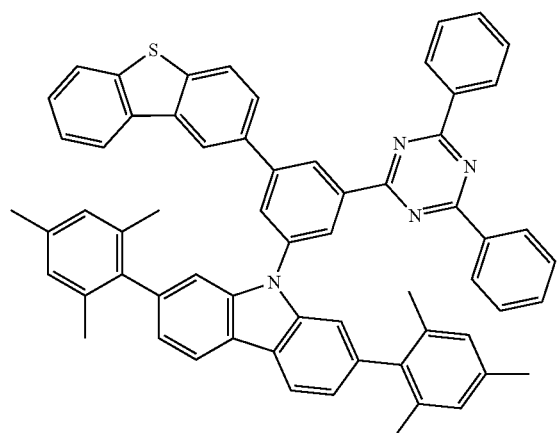
83
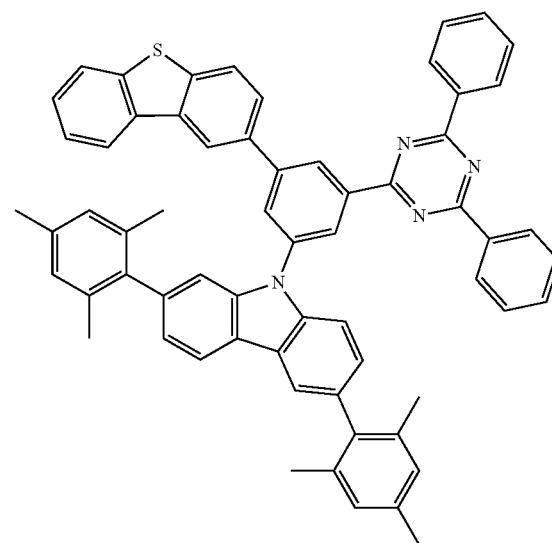

-continued
84
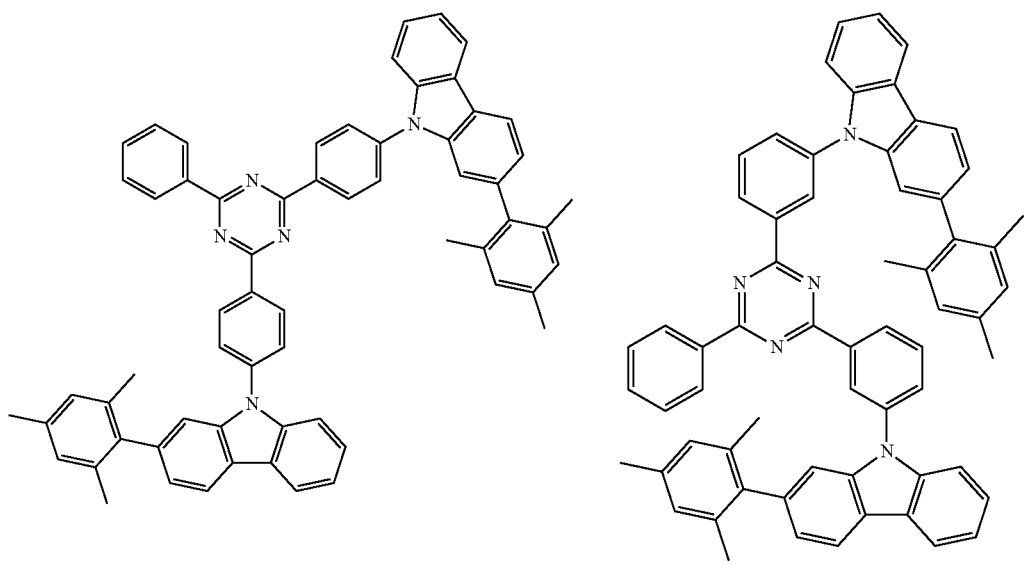
85
86
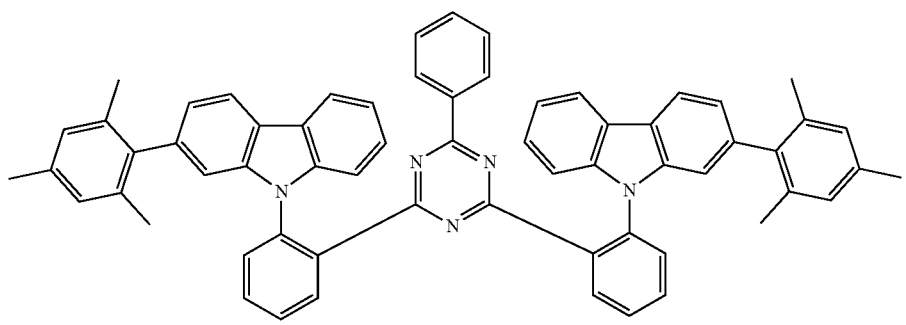
87
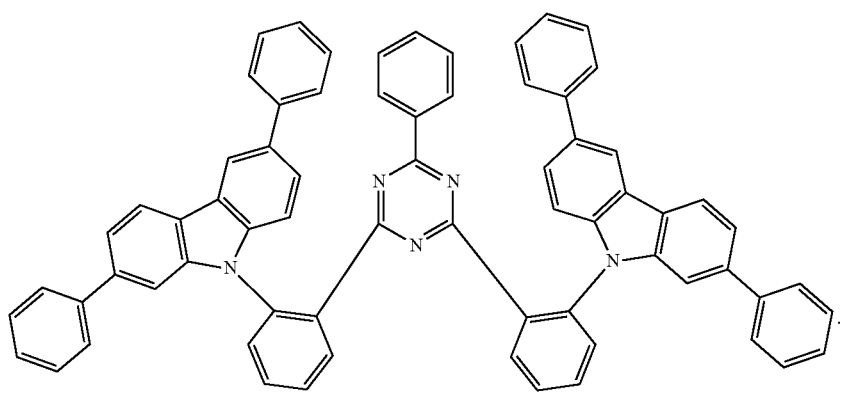
* * * * *